US012594032B2

(12) United States Patent
Datta et al.

(10) Patent No.: US 12,594,032 B2
(45) Date of Patent: Apr. 7, 2026

(54) WEARABLE HEMODYNAMIC MONITORING DEVICE AND SYSTEM

(71) Applicant: HEMODYNAMIQ WEARABLES PRIVATE (PVT) LIMITED (LTD), Bangalore (IN)

(72) Inventors: Deepanjan Datta, Bangalore (IN); Sai Kamalesh Rayaprolu, Bangalore (IN)

(73) Assignee: HEMODYNAMIQ WEARABLES PRIVATE (PVT) LIMITED (LTD), Bangalore (IN)

( * ) Notice: Subject to any disclaimer, the term of this patent is extended or adjusted under 35 U.S.C. 154(b) by 930 days.

(21) Appl. No.: 17/833,908

(22) Filed: Jun. 7, 2022

(65) Prior Publication Data

US 2022/0296165 A1 Sep. 22, 2022

Related U.S. Application Data

(63) Continuation-in-part of application No. 16/105,196, filed on Aug. 20, 2018, now Pat. No. 11,382,364.

(Continued)

(51) Int. Cl.
*A61B 5/318* (2021.01)
*A61B 5/00* (2006.01)
(Continued)

(52) U.S. Cl.
CPC .......... *A61B 5/6804* (2013.01); *A61B 5/0006* (2013.01); *A61B 5/0205* (2013.01);
(Continued)

(58) Field of Classification Search
CPC ..... A61B 5/6804; A61B 5/318; A61B 5/0006; A61B 5/0205; A61B 5/02141;
(Continued)

(56) References Cited

U.S. PATENT DOCUMENTS 9,955,876 B2    5/2018  Chirife
11,154,204 B2 * 10/2021  Trapero Martin ..... G16H 10/60
(Continued)

OTHER PUBLICATIONS

Tavallali et al., On the convergence and accuracy of the cardiovascular intrinsic frequency method, Royal Society Open Science, Dec. 16, 2015, vol. 2(12): 150475, Royal Society Publishing.

(Continued)

*Primary Examiner* — Ahmed M Farah
(74) *Attorney, Agent, or Firm* — HORIZON IP PTE LTD.

(57) ABSTRACT

The present disclosure relates to systems and methods for using a wearable device to monitor patients suffering from congestive heart failure as well as other related diseases. In particular, a wearable patch is disclosed. The wearable patch includes a patch body with a body patch side attached to and contacting a user's body as well as an opposing non-body patch side. The body patch side is configured to accommodate carotid arterial pressure sensors and bioimpedance and ECG/EKG electrodes for collecting physiological data from the user. The patch may also include jugular venous pressure sensors. A controller is disposed on the non-body patch side of the patch body. The controller includes a data collection module to receive data from the pressure sensors and the bioimpedance electrodes, a processing module to preprocess the data received, and a communication module for transmitting the preprocessed data to a backend analysis system for analysis. The backend system includes a deep learning model to analyse the behavior of carotid arterial and jugular venous pressure pulse waves, bioimpedance and ECG/EKG waveforms to predict if the patient is likely to suffer a heart failure event (HFE) or not.

16 Claims, 31 Drawing Sheets

100

Related U.S. Application Data

(60) Provisional application No. 63/281,717, filed on Nov. 21, 2021.

(51) Int. Cl.

| | |
|---|---|
| *A61B 5/0205* | (2006.01) |
| *A61B 5/021* | (2006.01) |
| *A61B 5/024* | (2006.01) |
| *A61B 5/0531* | (2021.01) |

(52) U.S. Cl.
CPC ...... *A61B 5/02141* (2013.01); *A61B 5/02438* (2013.01); *A61B 5/0531* (2013.01); *A61B 5/318* (2021.01); *A61B 2562/0247* (2013.01); *A61B 2562/028* (2013.01); *A61B 2562/164* (2013.01)

(58) Field of Classification Search
CPC .............. A61B 5/02438; A61B 5/0531; A61B 2562/0247; A61B 2562/028; A61B 2562/164
USPC ........................................................ 600/301
See application file for complete search history.

(56) References Cited

U.S. PATENT DOCUMENTS 11,253,159 B2 * 2/2022 Shusterman ....... A61B 5/02116
2014/0187976 A1    7/2014 Banet
2015/0057512 A1 *  2/2015 Kapoor .................... A61B 7/00
                                                            600/513
2016/0106366 A1 *  4/2016 Banet ................... A61B 5/0205
                                                            600/382
2016/0166155 A1 *  6/2016 Banet ................... A61B 5/7225
                                                            600/382
2017/0172423 A1 *  6/2017 Banet ................... A61B 5/7275
2017/0172516 A1    6/2017 Banet
2019/0223806 A1    7/2019 Bennet
2020/0077892 A1 *  3/2020 Tran ....................... G08B 21/02
2020/0359912 A1    11/2020 Gharib et al.
2021/0338190 A1    11/2021 Gopinathan
2023/0293082 A1 *  9/2023 Inan ....................... A61B 5/318

OTHER PUBLICATIONS

CL Garrard Jr et al, The Relationship of Alterations in Systolic Time Intervals to Ejection Fraction in Patients with Cardiac Disease, Circulation, Sep. 1, 1970, vol. 42(3):455-462.

Pahlevan NM, Tavallali P, Rinderknecht DG, Petrasek D, Matthews RV, Hou TY, Gharib M. 2014 Intrinsic frequency for a systems approach to haemodynamic waveform analysis with clinical applications. J. R. Soc. Interface 11: Jun. 17, 2014.

Donna Mancini MD, Left Ventricular Assist Devices: A Rapidly Evolving Alternative to Transplant, Journal of the American College of Cardiology, vol. 65, Issue 23, Jun. 16, 2015, pp. 2542-2555.

* cited by examiner

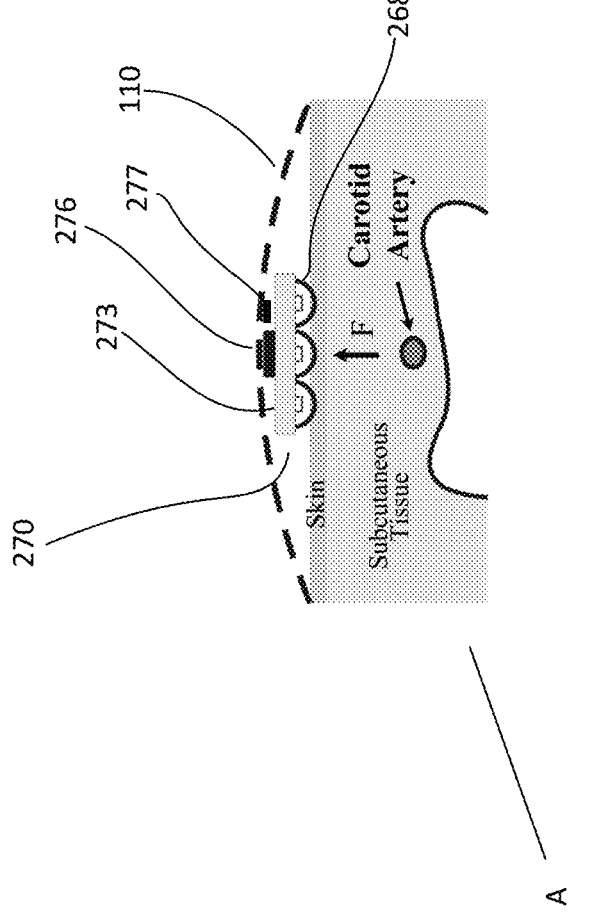
Fig. 2i₁

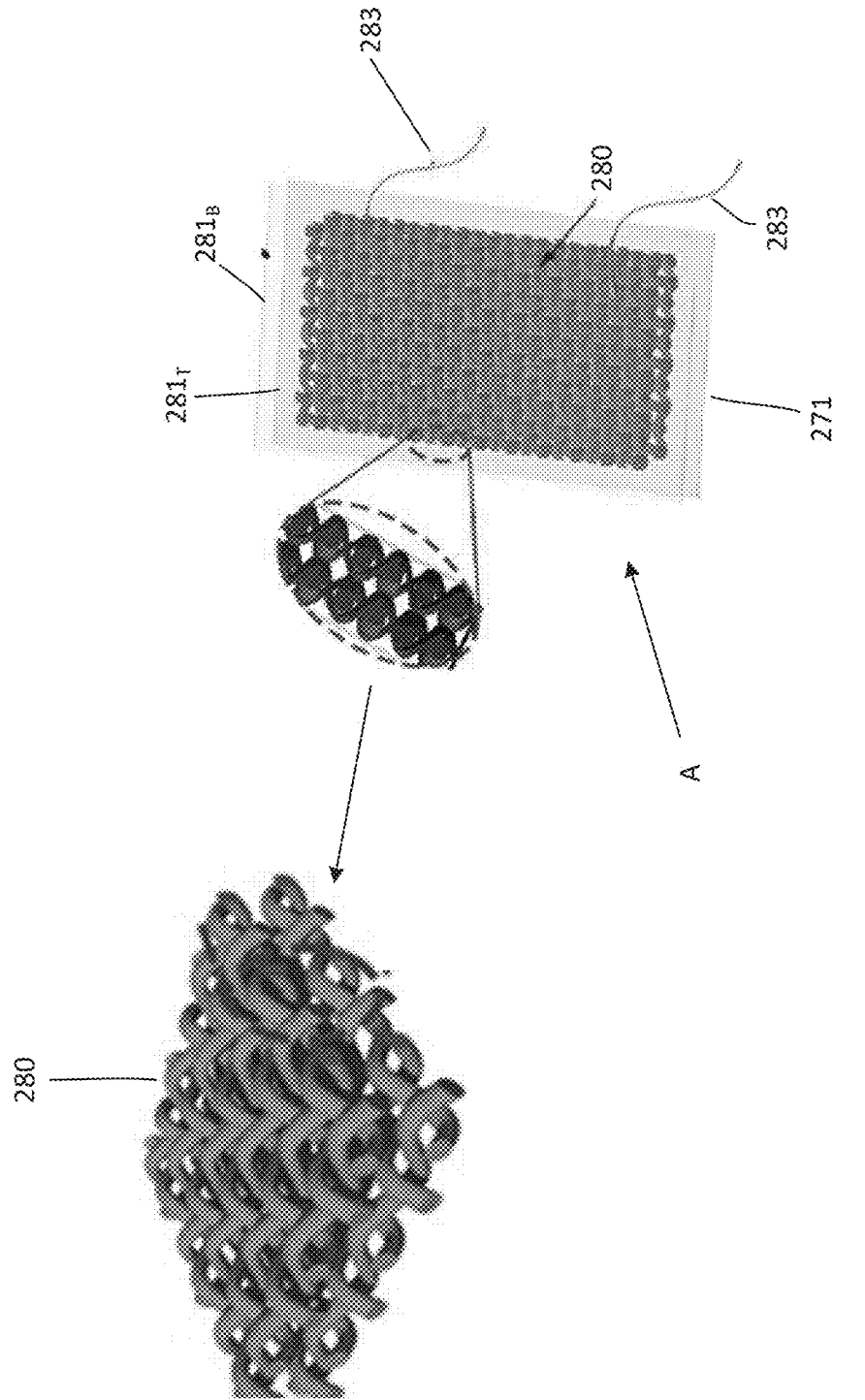
Fig. 2i₂

289

500

110

WEARABLE HEMODYNAMIC MONITORING DEVICE AND SYSTEM

CROSS-REFERENCE TO RELATED APPLICATIONS

This application claims the benefit of the US Provisional Application Ser. No. 63/281,717, filed on Nov. 21, 2021. This application is also a Continuation-In-Part application of co-pending U.S. patent application Ser. No. 16/105,196, filed on Aug. 20, 2018, which claims the benefit of the Indian Patent Application Ser. No. 201831021669, filed on Jun. 8, 2018. All disclosures are herein incorporated by reference for all purposes.

RELATED FIELD

The present disclosure relates to medical devices. More particularly, the present disclosure relates to physiological monitoring devices for monitoring vital and hemodynamic parameters which reduce unplanned hospitalizations and deaths from congestive heart failure or other related conditions with heart failure as comorbidity.

BACKGROUND

Heart failure (HF) affects an estimated 6.9 million people in the United States alone and more than 60 million people worldwide. HF is, in general, classified based on left ventricular ejection fraction (LVEF). Systolic HF refers to HF with reduced ejection fraction (HFrEF) and diastolic HF refers to HF with preserved ejection fraction (HFpEF). HF is a leading cause of death in adults over 65 years old. In particular, patients with early readmissions (hospital admissions within 30 days of being discharged from the hospital) are affected the greatest.

Early readmission of heart failure (HF) patients is often assumed to indicate or relate to incomplete treatment in the hospital, poor coordination of services or communication of plans at discharge, or inadequate access to care in early follow-up. In the United States, the early readmission rate of HF patients (within 30 days after being discharged) has been determined to range from about 10-50%, depending on the hospital. As per Agency for Healthcare Research and Quality (AHRQ), the number of risk-standardized 30-day readmission was 233,000 only in 2019. Data from a national cardiovascular registry shows that during the first year following the onset of worsening heart failure, the mean cost for HF-related care per patient is approximately $29,777 per month or $357,324 in total for the first year. This results in total one-year spending related to HF care to be approximately US $80-$100 billion for the patients with worsening heart failure symptoms. It is estimated that a large number of hospitalizations can potentially be prevented, significantly reducing healthcare spending in the USA.

We have observed that most early readmissions are related to congestive heart failure (CHF). For example, CHF patients requiring readmissions have been observed to be due to the development of acute worsening conditions. Acute worsening conditions often result in acute decompensated heart failure (ADHF). Patients with worsening heart failure are older and undergo multiple readmissions. To quell unplanned readmission rates from CHF, it is important to detect the symptoms of worsening HF conditions early. Early detection of acute worsening conditions and early prevention of heart failure decompensation, like most diseases, improves the chance of survival.

The extent of the economic burden following the development of worsening HF resulting in acute decompensation calls for further review of methods to reduce progressive disease and the development of novel treatments to moderate the further progression once HF has worsened.

Conventional best practice guidelines for monitoring CHF patients to detect acute worsening conditions are ineffective. Current techniques to detect acute worsening conditions in CHF patients include estimating changes in volume status and, in turn, the risk for impending HF events. Such techniques depend upon identifying worsening heart failure signs and symptoms and changes in body weight. However, these signals appear late and are relatively unreliable (i.e., insensitive) markers of clinical status in patients with HF. For example, daily measurement of body weight has a sensitivity of only 9% for the development of a new heart failure event. As for blood tests, such as a B-type natriuretic peptide test, although they are useful in distinguishing heart failure from other causes of shortness of breath in patients who are already in an emergency room of a hospital, they have yet proven to be helpful in the ongoing management of patients with CHF.

Moreover, HF therapy guided by monitoring of signs, symptoms, weight, and biomarkers has not been shown to improve clinical outcomes, even when incorporated into remote telemedicine systems. These systems generally integrate regular communication between patients and their medical providers with or without electronic data transfer of physiological measurements, such as signs, symptoms, body weight, and other information generally collected by non-invasive devices. However, trials conducted in this area have failed to show improvements. For example, the randomized controlled trial Tele-HF at Yale University performed between March 2006 and July 2010 did not show any reduction in the readmission or death among 1653 patients hospitalized with HF. Likewise, non-hemodynamic remote monitoring based trials, such as the "BEAT-HF" trial, have failed to show any significant reduction in the 30-day readmission or 180-day mortality and could not show any significant improvement in quality of life (QOL) of a sample size of 1437 patients hospitalized for HF between October 2011 and September 2015 at 6 academic medical centers in California, USA.

Despite current best practice guidelines, which include management within an HF clinic, early follow-up after hospitalizations, measuring daily weights and the devices which non-invasively monitor clinical parameters, such as heart rate (HR), heart rate variability (HRV), respiratory rate (RR), saturated oxygen ($SpO_2$), HF readmissions continue to occur at a rate of approximately 50% within 6 months after discharge.

Consequently, major efforts have been expended to monitor the HF status in the patients discharged from hospital and also from post-emergency department (ED) visits, with a focus on reducing hospitalization due to ADHF. In addition, the Centers for Medicare and Medicaid Services (CMS) has recently finalized their policies related to remote patient monitoring, which include analyzing patient physiologic data in order to manage a treatment plan related to chronic and acute health illnesses of established patients.

The advent of implantable pulmonary artery pressure (PAP) monitoring sensors has yielded tremendous insight into understanding the hemodynamic congestion and the gradual transition to a decompensated state, identifying time periods at risk and opportunities for intervention. For example, HF readmission is typically preceded by a gradual rise in pulmonary artery diastolic pressure or PADP that occurs greater than 2-3 weeks in advance of detectable changes in body weight or overt clinical symptoms.

While implantable devices might be useful in monitoring more advanced HF patients, they are only available for only severely affected HF patients, such as those requiring a catheter or AICD. Furthermore, implantable devices are invasive and pose risks associated with any surgical procedure. Non-invasive devices for long-term monitoring of both chronic and acute HF patients are not currently available.

From the foregoing discussion, it is desirable to provide non-invasive monitoring devices for long-term monitoring of HF patients for early detection of acute worsening conditions to enable early treatment.

BRIEF DESCRIPTION OF THE DRAWINGS

FIGS. 2h-2k show a user wearing a patch for monitoring HF and details of the pressure sensor, pressure sensor array and the bioimpedance electrode;

SUMMARY

Figure 1:
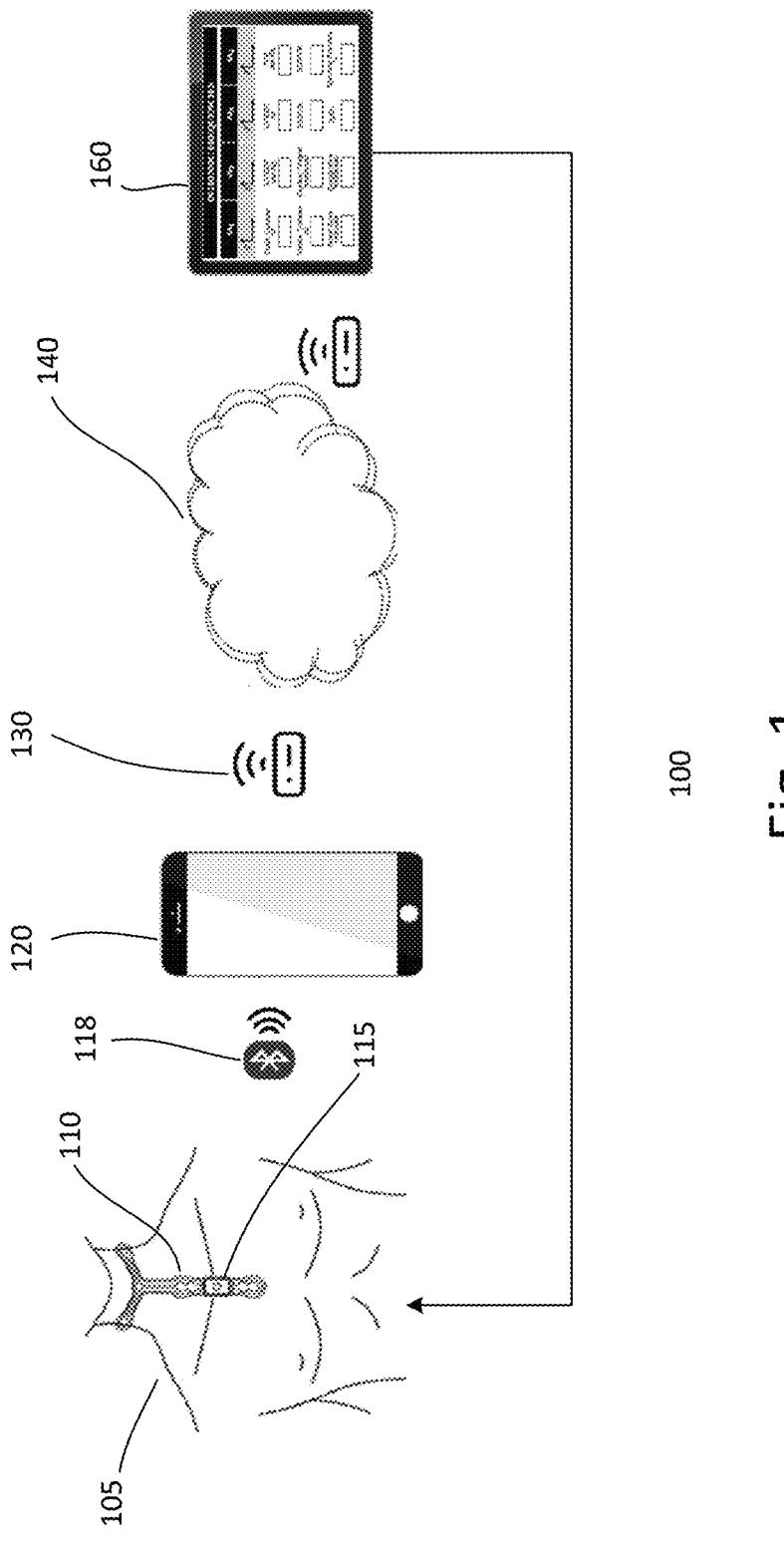
FIG. 1 shows a simplified embodiment of a system for monitoring patients.

In one embodiment, a wearable patch for monitoring the progression of congestive heart failure includes a patch body that may be worn continuously and comfortably on the upper thoracic region of a user to be monitored, for a few days up to several weeks. The patch body includes a body patch side which contacts the upper thoracic region of the body and an opposing non-body patch side. The patch body also includes a first and a second carotid arterial pressure sensor on the body patch side, and the first and second carotid arterial pressure sensors are configured on the patch body side to measure arterial pressure from common carotid arteries of the user. The patch body further includes a first and a second set of bioimpedance electrodes on the patch body side. The first and second sets of bioimpedance electrodes are configured for current injection into the upper thoracic region of the user and voltage detection from the upper thoracic region of the user. A controller is disposed on the non-body patch side of the patch body. The controller includes a data collection module that is configured to receive data (received data) from the first and second carotid arterial pressure sensors and the first and second sets of bioimpedance electrodes, a processing module configured to preprocess the received data (preprocessed data), a communication module configured to wirelessly transmit the preprocessed data from the processing module to a backend analysis system for analyzing the preprocessed data from the communication module, and a power module. The power module is configured to provide a power source to the data collection module, the processing module, and the communication module.

In another embodiment, a method for monitoring a heart failure (HF) patient is disclosed. The method includes providing a wearable patch for the HF patient to wear. The wearable patch includes a patch body for attaching to the upper thoracic region of a user to be monitored. The patch body includes a body patch side which contacts the upper thoracic region of the body and an opposing non-body patch side. The wearable patch also includes first and second carotid pressure sensors on the patch body side. The first and second carotid arterial pressure sensors are configured on the patch side to measure arterial pressure from common carotid arteries of the user. The wearable patch further includes a first and a second set of bioimpedance electrodes on the patch body side. The first and second bioimpedance electrodes are configured for current injection into the upper thoracic region of the user and voltage detection from the upper thoracic region of the user. A controller is disposed on the non-body side of the patch body. The controller is configured to receive data (received data) from the first and second pressure sensors and the first and second sets of bioimpedance electrodes, preprocess the received data (preprocessed data) and transmit the preprocessed data to a backend analysis system.

In yet another embodiment, a backend analysis system for real-time monitoring of a heart failure (HF) patient is disclosed. The system involves generating a customized baseline model, based on predicting the behavior of the waveforms obtained from the wearable patch worn by the heart failure patient, multiple days ahead before hospitalization occurs and also to calculate the future clinical parameters from those predicted waveforms. Those predicted parameters can signify whether a patient is likely to suffer hospitalization or not. The system includes a multiple waveform predictor module. The waveform predictor module processes previous days' waveforms measured from a patch worn by the patient and outputs the predicted waveforms the patient is supposed to develop in the next few days. A user may exhibit large variations in hemodynamic and impedance waveforms over time. This may occur due to physiological changes, which are responsive to metabolic needs, activity, environment, diurnal cycles and others, or, due to worsening of heart failure or even due to healthcare system factors such as suboptimal care in the skilled nursing facilities. In contrast to a sedated HF patient in a hospital setting, the physiological conditions of the heart failure patients at home or at a skilled nursing facility are exceptionally altered by such variations, and as a result of the baseline model deployed to monitor the user's hemodynamic and impedance-based parameters will get changed/updated periodically based on the predicted waveforms. The predicted waveforms are then compared against the baseline model to determine the changes in the cardiovascular or circulatory conditions of the user and may detect abnormalities in the predicted waveforms over time. The method further includes generating an alert to a patient having worsening heart failure, rather than passing it on as just a concept drift where a gradual change in baseline occurs due to some non-harmful environmental events.

DETAILED DESCRIPTION

The present disclosure relates to wearable devices as well as systems and methods for monitoring patients. More particularly, the present disclosure relates to wearable devices and systems and methods for hemodynamic monitoring to characterize patients suffering from heart failure with reduced ejection fraction (HFrEF) or heart failure with preserved ejection fraction (HFpEF) as well as other related diseases. For example, wearable devices and systems and methods are useful for monitoring patients with congestive heart failure (CHF) and other severe left ventricular systolic and diastolic dysfunctions.

FIG. 1 shows an embodiment of a system 100 for monitoring patients. As shown, the system includes a wearable device 110. The wearable device, for example, is in the form of a patch that is worn on an upper part of the chest of a patient (user) 105. The patch is designed to be worn continuously and comfortably for a short period of time (such as a few hours to a few days) or for a longer period time (such as up to several weeks). The wearable device may be configured with dry conductive electrodes for current injection and voltage detection and internet of things (IoT) electronics which include bioimpedance and ECG/EKG electrodes. In addition, the wearable device includes pressure sensors or pressure sensor arrays for detecting the arterial pressure waveform of the user from the common carotid artery. The term "pressure sensor" may generically refer to a pressure sensor, pressure sensors, a pressure sensor array or pressure sensor arrays. Likewise, the term "pressure sensors" may generically refer to a pressure sensor, pressure sensors, a pressure sensor array or pressure sensor arrays. The wearable device may also include an optical sensor system along with a plurality of photodiodes and LED(s) for measuring photoplethysmography waveform from the mid-sternal region of the user's chest.

The wearable device may include a processing unit 115 which is configured to receive the acquired data, which includes carotid artery pressure waveforms along with thoracic bioimpedance signals, ECG/EKG and PPG waves. With respect to the thoracic bioimpedance signals, they are processed, separating them into cardiac and respiratory components. The processing unit transmits the waveforms (pre-processed waveforms) to the IoT gateway, such as a user's mobile device 120 via a short-range wireless transmitter module 118. The user's mobile device may be, for example, a smartphone or a tablet computer which may run on any platform, such as Android or IOS or Windows. Other types of mobile devices or platforms may also be useful. For example, the mobile device may be a dedicated device for receiving the pre-processed waveforms from the processing unit of the wearable device. As for the short-range wireless transmitter module, it may be a Bluetooth transceiver module or an Electro-Quasistatic human body communication (EQS-HBC) module. For example, in the case of a Bluetooth transceiver module, the Bluetooth modules of the processing unit and the mobile device are paired to enable the transmission of the pre-processed data. In the case of an intrabody EQS-HBC module, pressure or hemodynamic waveforms are coupled to the surface of the human body using an interfacing electrode which protrudes from beneath the transmitter with the communication module, processing module, memory, and power source. The transmitted signal flows through the low resistance layers of the body below the skin and is picked up by the receiver electrode, thus producing a covert communication channel. The EQS-HBC module may be preferred over the Bluetooth transceiver module due to its lower power consumption and higher data rate. For example, an EQS-HBC module may consume about 100× less power with 10× higher data rate than a Bluetooth transceiver module. Other types of short-range wireless transmitter modules may also be useful.

The pre-processed data is then sent to a server 140 via WiFi or cellular systems 130 for analysis using deep learning-based models. The deep learning models may have a cascaded or an ensemble architecture to handle the diversity of the waveform data. Other types of models may also be useful. In one embodiment, the server is a web-based server located on a cloud. Other configurations of the server may also be useful. The deep learning models are trained to be specific to each user's baseline characteristics. Due to the variation in baseline characteristics of hemodynamic and bioimpedance waveforms from user to user, this technique is effective for remote patient monitoring or RPM.

The waveforms obtained from the patch worn by the heart failure patient who is either relatively stable at home after the discharge from a hospital or post-emergency department (ED) visit or, alternatively, currently visiting skilled nursing facilities (SNF) or under observation by home health agencies (HHA), are used to predict next few days of the waveforms using waveform predictor modules. The waveform predictors are a predictive machine learning (ML) model which would take several days of data as input and predict waveforms that the patient is supposed to develop over the next few days as the output. To achieve this, the ML model would require pre-processing, such as noise removal, feature extraction, missing value interpolation as well as other preprocesses. Depending on the diversity of the waveforms' characteristics, some of the waveform predictor models may need to have a cascaded or an ensemble architecture. Subsequently, the predicted waveforms are taken as inputs and are used to detect the characteristic points on the input waveforms to stochastically compare with corresponding points on the other predicted waveforms. A recurrent neural network (RNN) based deep learning model may be used to predict the baseline characteristics using the extracted features from the predicted waveforms.

We live in a rapidly changing environment where more and more data is stored in data repositories, such as a cloud server, daily. A patient can exhibit significant variations in the hemodynamic as well as the bioimpedance-based parameters over time. These variations might be natural, occurring due to physiological changes, which are responsive to metabolic needs, activity, environment, diurnal cycles as well as other factors, or due to worsening of heart failure. These variations might also be due to healthcare system factors such as suboptimal care in skilled nursing facilities. Because the changes in the hemodynamic and impedance waveforms will cause a change in each patient's baseline characteristics, it is essential to detect the reason behind such variations. For example, it is essential to determine whether the cause is worsening heart failure conditions, suboptimal care post-discharge or other non-harmful environmental factors. In contrast to a sedated HF patient in a hospital setting, the physiological conditions of the HF patients at home or a skilled nursing facility may be different due to variations in conditions. As such, the baseline model deployed to monitor the user's hemodynamic and impedance-based parameters may be inaccurate. For example, in a sedated condition in the hospital, the physiology of heart failure patients might exhibit substantial differences compared to patients at home or in a skilled nursing facility. Such variations may hide early changes in physiological parameters that evidence early deterioration of health.

Upon the formation of the baseline model, the predicted waveforms for each patient are compared against their respective baseline characteristics to determine the changes in their cardiovascular or circulatory conditions. The clinical parameters calculated using the predicted waveforms may be sent to the physician of the user. For example, these parameters may be displayed on the physician's device, such as in the form of a dashboard 160. Furthermore, the model includes a detection strategy using an anomaly detector that determines patterns of anomalous waveforms and triggers an alert rather than passing it on as just a concept drift where a gradual change in baseline occurs due to other non-harmful environmental events. The alert triggered may cause the patient to be instructed or may instruct the patient to visit the physician. Therefore, these predicted parameters can signify whether the patient is likely to suffer hospitalization or not. This forms the basis for early detection of HF events, aiming at reducing the hospitalization of HF patients by preventing them from reaching a critical stage. Thus, obtaining the hemodynamic and impedance waveforms, preprocessing them using an ML model, predicting the future waveforms using the former as an input, extracting the characteristic points in the predicted waveforms, using these to estimate the baseline parameters through continuous training and validation, and finally detecting the abnormalities in the predicted waveforms and triggering an alert to the patients as well as the physicians form a closed loop.

Figure 2A:
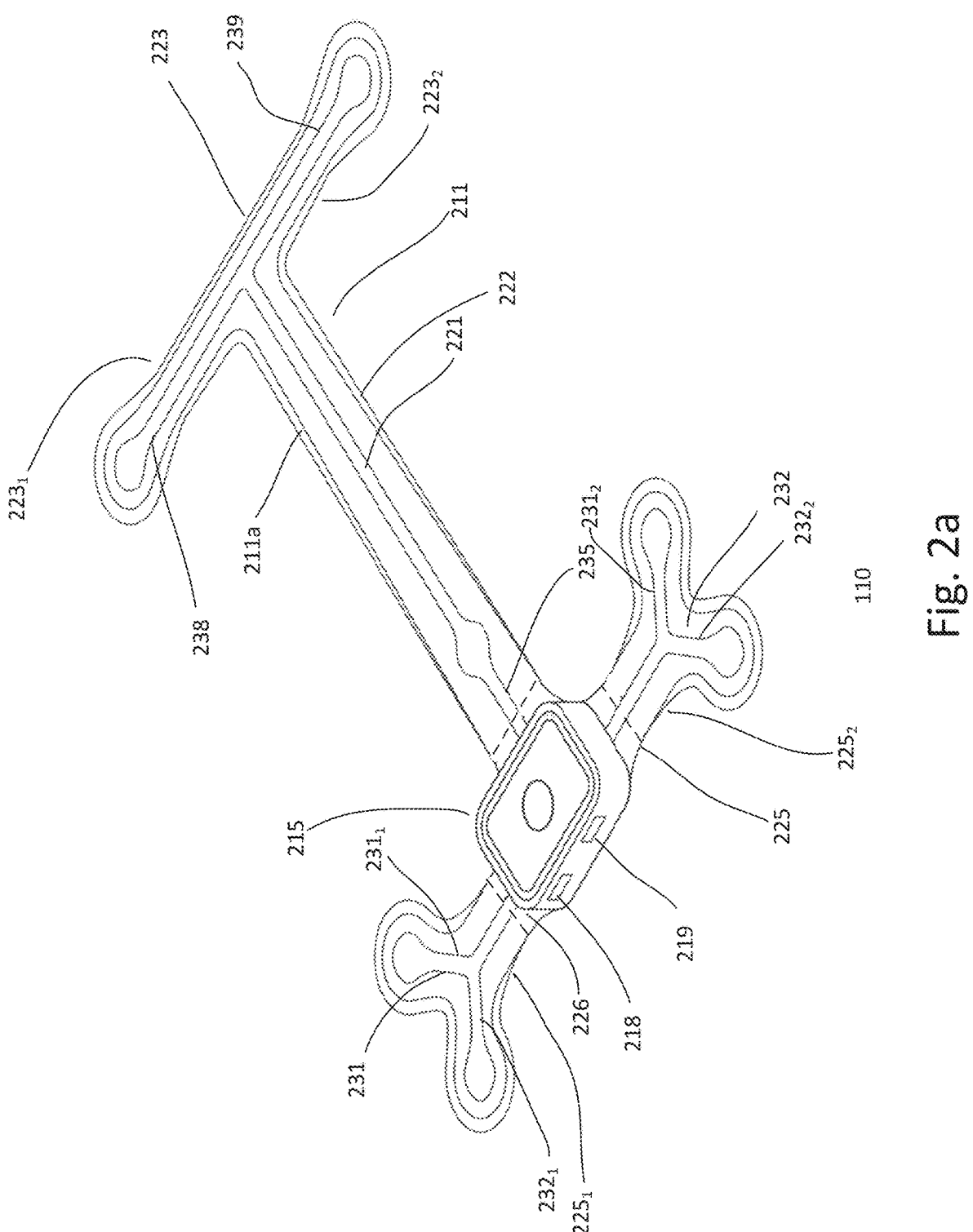
FIGS. 2a-2c show various views of an embodiment of a wearable monitoring device.
Figure 2B:
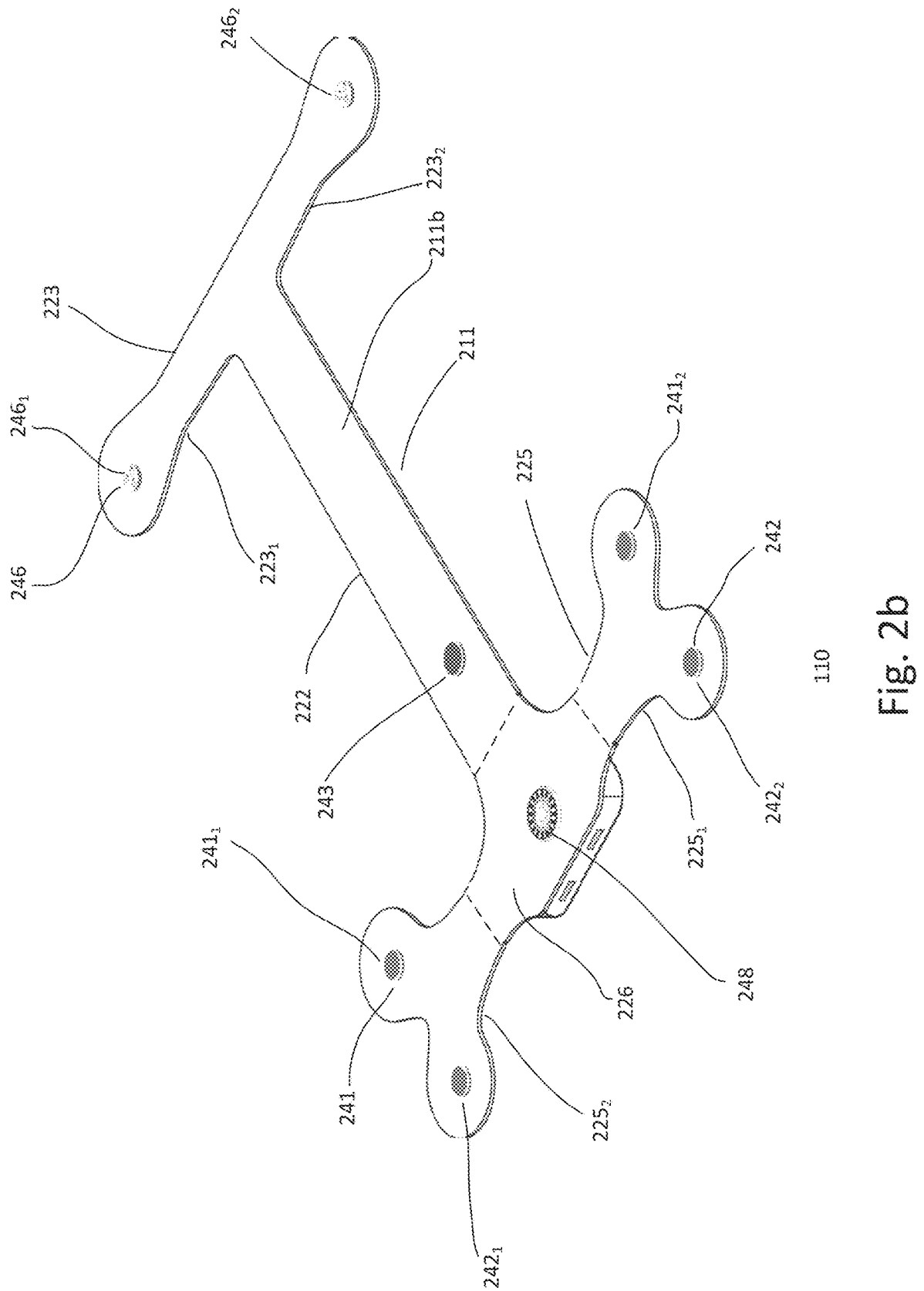
Figure 2C:
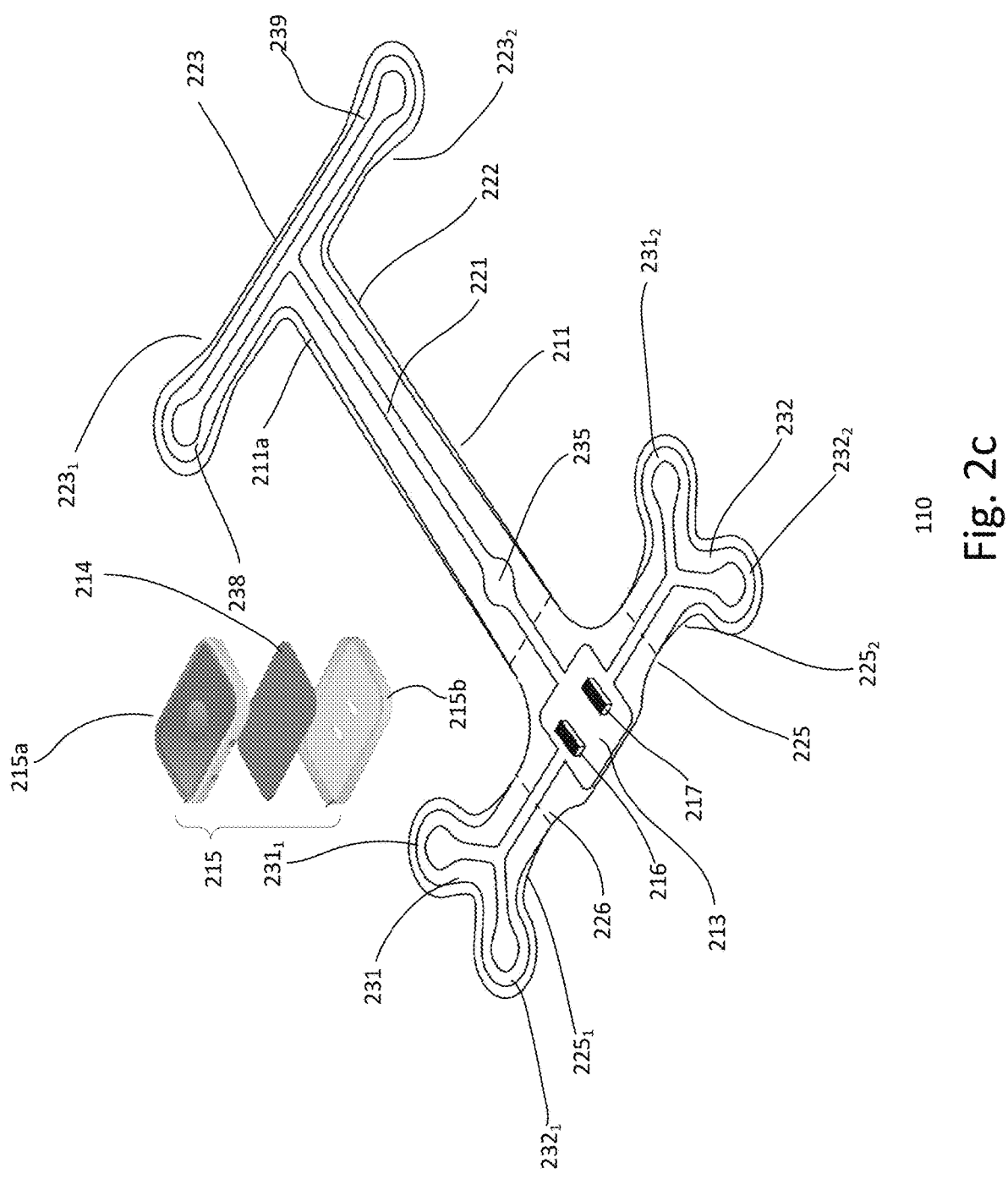

FIGS. 2a-2c show various views of an embodiment of a wearable device 110. In particular, FIG. 2a shows a 3D front perspective view, FIG. 2b shows a 3D back perspective view skin side and FIG. 2c shows a 3D exploded front perspective view. As shown, the wearable device, for example, is a patch which includes various components for monitoring heart failure events of a user. In one embodiment, the wearable device includes a flexible patch body 211. The flexible patch body conforms to the body contour of the user when worn.

The flexible patch body includes front and back patch body surfaces 211a and 211b. The back patch body surface is the surface which contacts the skin of the user (skin side) while the front body surface does not (non-skin side). To facilitate wearing (attaching) of the wearable device onto the user's skin, the back body surface includes an adhesive layer. The adhesive layer may be a polymer-based adhesive layer. For example, the adhesive layer may be a liquid-based adhesive or pressure-sensitive adhesive (PSA) tie layer. Other types of adhesives, such as silicone-based adhesives or hydrocolloid adhesives that contain naturally derived or synthetic absorbent materials which take up moisture from the user's skin during perspiration, may also serve as the adhesive layer.

As shown, the body includes an elongated central body member 222 having first and second central member ends. The central body member, for example, is along a longitudinal direction. The central member, for example, is designed to extend from the neck to the sternum of the user. For example, the first central member end is designed to be located at the neck of the user while the second central member end is designed to be located at the sternum of the user.

The flexible patch body includes first extensions 223 extending laterally from about the first end of the central body member. As shown, the first extensions include a first extension portion $223_1$ extending from the central body member in a first lateral direction and a second extension portion $223_2$ extending from the central body member in a second lateral direction, which is opposite the first lateral direction. This forms, for example, a T-shaped upper portion of the patch body at the first end of the central body member.

In one embodiment, wing extensions 225 extend laterally from about the second end of the central body member. The wing extensions include a first wing extension portion $225_1$ extending from the central body member in the first lateral direction and a second wing extension portion $225_2$ extending from the central body member in the second lateral direction. The wing extensions extending from the second end of the central body member form a lower portion of the patch body. The wing extensions similarly form a T-shaped lower portion in which the ends are winged tipped. Other shaped wing extensions may also be useful.

The patch body may be arranged as a single unit. For example, the shape or profile of the patch body may be a single unit. In such cases, the central body member, extensions and wing extensions are formed as a single unit. In other embodiments, the patch body may be formed from multiple units. For example, the central body member and the extensions are one unit while the wing extensions are formed of three units, such as the first and second wing extension portions and a shoulder or hinge portion 226 therebetween, as indicated by dotted lines, which may serve as the second end of the central body member. Other configurations of the patch body may also be useful.

In one embodiment, electrodes and pressure sensors are disposed on the back patch body surface, enabling them to contact the user's skin. In a preferred embodiment, the electrodes include dry electrodes. For example, the dry electrodes are conductive textile electrodes. The use of dry electrodes avoids skin abrasion as well as the need for gels to operate. Other types of electrodes may also be useful.

In one embodiment, the first and second wing extension portions are configured to accommodate dry electrodes 241 and 242. As shown, the first wing extension portion accommodates a first pair of electrodes $241_1$ and $242_1$ and the second wing extension portion a second pair of electrodes $241_2$ and $242_2$. The first pair of electrodes serve as a first set of bioimpedance electrodes and the second pair of electrodes serve as a second set of bioimpedance electrodes. Each set or pair of electrodes includes a first or input electrode 241 ($241_1$ for the first electrode pair and electrode $241_2$ for the second electrode pair) and a second or output electrode 242 ($242_1$ for the first electrode pair and electrode $242_2$ for the second electrode pair).

In one embodiment, a positive current (I+) is provided at the input electrode $241_1$ of the first set of bioimpedance electrodes and a positive voltage (V+) is output by the output electrode $242_1$ of the first set of bioimpedance electrodes; a negative current (I−) is provided at the input electrode $241_2$ of the second set of bioimpedance electrodes and a negative voltage (V−) is output by the output electrode $242_2$ of the second set of bioimpedance electrodes. The output or voltage electrodes of the first and second sets of bioimpedance electrodes are configured to measure both ECG/EKG waveforms and bioimpedance waveforms simultaneously. As shown, the current electrodes are disposed above the voltage electrodes when the patch is worn. Other arrangements for the electrodes may also be possible.

The central body member accommodates, in one embodiment, a right leg drive (RLD) electrode 243 for measuring RLD voltage ($V_{RLD}$). The RLD electrode, for example, is disposed proximate to the wing extensions. A photoplethysmography (PPG) sensor 248 is located at about the second end of the central body portion between the wing extension portions. The PPG sensor, for example, is an optical sensor system along with a plurality of photodiodes and one or more light-emitting diodes (LEDs) for detecting the PPG signal.

As for the extension portions, in one embodiment, they accommodate pressure sensor arrays 246. For example, the first extension portion accommodates a first pressure sensor array 246$_1$ and the second extension portion accommodates a second pressure sensor array 246$_2$. The pressure sensor arrays are configured to provide conformal contact with the user's skin to detect the pressure pulse waveform from the common carotid artery. In one embodiment, the pressure sensor arrays include microelectromechanical system (MEMS) based capacitive pressure sensors, such as SCB10H sensors from Murata. In one embodiment, three or more pressure sensor elements are assembled as an array on a flexible PCB. The array configuration relaxes the requirement for accurate positioning of the device and therefore improves the reproducibility of the measurement.

In other embodiments, the pressure sensors include piezoresistive pressure sensors. For example, piezoresistive pressure sensors instead of MEMS-based pressure sensors are used. A piezoresistive pressure sensor may be formed from nanofiber yarns. In one embodiment, the piezoresistive sensor is formed from a double-layered nanofiber woven fabric, such as poly(3,4-ethylene dioxythiophene) (PEDOT) conductive polymer and polyvinylidene difluoride (PVDF) piezoelectric polymer thin films i.e., PEDOT@PVDF nanofiber woven fabric abbreviated as PPNWF. The PPNWF is sandwiched by the top and bottom polydimethylsiloxane or PDMS films. The PPNWF pressure sensor is self-powered because of the piezoelectricity of the PVDF β-phase, and the output voltage may exhibit a distinct switching behavior to applied pressure. The PPNWF pressure sensor serves as a wearable electronic skin to detect subtle stresses, measuring the pressure pulse waveform from the common carotid artery of the user as well as detecting small-scale movement. Other types of pressure sensors may also be useful.

The front patch body surface includes a rigid electronic housing 215 which houses a circuit board with electronics for receiving pre-processed data from the sensors and electrodes and transmitting the pre-processed data to, for example, the mobile device of the user for further transmission to a server. In one embodiment, the electronic housing includes top and bottom housing parts 215*a-b* encasing the circuit board 214. The circuit board within the housing may be the main circuit board (main PCB). The front patch body surface below the rigid housing includes a bottom circuit board (bottom PCB) 213 with connectors 216 and 217 which electrically connect a trace unit 221 with signal traces to the main PCB. The connectors may be referred to as board-to-board (B-to-B) connectors. The signal traces of the trace unit, for example, terminate at the bottom PCB and are connected to the main PCB through the B-to-B connectors. The signal trace unit is a flexible signal trace unit. The electronic housing also includes an on-off switch 218 for switching on the wearable device to collect and transmit data as well as a charge port 219. The charge port, for example, may be a USB port. The charge port is used to charge a battery disposed in the electronic housing for operating the patch.

In one embodiment, the trace unit includes signal traces connecting to the various electrodes and sensors. Different signal traces, such as those for sensors and those for electrodes, may have different numbers of signal lines (including power signals, such as voltage or voltages and ground). The number of signal lines for the signal traces, for example, may depend on the types and configurations of the electrodes and sensors.

In one embodiment, the trace unit includes pressure signal traces 238 and 239 connecting to the pressure sensor arrays. For example, a right pressure signal trace is connected to the right pressure sensor array and a left pressure signal trace is connected to the left pressure sensor array. In one embodiment, a pressure signal trace includes three signal lines, two voltage signal lines and a ground line to power a capacitance-to-digital converter (CDC) and a wireless transmission module. The pressure pulse signal is transmitted wirelessly to the main PCB by the wireless transmission module. As such, pressure signal lines are not needed. In other embodiments, the pressure pulse signal may be transmitted to the main PCB via SPI/I2C/GPIO/UART interfaces through the B-to-B connector or connectors. In such cases, the pressure signal trace includes an additional signal line. The trace unit also includes bioimpedance electrode signal traces 231 and 232 connected to the first and second set of bioimpedance electrodes (electrode signal traces 231$_1$ and 232$_1$ for the first set of bioimpedance electrodes and electrode signal traces 231$_2$ and 232$_2$ for the second set of bioimpedance electrodes) and RLD electrode signal trace 235 connected to the RLD electrode. The trace unit may also include a Photoplethysmography (PPG) sensor signal trace. Preferably, the PPG sensor is directly connected to the bottom PCB. This, for example, enables the PPG sensor to be in direct contact with the user's midsternal region of the chest. Other configurations of the signal traces of the trace unit may also be useful.

As shown, the signal trace unit is visible from the front patch surface. In one embodiment, the signal trace unit is embedded within the patch body. As such, the signal trace unit may not be visible at all. The signal trace unit is shown, for example, to facilitate understanding.

In one embodiment, the patch body is formed from multiple layers. In one embodiment, the patch body includes upper and lower substrate layers sandwiching the signal trace unit. For example, the signal trace unit is embedded between the top and bottom substrate layers. The top substrate layer may serve as the front patch surface and the bottom substrate layer may serve as the back patch surface.

The top and bottom substrate layers may be made of a flexible material, such as one or more flexible polymers. Flexible polymers can include, for example, polyurethane, polyethylene, polyester, polypropylene, nylon, Teflon and carbon impregnated vinyl or a combination thereof. Other types of flexible materials may also be useful. The material of the substrate layers may be selected based on desired characteristics. For example, the material of substrate layers may be selected for flexibility, resilience, durability, breathability, moisture transpiration, and adhesion as well as other characteristics. In one embodiment, for example, the top substrate layer may be made of polyurethane, and the bottom substrate layer may be made of polyethylene or polyester. In other embodiments, the substrate layers may be made of the same material. In yet another embodiment, the substrate layer may contain a plurality of perforations in the area over the adhesive layer to provide for even more breathability and moisture transpiration.

As discussed, the wearable monitoring device or patch may be worn continuously by a patient, such as for a few weeks or more, without removal during the time of wear. For example, the user may continuously wear the device during various activities, such as sitting, exercising, sleeping as well as other activities. As such, the materials, including the thickness and configuration of substrate layers, are designed to facilitate such continuous wear.

In some embodiments, the material of substrate layers acts as an electrostatic discharge (ESD) barrier to prevent arcing. The electrodes are attached to the bottom substrate by thermally cured glues such as polyurethane-based adhesive films and silver-loaded polyurethane-based adhesive pastes. This configuration always pushes out the electrodes towards the user's skin. This implementation is intended for better skin-electrode contact by compensating for different skin contours and holding the electrodes in place during any movement, including a change in posture, of the user.

In one embodiment, the top and bottom substrate layers may be made of an elastomeric compression fabric material. The elastic fabric may, for example, be polyester with LYCRA/spandex/elastane, nylon with LYCRA/spandex/elastane, cotton-poly rib, as well as other types of similar fabrics. The fabric may have a variety of different weaves such as plain, knitted or tricot. The elastomeric material may have a Shore 00 hardness of 30-50, and be made of neoprene, EPDM (ethylene propylene diene monomer), polyurethanes or other similar types of materials.

Figure 2D:
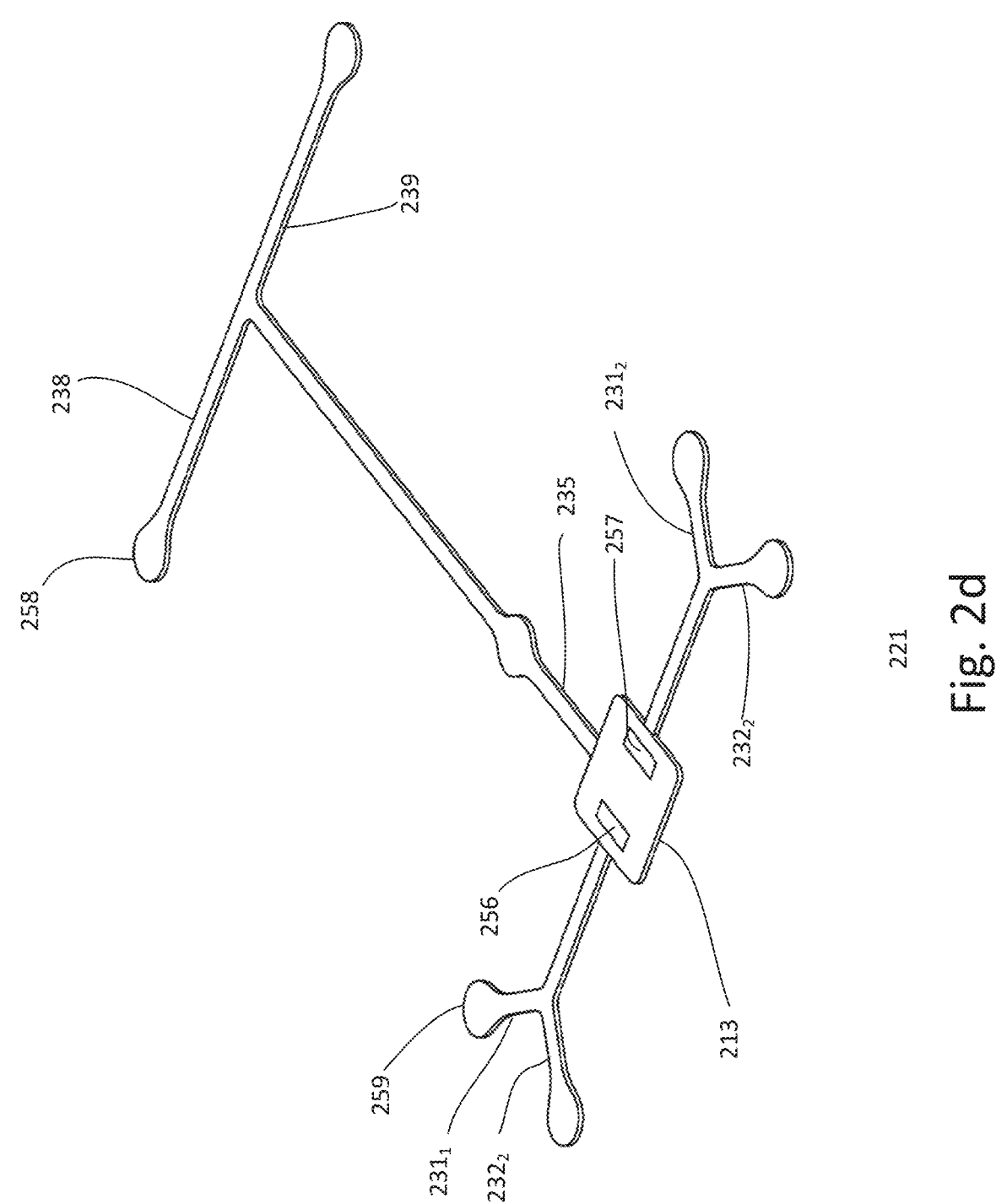
FIG. 2d shows an embodiment of a trace unit.

FIG. 2d shows an embodiment of a trace unit 221. The trace unit is a flexible trace unit with a plurality of electrode signal traces connected to the electrodes and pressure signal traces connected to flexible PCBs (or neck PCBs) on which the pressure sensor arrays are mounted. In addition, the trace unit includes electrode interfaces for the electrodes and pressure sensor interfaces for the neck PCBs mounting the pressure sensor arrays and the capacitance to digital converters. The trace unit is configured to fit within the footprints of the top and bottom substrate layers.

In one embodiment, the trace unit includes a first set of bioimpedance electrode signal traces $231_1$ and $232_1$ for the first set of bioimpedance electrodes, a second set of bioimpedance electrode signal traces $231_2$ and $232_2$ for the second set of bioimpedance electrodes, an RLD (Right Leg Drive) electrode signal trace 235 for the RLD electrode, and pressure signal traces 238 and 239 for the neck PCBs mounted with first and second pressure sensor arrays.

In one embodiment, each electrode signal trace includes an electrode interface portion 259. The interface portion is designed to accommodate an electrode. In one embodiment, the electrode interface portion includes an electrode interface and a bottom PCB circuit interface. The electrode interface, for example, is connected to an electrode. As for the bottom PCB circuit interface, it connects the electrode to the bottom PCB via the electrode interface. In one embodiment, bioimpedance electrodes have four conductive signal lines coupled to an analog front end, such as an AD5940 from Analog Devices or AFE4500 from Texas Instruments. For example, the input electrodes (I+ and I−) and output electrodes (V+ and V−) each have one signal line coupled to the analog frontend. In addition, each output electrode (V+ or V−) also has its signal line coupled to the ECG/EKG analog front end, such as an AD8232 or AD8233. As for the RLD electrode, one signal line is coupled to the ECG/EKG analog frontend. Other configurations of the signal traces of the electrodes may also be useful.

In one embodiment, each pressure signal trace includes a pressure sensor interface portion 258. The pressure sensor interface portion, in one embodiment, includes an interface between the pressure sensor array and a flexible printed circuit board (neck PCB) and an interface between a capacitance-to-digital converter (CDC) and the flexible printed circuit board. For example, the pressure sensor array is a flexible PCB-mounted pressure sensor array. In some embodiments, a wireless transmitter is included with the CDC to enable wireless transmission of data, such as carotid artery pressure waveform, from the pressure sensor array.

The electrode and pressure signal traces are connected to a bottom PCB 213. The bottom PCB includes PCB interface portions 256 and 257. The PCB interface portions accommodate connectors for connecting to the main PCB in the electronic housing.

The bottom PCB, in one embodiment, is in physical contact with the top substrate layer of the patch body. This enables electrical communication with the main PCB layer once the circuit connectors are assembled. With the electrode interface portions coming in contact with the electrodes, the electrode signal traces transmit bioimpedance and ECG/EKG (and/or other physiological data) from the electrodes to the main PCB in the electronic housing.

The material and thickness of electrode signal traces are selected to provide the desired combination of flexibility, durability and signal transmission. For example, electrode signal traces may include two layers. The first layer may be a top layer and the second layer may be a bottom layer, which is facing the user skin. The top layer may be made of a non-conductive textile material while the bottom layer may be made of conductive textile material, such as conductive Shieldex® "P130+B". The textile material may be a knitted fabric with about 22% elastomer, making it stretchable on two sides with an elongation warp of 155-205% and weft 85-125%.

In other embodiments, electrode signal traces may include a combination of silver (Ag) and silver chloride (AgCl). For example, electrode signal traces may include a top layer of silver, a middle layer of carbon-impregnated vinyl, and a bottom (patient-facing) layer of silver chloride. In another embodiment, both top and bottom layers of electrode signal traces may be made of silver chloride. In one embodiment, the top and bottom layers may be applied to the middle layer in the form of silver ink and silver chloride ink, respectively. In yet other embodiments, each electrode signal trace may include only two layers, such as a top layer of silver and a bottom layer of silver chloride.

In another embodiment, the material of a bottom layer of each electrode signal trace may be selected to match the chemistry of the hydrogel electrodes or to create a half-cell with the body of the subject. For example, the material of the bottom layer may be AgCl. In other embodiments, the material of a bottom layer of each electrode signal trace such as Shieldex® "P130+B", may be selected to match the chemistry of the conductive textile electrodes. Other types of electrode signal traces may also be useful.

In one embodiment, the thickness of the electrode signal traces may be selected to optimize desired properties. For example, at least one of the layers of electrode signal traces can be of a sufficient thickness to minimize or slow depletion of the material from an anode/cathode effect over time. Additionally, the thickness may be selected for desired flexibility, durability and/or signal transmission quality.

In one embodiment, the materials of the pressure signal traces may be similar to those described for the electrode signal traces. For example, pressure signal traces may include two layers. The first layer may be a top layer and the second layer may be a bottom layer, which is facing the user skin. The top layer may be made of a non-conductive textile material while the bottom layer may be made of conductive textile material. Alternatively, metal wiring such as copper wire may be employed for the bottom layer instead. Having other materials for the pressure signal traces may also be possible.

Figure 2E:
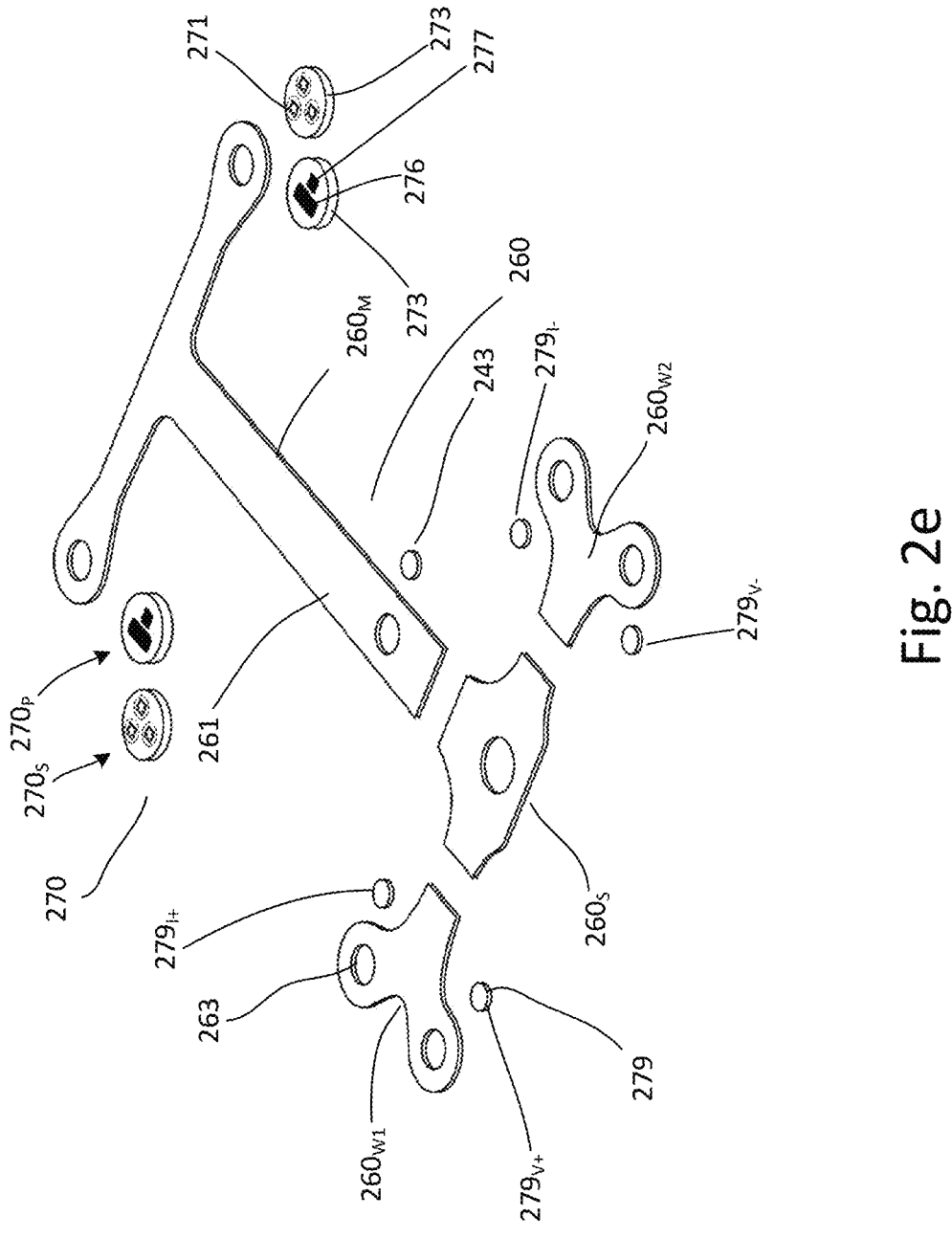
FIG. 2e shows an embodiment of an adhesive layer configured to accommodate electrodes and sensors.

FIG. 2e shows an embodiment of an adhesive layer 260 which is configured to accommodate electrodes and sensors which contact the user's skin. The adhesive layer is shown with the skin-facing surface 261. For example, the skin-facing surface is the surface which contacts the user's skin. The adhesive layer may be designed with a footprint or shape which is the same as the bottom substrate layer of the patch body. In some embodiments, such as in the case where the top substrate layer is slightly larger than the bottom substrate layer, the adhesive layer may be designed with a footprint which is the same as the top substrate layer.

As shown, the adhesive layer includes multiple adhesive layers. In one embodiment, the adhesive layer includes a main adhesive layer $260_M$, a first wing adhesive layer $260_{W1}$, a second wing adhesive layer $260_{W2}$ and a shoulder adhesive layer $260_S$. The various adhesive layers may be joined to form the footprint of the adhesive layer. In other embodiments, the adhesive layer is a single adhesive layer. Other configurations of the adhesive layer may also be useful. Although shown is a plurality of adhesive layers, the term adhesive layer may be used to refer to individual adhesive layers or the adhesive layer as a whole.

In one embodiment, the adhesive layer includes openings 263 for accommodating the electrodes and sensors. For example, the adhesive layer includes electrode openings for the bioimpedance electrodes 279 (I+, I−, V+ and V− electrodes $279_{I+}$, $279_{I-}$, $279_{V+}$ and $279_{V-}$), the RLD electrode 243 and sensor openings for the pressure sensor arrays 270 and the PPG sensor.

In one embodiment, the electrodes may be flexible electrodes. For example, the flexible electrodes are made of a flexible material. This improves overall conformability to the user's body. The flexible electrodes may be made of hydrogel. The hydrogel flexible electrodes provide conformal and non-irritating contact with the skin, enhancing the electrical connection with the skin while reducing motion artifacts. In some embodiments, the hydrogel electrodes may be punched into the adhesive layer, thereby forming the openings and filling them with the hydrogel electrodes.

In an alternative embodiment, electrodes and adhesive may be replaced with an adhesive layer made of a conductive material. In such cases, the entire adhesive layer on the underside of the bottom substrate layer acts as an electrode. Such an adhesive layer may include a hybrid adhesive/conductive substance or adhesive substance mixed with conductive elements or particles. In one embodiment, the hybrid adhesive layer may be a hybrid of a hydrogel and a hydrocolloid adhesive.

In another embodiment, the electrodes may be made of fabric, such as conductive Shieldex® "P130+B", a 2D stretchable synthetic wrap-knitted silver coated fabric, an intermediate 3 mm foam layer and snap buttons for electrical connection. The "P130+B" is made of 78% polyamide and 22% elastomer which is coated with 99% conductive silver particles with a surface resistivity of about p<2 Ω/sq.

In one embodiment, the pressure sensor arrays 270 include MEMS-based pressure sensor arrays. Other types of pressure sensors may also be provided. Skin-side and patch-side views $270_S$ and $270_P$ of the pressure sensor arrays are shown. A pressure sensor array 270, in one embodiment, includes pressure sensors 271 mounted on a flexible PCB (or neck PCB) 273. The pressure sensors are mounted on the skin side of the neck PCB. As shown, the sensor array includes 3 pressure sensors mounted on the neck PCB. Providing other numbers of pressure sensors may also be useful. On the patch side of the PCB, in one embodiment, a CDC 276 and a wireless transmitter module 277 are mounted. The CDC 276, for example, is connected to the sensor interface portion of the trace unit. This enables power to be provided to the CDC from the power supply in the main PCB.

Figure 2F:
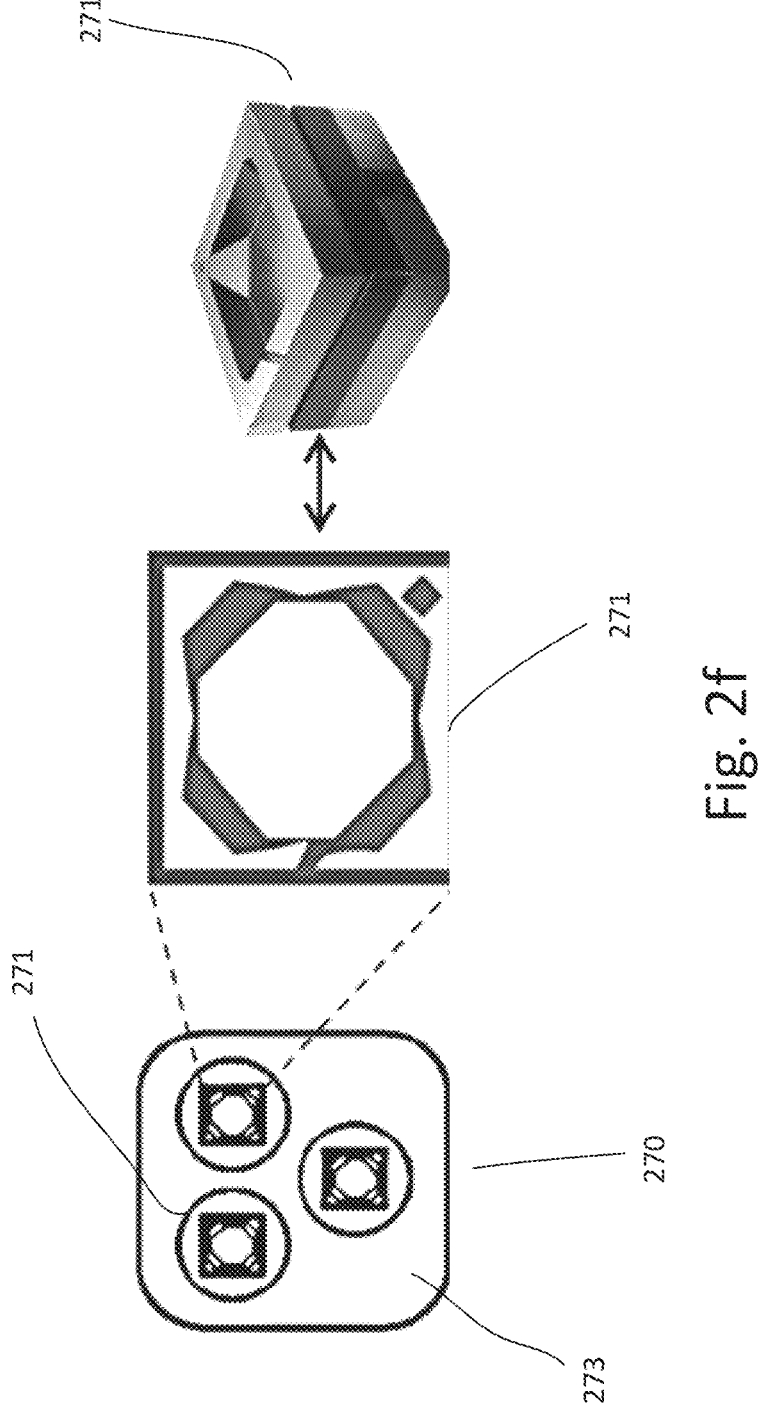
FIG. 2f shows an embodiment of a pressure sensor array.

Referring to FIG. 2f, a pressure sensor array 270 with a plurality of pressure sensors 271 is shown. The pressure sensor array, as shown, includes three pressure sensors. Providing other numbers of pressure sensors for the sensor array may also be useful. The pressure sensors, in one embodiment, are mounted onto a flexible PCB 273. The pressure sensors, for example, may be MEMS-based pressure sensors, such as SCB10H sensors from Murata. Other types of pressure sensors, such as piezoresistive pressure sensors, may also be useful.

Figure 2G:
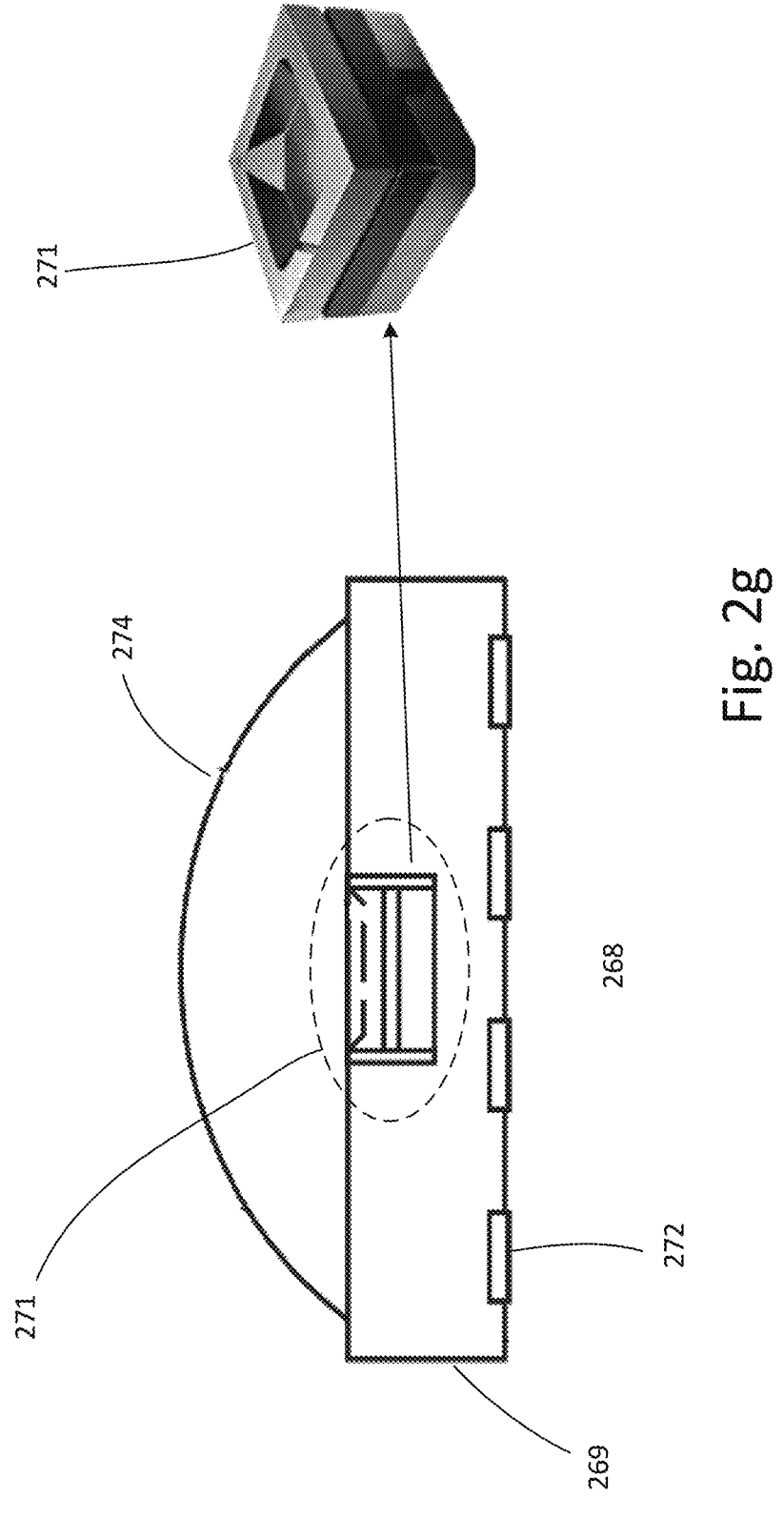
FIG. 2g shows an embodiment of a pressure sensor package.

In FIG. 2g, an embodiment of a pressure sensor package 268 is shown. The pressure sensor package, for example, is a MEMS-based capacitive sensor package. The pressure sensor package includes a pressure sensor 271 mounted on a package substrate. The package substrate and the pressure sensor may be encapsulated by a mold compound 269. The package substrate may include package contact pads 272 which are electrically connected to terminals of the pressure sensor, for example, by wire bonds. A pressure-sensitive surface of the pressure sensor is exposed by the mold compound. A silicone gel bulb 274 covers the package surface with the exposed pressure-sensitive surface (e.g., diaphragm) of the pressure sensor. The pressure waves associated with the blood flowing through the common carotid artery appear as mechanically induced changes in capacitance, enabling pressure to be measured.

Figure 2H:
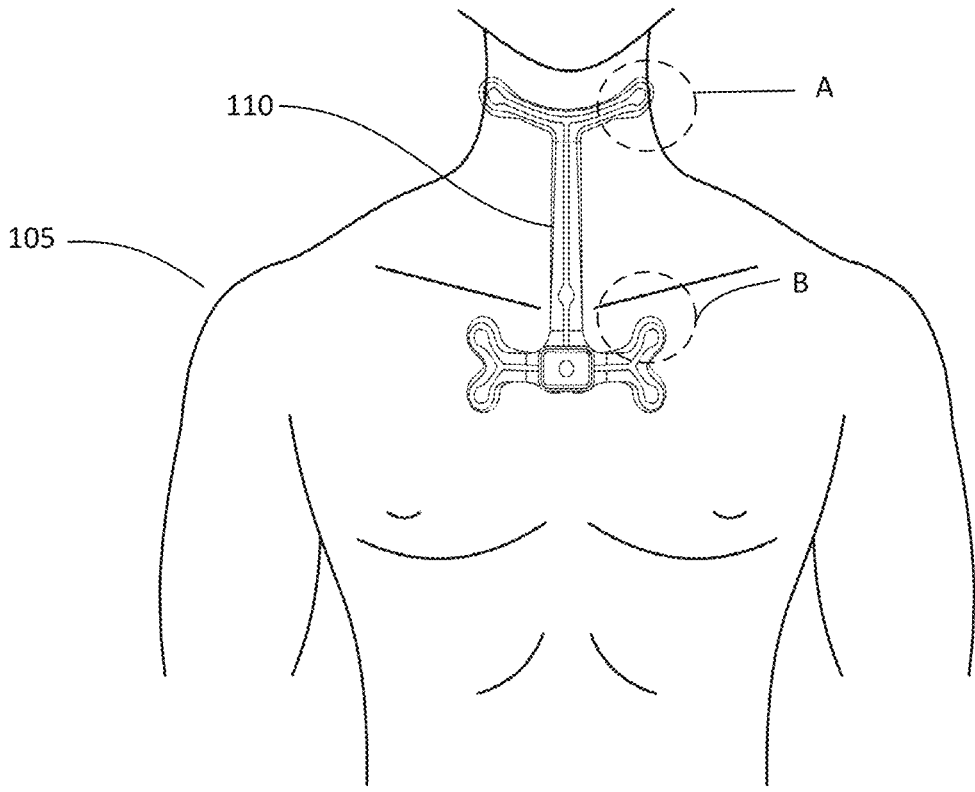

Referring to FIG. 2h, a user 105 is shown wearing an embodiment of a wearable monitoring device 110 for monitoring HF. The monitoring device includes pressure sensor arrays for measuring the arterial pressure waveform of the user from the common carotid arteries (indicated by region A), conductive bioimpedance electrodes for current injection and voltage detection (indicated by region B) and an RLD electrode for detecting ECG/EKG right leg drive $V_{RLD}$. The monitoring device may also include an optical sensor system along with a plurality of photodiodes and LED(s) for measuring photoplethysmography waveform from the midsternal region of the user's chest.

FIG. 2i1 shows region A of one embodiment of the monitoring device in greater detail. As shown, region A includes a pressure sensor array 270. The pressure sensor array, as shown, includes pressure sensor packages 268, such as those described in FIG. 2g, mounted on a flexible PCB 273. As shown, the pressure sensor array includes three pressure sensor packages, each with a pressure sensor. The pressure sensor packages contact the skin of the user at region A, which is the location of the user's carotid artery. The patch side of the PCB includes a CDC 276 and a wireless transmitter 277 and contacts the patch 110.

The MEMS pressure sensor element may include two silicon wafers and one glass wafer bonded together by anodic bonding. The other silicon wafer forms a diaphragm. The diaphragm bends as a function of outer pressure inducing a force $F=(p_1-p_2)\times A$. The sealed gap between the static electrode and diaphragm contains argon gas at reference pressure $p_2$. The force F is proportional to the bending of the diaphragm, and hence to the capacitance between the electrodes ($C=\varepsilon_r A/d$, where $\varepsilon_r$=dielectric constant, d=distance between the electrodes). The capacitance is modeled with a simplified parallel plate model $$C(p)=C_{00}+C_0/(1-p/p_0)$$

where, $C_{00}$ is stray capacitance of the sensor, $C_0$ is proportional to the inverse of distance between parallel plate electrodes and $p_0$ is the pressure where electrodes touch each other.

The pressure F exerted by the blood flowing through the common carotid artery onto the gel bulb is imparted to the pressure-sensitive surface of the pressure sensors, enabling the pressure pulse wave (PPW) to be measured. Attaching the patch body with the pressure sensors above the aortic arch enables pulse waves to be measured when the carotid artery is being pushed between a pressure sensor and the neck. For example, the force exerted on the pressure sensor creates a displacement in the silicone gel bulb of the sensor package towards a diaphragm of the pressure sensor, causing it to bend and simultaneously change its capacitance. As a result, the dilating artery creates a pressure signal which changes the capacitance of the sensor and the arterial pulse waves can be recorded continuously.

FIG. 2i2 shows region A of another embodiment of the monitoring device in greater detail. In one embodiment, region A includes a piezoresistive pressure sensor 271, such as a self-powered PPNWF pressure sensor. As shown, the piezoresistive pressure sensor is formed from a double-layered nanofiber woven fabric 280, such as PEDOT@PVDF. A close-up of the nanofiber woven fabric is shown. The PEDOT@PVDF is sandwiched by top and bottom PDMS films $281_T$ and $281_B$. The PDMS films may be attached to the nanofiber woven fabric by glue. In addition, copper wires 283 may be attached to both the upper and lower surfaces of the double-layered fabric. The PDMS films are gradually cured. After curing, the copper wires tightly attached the nanofiber fabric layer to the PDMS films. Similar to the MEMS-based capacitive pressure sensor, the PPNWF pressure sensor may also include, for example, an Analog-to-Digital Converter (ADC) to convert an analog signal to a digital signal and a wireless transmitter, such as a low-energy Bluetooth or, an Electro-Quasistatic human body communication (EQS-HBC) module, for transmitting converted digital signals to the main PCB. Other techniques for transmitting the signals of the pressure sensor including using digital peripherals attached to the ADC may also be possible.

A piezoresistive sensor detects various tactile stimuli through the change of electrical resistance and the change of contact resistance between conducting materials. The pressure sensitivity S of the PPNWF pressure sensor is defined as:

$$S=(\Delta I/I_0)/\Delta P,$$

where, $\Delta I$ is the pressure-induced change in current, $I_0$ is the initial current of the PPNWF pressure sensor without pressure loading, and $\Delta P$ is the change in applied pressure.

According to an embodiment, the relative change in current of the PPNWF pressure sensor against applied pressure exhibited a linear relation even at a relatively low-pressure range (~100 Pa) with sensitivity up to 18.4 $kPa^{-1}$, and the sensitivity decreased to 0.7 $kPa^{-1}$ at a relatively high-pressure range.

The PPNWF pressure sensor has been demonstrated to have ultra-high sensitivity. The enhanced sensitivity of the PPNWF pressure sensor may be attributed to the drastic change in contact area under low pressure. The accumulation of nanofibers, which are much higher in number compared to the filaments, deforms easily with massive protuberances of the PEDOT nanoparticles, resulting in a significant increase of contact joints and the total contact area under subtle stress. As such, PPNWF sensors may have an ultra-high sensitivity.

The PPNWF pressure sensor exhibits changes in resistance and voltage under applied pressure. Simultaneous changes in voltage and resistance caused the PPNWF pressure sensor to have pressure sensitivity so that the sensor also exhibits piezoelectricity in addition to piezoresistivity. The total changes in current of the PPNWF pressure sensor under applied pressure can be shown as:

$$\Delta I/I_0=\{1+(U'/U_0)\}/\{1-(R'/R_0)\},$$

where $U_0$ is the working voltage of 1 V,

U' is the open-circuit voltage generated by the sensor under applied pressure (mV), $R_0$ is the initial resistance of the sensor without pressure loading ($\Omega$), and R' is the resistance under applied pressure ($\Omega$).

According to some embodiments, the applied pressure could lead to changes in voltage and resistance at the same time. However, changes in voltage and resistances do not affect each other. Moreover, the pressure sensitivity caused by piezoelectricity is poorer compared to the piezoresistive pressure sensitivity. This is because the change in voltage is lower than the change in resistance. The PPNWF pressure sensor can generate a weak open-circuit voltage signal under applied pressure while having a large change in resistance owing to the multi-level hierarchical structure of the PPNWF sensor. Therefore, the high-pressure sensitivity of the sensor is mainly caused by the change in resistance.

Figure 2J:
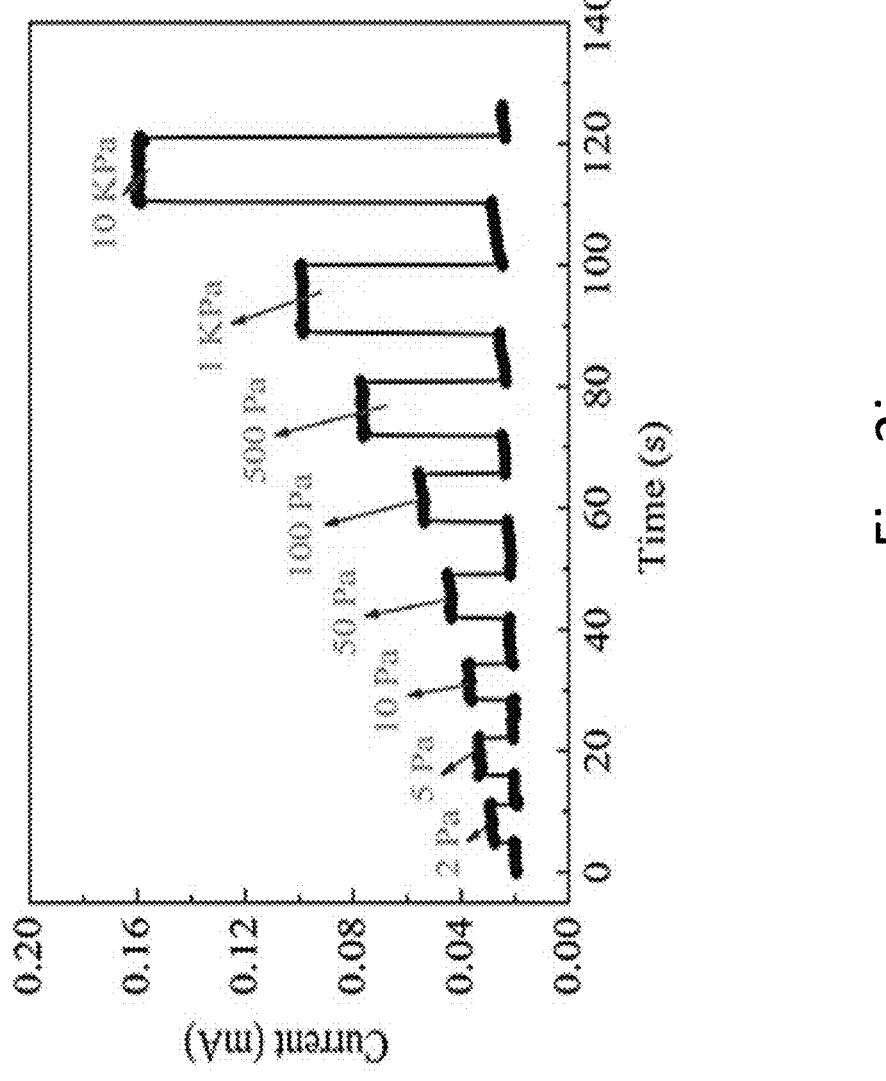

FIG. 2j is a graph showing the dynamic instantaneous current response to varying pressure by the piezoresistive pressure sensor. As illustrated, the piezoresistive pressure sensor has ultra-high sensitivity to changes in pressure.

According to another embodiment, the pressure sensor may include a frequency modulated millimeter-wave (FMCW) radar device that operates by transmitting a millimeter-wave signal towards the skin surface of a user and by receiving a reflected signal dataset. The large dielectric constant between air and skin at millimeter-wave frequencies, for example, creates a relative permittivity of 8 and conductivity of 36 S/m at 60 GHz for the skin. This results in the skin being highly reflective, with 38% of power reflected at the interface for a plane wave with perpendicular incidence. Therefore, a millimeter-wave signal transmitted towards the skin surface undergoes a significant amount of reflection as it strikes the skin. As a result, any small perturbation of the skin due to pulsatile motion can be detected by characterizing this reflected energy. While other radar architectures are also feasible, FMCW typically allows for a good balance between signal-to-noise ratio (SNR) and range resolution that is well suited for sensing hemodynamic waveforms. A FMCW device may be positioned on the common carotid artery of the user for transmitting pulse signals toward the target artery and receiving reflected signals. In one embodiment, the FMCW radar sensor on a single chip module is an AWR1642 IC from Texas Instruments, USA, capable of operation in the 76 to 81 GHz band. Other types of single-chip FMCW modules such as BGT60TR24B from Infineon Technologies AG, Munich, Germany may also be useful.

Other configurations of the pressure sensors to measure subtle changes in arterial pressure on the common carotid artery may include an inorganic ferroelectric/piezoelectric material such as lead zirconate titanate or, Pb $[Zr_xTi_{1-x}]O_3$, $0 \leq x \leq 1$ (commonly referred as PZT), on a flexible and stretchable substrate that provides a high level of pressure sensitivity (~0.005 Pa), fast response (~0.1 milliseconds), low hysteresis, superior operational stability and excellent fatigue properties. Ultrathin sheets of high-quality PZT may serve as the active components of capacitor-type structures that connect to the gate electrodes of MOSFETs based on nanomembranes of silicon (SiNMs). Specifically, a SiNM n-channel MOSFET amplifies the piezoelectric voltage response of the PZT and converts it to a current output via capacitance coupling. Other ferroelectric/piezoelectric materials may include, but not limited to barium titanate ($BaTiO_3$), lead titanate ($PbTiO_3$), potassium niobate ($KNbO_3$), lithium niobate ($LiNbO_3$), lithium tantalate ($LiTaO_3$), sodium tungstate ($Na_2WO_3$), zinc oxide (ZnO), $Ba_2NaNb_5O_5$, $Pb_2KNb_5O_{15}$, sodium potassium niobate ((K, Na)$NbO_3$), bismuth ferrite ($BiFeO_3$), Sodium niobate ($NaNbO_3$), bismuth titanate ($Bi_4Ti_3O_{12}$), sodium bismuth titanate ($Na_{0.5}Bi_{0.5}TiO_3$), polyvinylidene fluoride (PVDF) and poly[(vinylidenefluoride-co-trifluoroethylene] ([P (VDF-TrFE). The flexible substrate may be chosen from a group of energy-harvesting materials such as polyurethanes, silicon rubber, polyethers, polyesters, co-polymers of polyether urethanes, polyester urethanes, polysulfones, polybutadiene-styrene, elastomers, hydrogels formed from copolymers of polyethylene glycol and polylactide, polyglycolide or copolymers of polylactide-co-glycolide polyacrylate rubber, ethylene-acrylate rubber, polyester urethane, bromo isobutylene isoprene, polybutadiene, chloro isobutylene isoprene, polychloroprene, chlorosulphonated polyethylene, epichlorohydrin, ethylene propylene, ethylene propylene diene monomer, polyether urethane, perfluorocarbon rubber, fluorinated hydrocarbon, fluorosilicone, fluorocarbon rubber, hydrogenated nitrile butadiene, polyisoprene, isobutylene isoprene butyl, acrylonitrile butadiene, polyurethane, styrene butadiene, styrene ethylene butylene styrene copolymer, polysiloxane, vinyl methyl silicone, acrylonitrile butadiene carboxy monomer, styrene butadiene carboxy monomer, thermoplastic polyether-ester, styrene butadiene block copolymer, styrene butadiene carboxy block copolymer, synthetic polyisoprene, polybutadiene, chloroprene rubber, polychloroprene, neoprene, baypren, butyl rubber, halogenated butyl rubbers, styrene-butadiene Rubber, nitrile rubber, hydrogenated nitrile rubber, ethylene propylene rubber, ethylene propylene diene rubber, epichlorohydrin rubber polyacrylic rubber, silicone rubber, fluorosilicone rubber, fluorosilicone rubber, fluroelastomers viton, tecnoflon, fluorel, aflas and dai-el, perfluoroelastomers tecnoflon PFR, kalrez, chemraz, perlast, polyether block amides, chlorosulfonated polyethylene, hypalon, ethylene-vinyl acetate, and combinations thereof.

The complete carotid artery pulse pressure waveform provides valuable information for diagnostics and therapy of cardiovascular diseases, such as arteriosclerosis, hypertension and left ventricular systolic and diastolic dysfunction.

Many hemodynamic parameters such as arterial index, upstroke time, stroke volume variation and cardiac output can be directly calculated or estimated in real-time from the carotid artery pressure waveforms. Skin-mounted sensors provide a promising path toward long-term diagnostics based on this measurement.

Figure 2K:
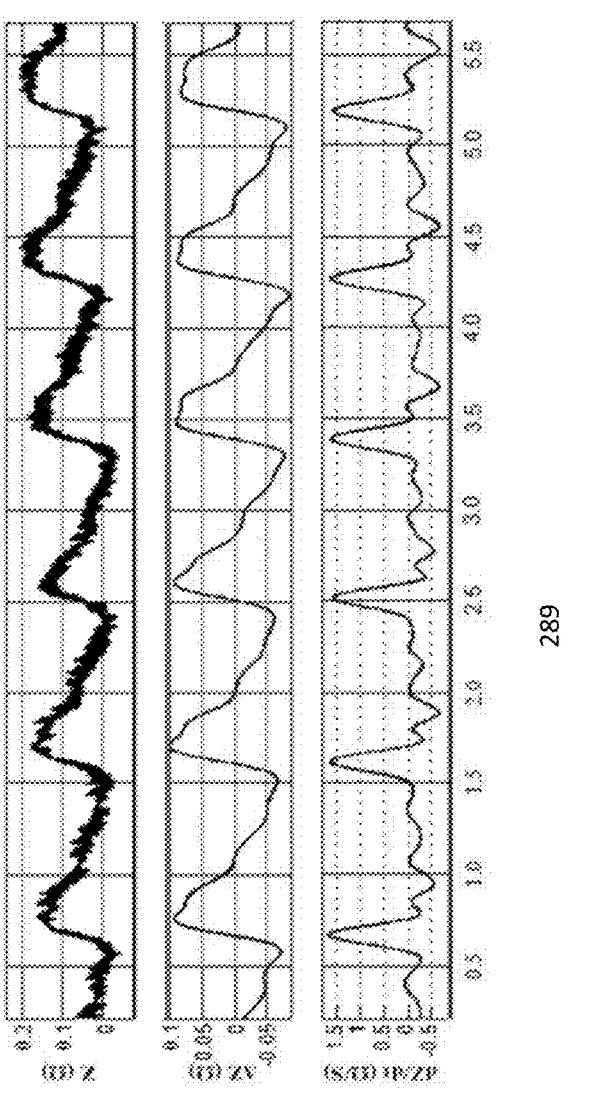
Figure 2K:
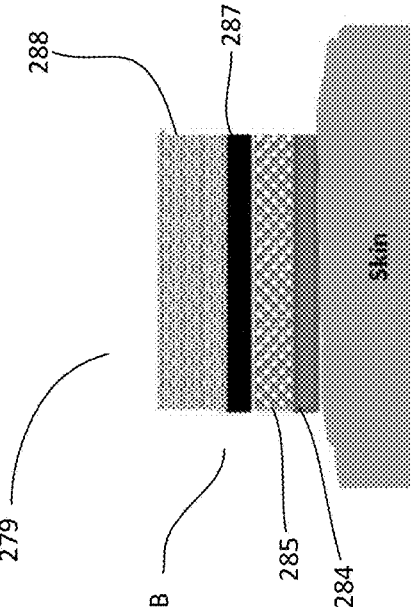

FIG. 2k shows region B of the monitoring device in greater detail. In one embodiment, region B includes a bioimpedance conductive electrode 279. The bioimpedance electrode in region B is, for example, a current electrode configured to inject a high-frequency, low-amperage current ($I_1$) into the user's thoracic region. This serves as a current source. Typically, a current pump provides the modulated current, with the modulation frequency typically being between about 40-150 kHz having a current magnitude being between about 70 µA to 100 µA. Preferably, the current source supplies an AC current with a magnitude of ~80 µA that is modulated at 100 kHz through the first electrode (or textrode) embedded (e.g., woven or embroidered) in the wearable patch.

The electrode, in one embodiment, is a flexible dry electrode, such as a textile electrode. In one embodiment, the electrode includes multiple flexible layers. In one embodiment, the electrode includes a bottom layer 284 which is an elastic conductive coating which contacts the skin. A conductive fabric layer 285, such as conductive Shieldex® "P130+B", is disposed above the elastic conductive coating. A barrier layer 287 is disposed above the conductive fabric layer. The barrier layer serves as a humidity barrier. A support layer 288 is disposed above the barrier layer. The support layer, for example, is a foam layer to improve the pressure distribution of the electrode to the skin, improving skin-electrode contact.

A second conductive textile electrode located in the opposing wing extension injects an identical current (e.g., $I_2$) that is out-of-phase from $I_1$ by 180°. The first and second bioimpedance electrodes may serve as input electrodes located on opposing wing extensions. The current generator may provide a square-wave modulating differential current that is AC injected into the body with the bio-impedance sensed differentially through voltage-detecting electrodes. For example, third and fourth electrodes are the voltage electrodes provided in wing extensions below the current electrodes and serve as output bioimpedance electrodes. The electrodes of the wearable device may be the same type of electrodes. Providing different types of electrodes for the wearable device may also be useful.

The voltage levels at the voltage electrodes are indicated in a bioimpedance graph 289 as $V_1$ and $V_2$. The graph charts Z, $\Delta Z$ and dZ/dt as a function of time. For example, using Ohm's law (Z=dV/dI, where $dV=V_1-V_2$ and $dI=I_1-I_2$), differential of the measured voltage with respect to the magnitude of the injected current yields a time-dependent conductance Z that relates to the blood flow through the aorta. This time-dependent impedance features a slowly varying dc offset, characterized by $Z_0$, that indicates the baseline impedance encountered by the injected current, depending on, for example, the amount of fat, muscle mass, bone density, and the blood volume in the thoracic region of a given patient. $Z_0$, which may have a typical value between about 10Ω and 50Ω, and is influenced by processes such as respiration, motion impedance and movement sensing, which is attributed to the parasitic capacitances that exist in the measurement setup.

Although the wearable device is described as having a single patch body, it is understood that the wearable device may include a multi-portion patch body. For example, the wearable device may include a patch body having multiple distinct body portions. Different portions may include their respective power source and communicate wirelessly. In some embodiments, the multi-portion patch body of the wearable device may include two patch body portions. For example, the central body member, extensions and wing extensions are arranged to form two patch body portions. In one embodiment, a first end portion of the central body member with the extensions forms a single neck patch body portion and a second end portion of the central body member with the wing extensions forms a distinct chest patch body portion. In one embodiment, the main PCB is part of the chest patch body portion and a separate battery module is provided in the neck patch body portion for powering the sensors of the neck patch body portion. Data from the sensors of the neck patch body portion is communicated to the main PCB wirelessly. Providing distinct patch body portions advantageously enables the patch body portions to be worn separately by a patient. For example, the neck patch body portion which accommodates the pressure sensor arrays may be worn by the patient a few times a day to measure pressure pulse waveforms. As for the chest patch body portion with the electrodes, it may be worn continuously by the patient on the midsternal line to measure ECG and thoracic bioimpedance waveforms. Having other numbers of the patch body portions or configurations of the wearable device may also be useful.

In yet another embodiment, the central body member, extensions and wing extensions are arranged to form three patch body portions. For example, a first end portion of the central body member with the extensions forms distinct left and right neck patch body portions. The left neck patch body portion includes the left pressure sensor array configured to be disposed on the left common carotid artery while the right neck patch body portion includes the right pressure sensor array configured to be disposed on the right common carotid artery. As for the second end portion of the central body member with the wing extensions, it forms a distinct chest patch body portion. The main PCB is included on the chest patch body portion. Separate battery modules are included in the left and right neck patch body portions for operating the sensors. The left and right neck patch body portions, in one embodiment, are configured to transmit the pressure sensor data to the main PCB via wireless communication modules, such as via BLE or EQS-HBC modules. The neck and chest patch body portions can be worn separately by a patient. For example, the neck patch body portions which accommodate the pressure sensor arrays may be worn by the patient a few times a day to measure pressure pulse waveforms. As for the chest patch body portion with the electrodes, it may be worn continuously by the patient on the midsternal line for continuous measurement of ECG and thoracic bioimpedance waveforms. Other configurations of wearing the patch body portions may also be useful.

Figure 3A:
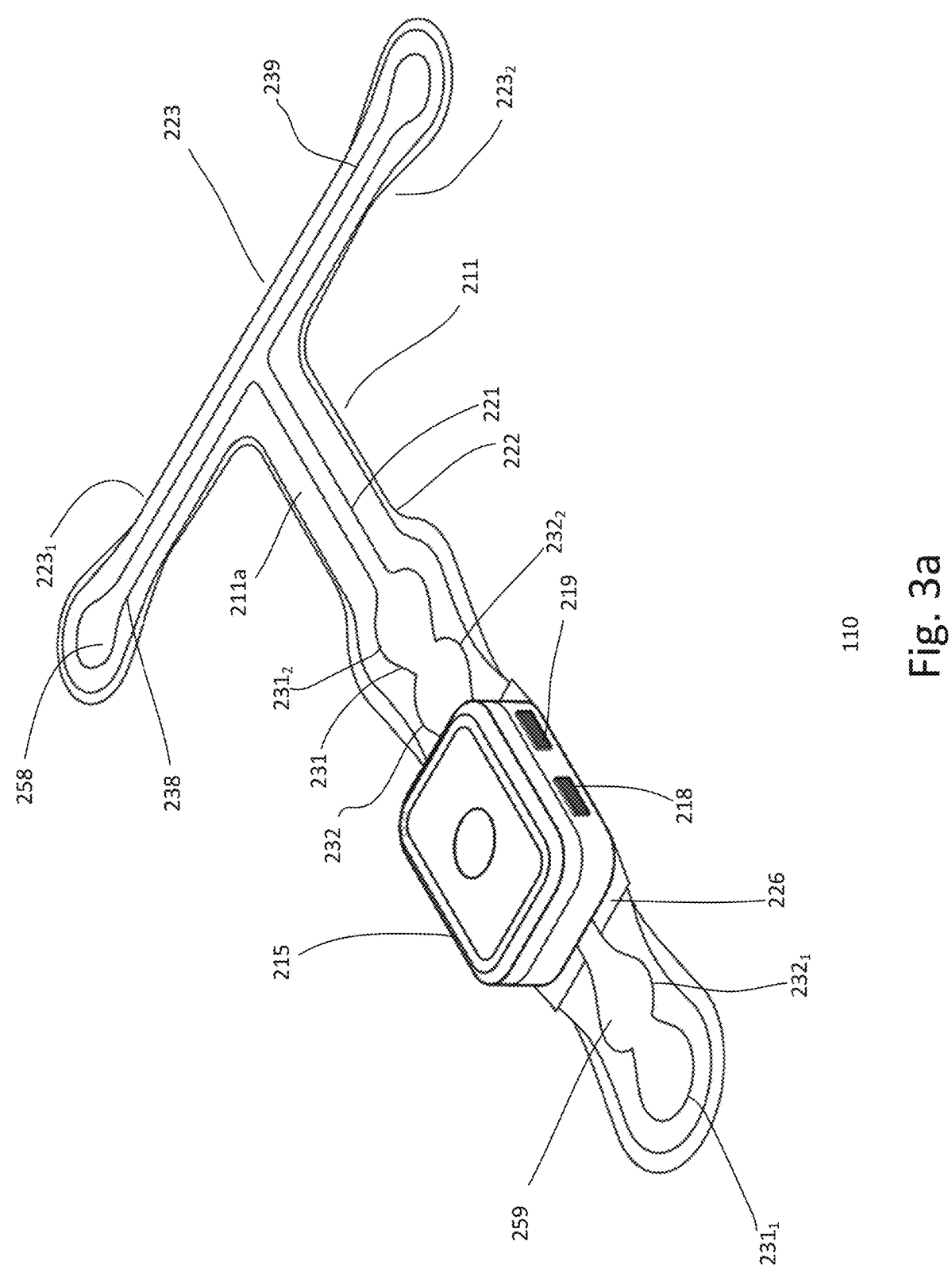
FIGS. 3a-3c show various views of an embodiment of a wearable monitoring device.
Figure 3B:
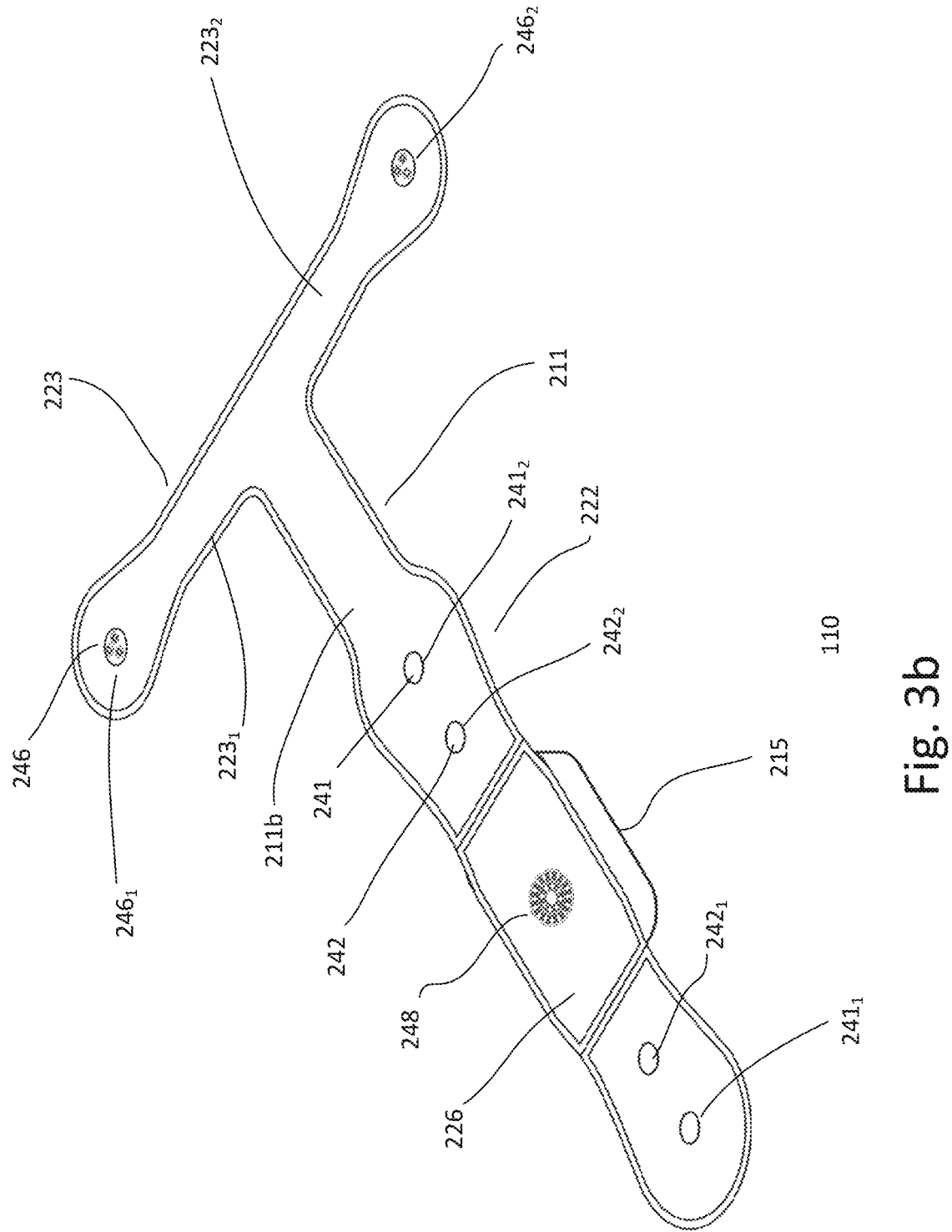
Figure 3C:
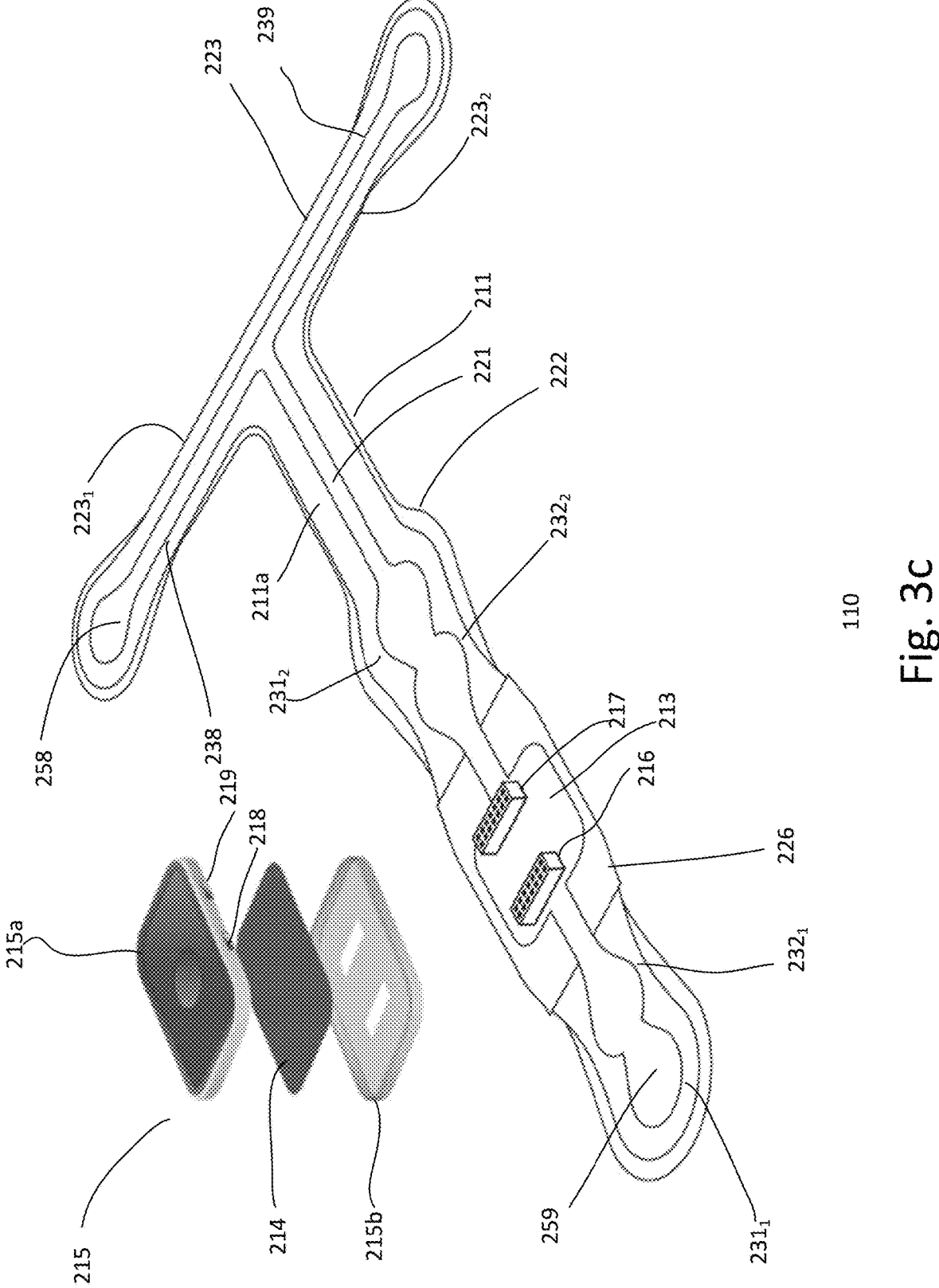

FIGS. 3a-3c shows various views of another embodiment of a wearable device 110. In particular, FIG. 3a shows a 3D front perspective view, FIG. 3b shows a 3D back perspective view skin side and FIG. 3c shows a 3D exploded front perspective view. As shown, the wearable device is a patch which includes various components for monitoring HF events in a user. The wearable device 110 is similar to that described in FIGS. 2a-2c. Common elements may not be described or described in detail.

In one embodiment, the wearable device includes a flexible patch body 211. The flexible patch body conforms to the body contour of the user when worn. The flexible patch body includes front and back patch body surfaces 211a and 211b.

The back patch body surface contacts the skin of the user. The back body surface includes an adhesive layer for attaching to the user's skin.

In one embodiment, the flexible patch body is formed from multiple layers. In one embodiment, the flexible patch body includes upper and lower substrate layers sandwiching the signal trace unit. For example, the signal trace unit is embedded between the top and bottom substrate layers. The top substrate layer may serve as the front patch surface and the bottom substrate layer may serve as the back patch surface.

In one embodiment, the flexible patch body includes an elongated central body member 222 having first and second central member ends. The flexible patch body includes first extensions 223 extending laterally from about the first end of the central body member. For example, the first extensions include a first extension portion $223_1$ extending from the central body member in a first lateral direction and a second extension portion $223_2$ extending from the central body member in a second lateral direction, which is opposite the first lateral direction. This forms, for example, a T-shaped upper portion of the patch body at the first end of the central body member. Unlike the flexible patch body of FIGS. 2a-2c, no wing extensions are provided at the second end of the central body member.

The flexible patch body includes a trace unit 221 which includes electronic traces or conductive wires. The trace unit, for example, is a flexible trace unit. The flexible trace unit, for example, is disposed between the top and bottom substrate layers of the flexible patch body. The trace unit includes pressure sensor interfaces 258 and electrode interfaces 259 for connecting to the neck PCBs mounting first and second pressure sensor arrays or pressure sensors 246 and electrodes 241 and 242. The term pressure sensor may refer to a pressure sensor or a pressure sensor array. The pressure sensors and electrodes are disposed on the back surface of the patch to enable contact with the user's skin. However, unlike the patch body of FIGS. 2a-2c, there is no RLD electrode. Instead, the RLD input of the ECG analog frontend, such as the AD8233/AD8382, is connected to the ground terminal of the main PCB. As such, no separate RLD electrode is needed. The electrodes may be dry electrodes and the pressure sensors may be MEMS-based capacitive pressure sensors or fabric pressure sensors, as previously described. Other types of electrodes or pressure sensors may also be useful.

The trace unit includes a bottom PCB 213 and main PCB connectors 216 and 217. Electrode signal traces $231_{1-2}$ and $232_{1-2}$ connect electrodes to the bottom PCB and signal traces 238 and 239 for the neck PCBs mounting first and second pressure sensors or pressure sensor arrays 246 to the bottom PCB. For example, a first set of electrode signal traces $231_1$ and $232_1$ connects a first set of bioimpedance electrodes $241_1$ and $242_1$ to the bottom PCB and a second set of electrode signal traces $231_2$ and $232_2$ connects a second set of bioimpedance electrodes $241_2$ and $242_2$ to the bottom PCB. A first signal trace 238 connects a neck PCB mounting the first pressure sensor $246_1$ to the bottom PCB and a second signal trace 239 connects a neck PCB mounting the second pressure sensor $246_2$ to the bottom PCB.

In one embodiment, a positive current (I+) is injected into the user's chest through the first electrode $241_1$ of the first set of bioimpedance electrodes and a positive voltage (V+) is measured at the second electrode $242_1$ of the first set of bioimpedance electrodes; a negative current (I−) is injected through the first electrode $241_2$ of the second set of bioimpedance electrodes and a negative voltage (V−) is measured at the second electrode $242_2$ of the second set of bioimpedance electrodes. For example, the current electrodes (I+ and I− electrodes) $241_{1-2}$ serve as input electrodes and the voltage electrodes (V+ and V− electrodes) $242_{1-2}$ serve as output electrodes. The voltage electrodes of the first and second sets of bioimpedance electrodes are configured to measure both ECG/EKG waveforms and bioimpedance waveforms. As shown, the I+ electrode is disposed below the V+ electrode and the I− electrode is disposed above the V− electrode. Other configurations of the electrodes may also be useful.

A rigid electronic housing 215 which houses a main PCB circuit board 214 is disposed on the front patch body surface of the shoulder portion of the central body member between the first and second sets of bioimpedance electrodes. In one embodiment, the electronic housing includes top and bottom housing parts 215*a-b* encasing the main PCB circuit board.

In one embodiment, B-to-B connectors are employed to connect the main PCB to the bottom PCB. This enables signals from the bioimpedance electrodes from the bottom PCB to be pre-processed by the main PCB and transmitted to, for example, the user's mobile device for further transmission of the pre-processed data to the server for processing. As for data from the pressure sensors, it can be transferred directly to the main PCB through the wireless communication module. In the case that wireless communication is not available, the pressure sensor data may be transferred by, for example, digital peripherals such as SPI/I2C/GPIO/UART interfaces from the flexible PCB (neck PCB) to the bottom PCB and then via the B-to-B connectors to the microcontroller in the main PCB.

The electronic housing also includes an on-off switch 218 for switching on the wearable device to collect and transmit data as well as a charge port 219. The charge port, for example, may be a USB port. The charge port is used to charge a battery disposed in the electronic housing for operating the patch.

In one embodiment, a PPG sensor 248 is disposed on the back patch body surface in the shoulder portion of the central body member. The PPG sensor, for example, is coupled to the bottom PCB. The PPG sensor, for example, is an optical sensor system along with a plurality of photodiodes and one or more light-emitting diodes (LEDs) for detecting the PPG signal. Similar to the pressure sensor data, data from the PPG sensor is transferred directly to the main PCB through the wireless communication module. Alternatively, it can be sent first to the bottom PCB by digital peripherals before it is transmitted via the B-to-B connector to the microcontroller in the main PCB.

Figure 3D:
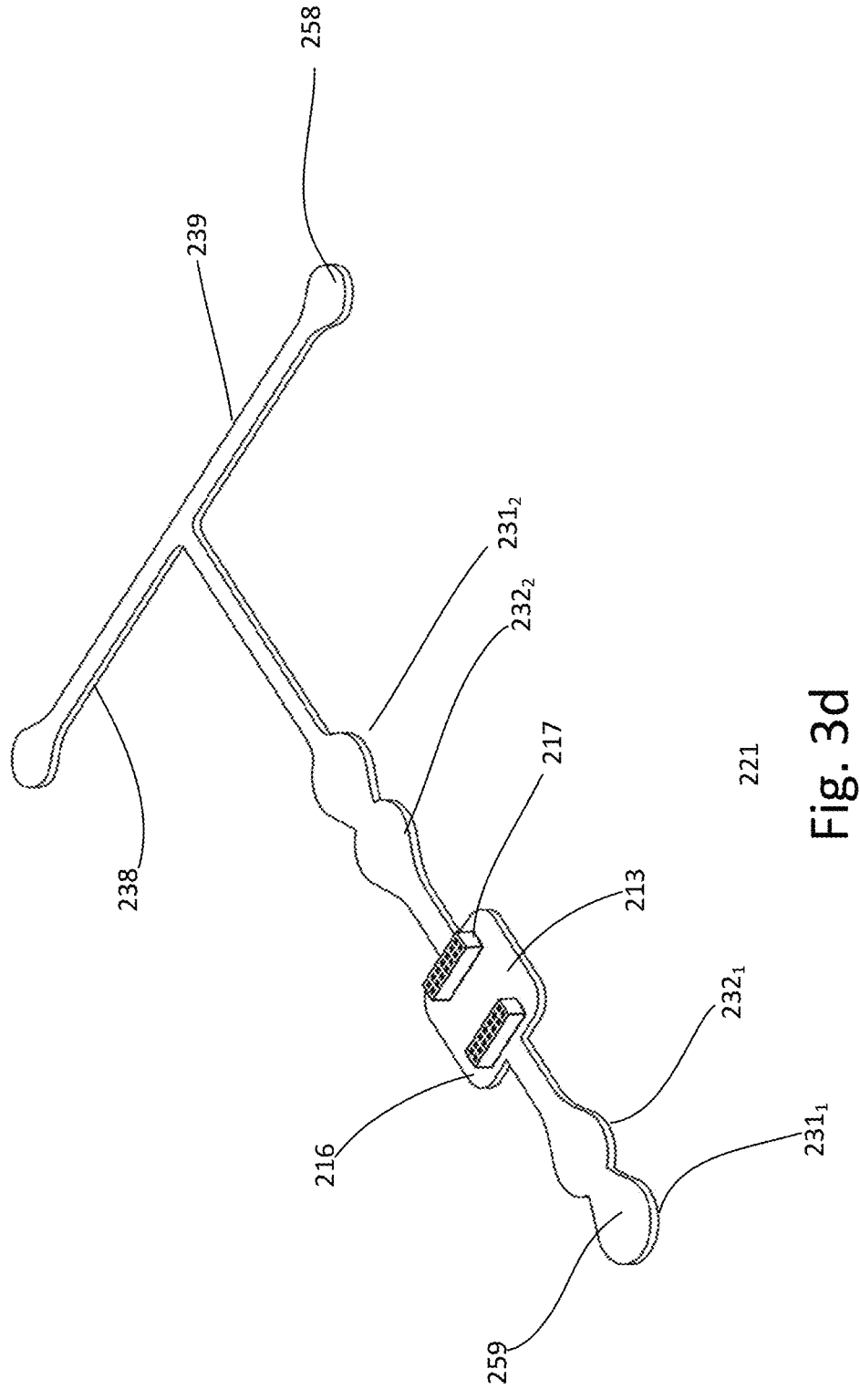
FIG. 3d shows another embodiment of a trace unit.

FIG. 3*d* shows another embodiment of a trace unit 221. The trace unit is similar to the trace unit described in FIG. 2*d*. Common elements may not be described or described in detail. The trace unit is a flexible trace unit configured to fit between the top and bottom substrate layers of the flexible patch body of the monitoring device of FIGS. 3*a*-3*c*.

As shown, the trace unit is a T-shaped trace unit with electrode signal traces connected to the electrodes and pressure signal traces connected to the flexible PCBs (neck PCBs) mounting the first and the second pressure sensor arrays. In addition, the trace unit includes electrode interfaces for the electrodes and pressure sensor interfaces for the neck PCBs mounting the pressure sensor arrays. The trace unit is configured to fit within the footprints of the top and bottom substrate layers.

In one embodiment, the trace unit includes a first set of bioimpedance electrode signal traces $231_1$ and $232_1$ for the first set of bioimpedance electrodes, a second set of bioimpedance electrode signal traces $231_2$ and $232_2$ for the second set of bioimpedance electrodes, first and second pressure signal traces 238 and 239 for first and second pressure sensor arrays. As discussed, the signal traces may include different numbers of signal lines (including power signals, such as voltage or voltages and ground). The number of signal lines for the signal traces, for example, may depend on the types and configurations of the electrodes and sensors. Each electrode signal trace includes an electrode interface portion 259 for accommodating an electrode and each pressure signal trace includes a pressure sensor interface portion 258 for accommodating a neck PCB mounting a pressure sensor array with a CDC and a wireless transmitter module. The electrode and pressure signal traces are connected to a bottom PCB 213. The bottom PCB includes PCB interface portions fitted with connectors 216 and 217 for connecting to the main PCB in the electronic housing.

The bottom PCB, in one embodiment, is in physical contact with the top substrate layer of the patch body. This enables electrical communication with the main PCB layer once the circuit connectors are assembled. With the electrode interface portions coming in contact with the electrodes, the electrode signal traces transmit bioimpedance and ECG/EKG (and/or other physiological data) from the electrodes to the main PCB in the electronic housing.

Figure 3E:
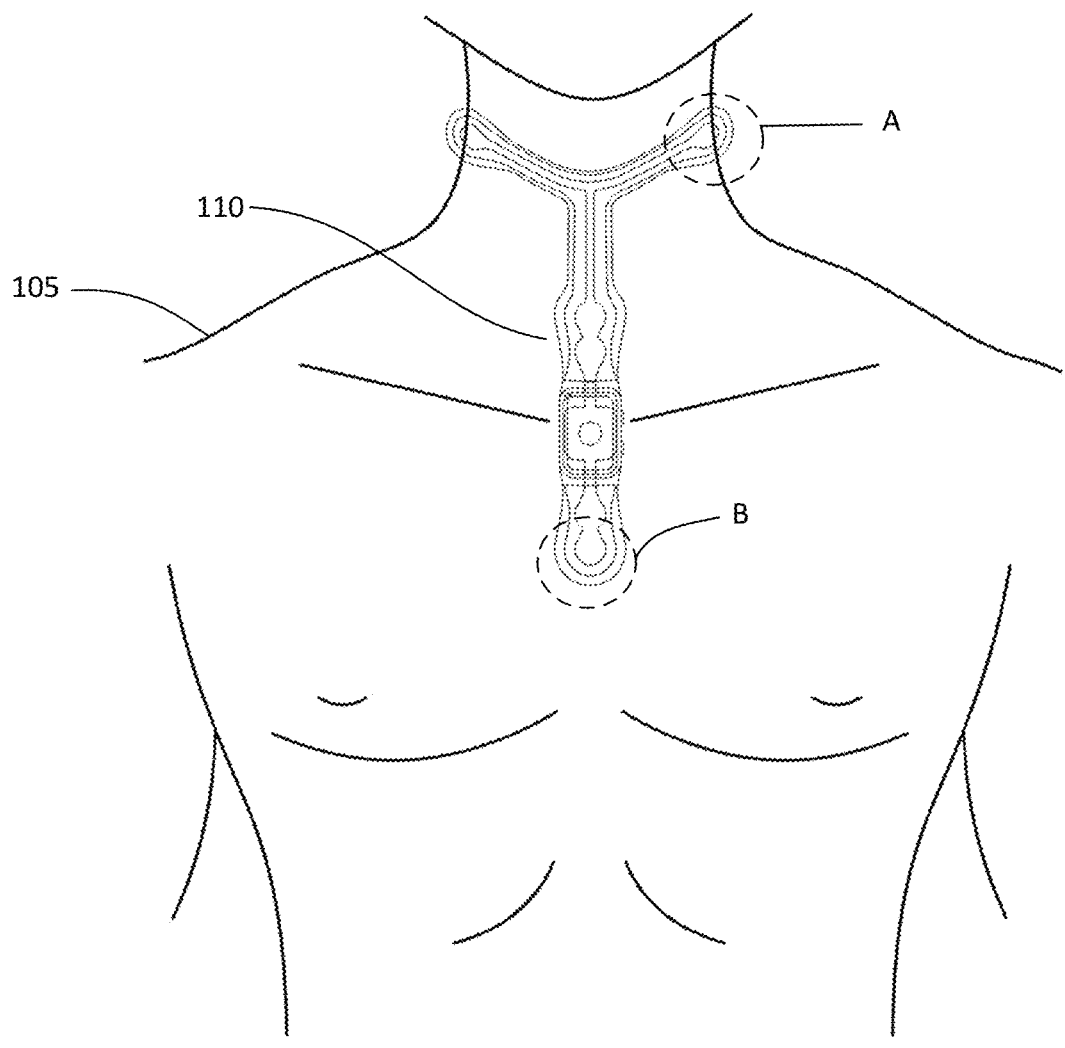
FIG. 3e shows a user wearing an embodiment of a patch for monitoring HF.

FIG. 3*e* shows a user 105 wearing an embodiment of a wearable monitoring device 110 for monitoring HF, such as the one described in FIGS. 3*a*-3*c*. The monitoring device includes pressure sensor arrays for measuring the arterial pressure waveform of the user from the common carotid arteries (indicated by region A) and conductive bioimpedance electrodes for current injection and voltage detection (indicated by region B). The monitoring device may also include an optical sensor system along with a plurality of photodiodes and LED(s) for measuring photoplethysmography waveform from the midsternal region of the user's chest. Details of region A and region B may be similar to those already described in FIGS. $2i_{1-2}$ to 2*k*.

Although the above describes the wearable device having a single patch body, it is understood that the wearable device may include a multi-portion patch body. For example, the wearable device may include a patch body having multiple distinct body portions. Different portions may include their respective power source and communicate wirelessly. In some embodiments, the multi-portion patch body of the wearable device may include two patch body portions. For example, the central body member with extensions is arranged to form two patch body portions. In one embodiment, a first end portion of the central body member with the extensions forms a single neck patch body portion. The elongated portion of the central body member forms a distinct chest patch body portion. In one embodiment, the main PCB is part of the chest patch body portion and a separate battery module is provided in the neck patch body portion for powering the sensors of the neck patch body portion. Data from the sensors of the neck patch body portion are communicated to the main PCB wirelessly. Providing distinct patch body portions advantageously enables the patch body portions to be worn separately by a patient. For example, the neck patch body portion which accommodates the pressure sensor arrays may be worn by the patient a few times a day to measure pressure pulse waveforms. As for the chest patch body portion with the electrodes, it may be worn continuously by the patient on the midsternal line to measure ECG and thoracic bioimpedance waveforms. Having other numbers of the patch body or configurations of the wearable device may also be useful.

In yet another embodiment, the central body member with extensions is arranged to form three patch body portions. For example, a first end portion of the central body member with the extensions forms distinct left and right neck patch body portions. The left neck patch body portion includes the left pressure sensor array configured to be disposed on the left common carotid artery while the right neck patch body portion includes the right pressure sensor array configured to be disposed on the right common carotid artery. An elongated portion of the central body member forms a distinct chest patch body portion. The main PCB is included on the chest patch body portion. Separate battery modules are included in the left and right neck patch body portions for operating the sensors. The left and right neck patch body portions, in one embodiment, are configured to transmit the pressure sensor data to the main PCB via wireless communication (e.g, BLE or EQS-HBC) modules. The neck and chest patch body portions can be worn separately by a patient. For example, the neck patch body portions which accommodate the pressure sensor arrays may be worn by the patient a few times a day to measure pressure pulse waveforms. As for the chest patch body portion with the electrodes, it may be worn continuously by the patient on the midsternal line for continuous measurement of ECG and thoracic bioimpedance waveforms. Other configurations of wearing the patch body portions may also be useful.

Figure 4A:
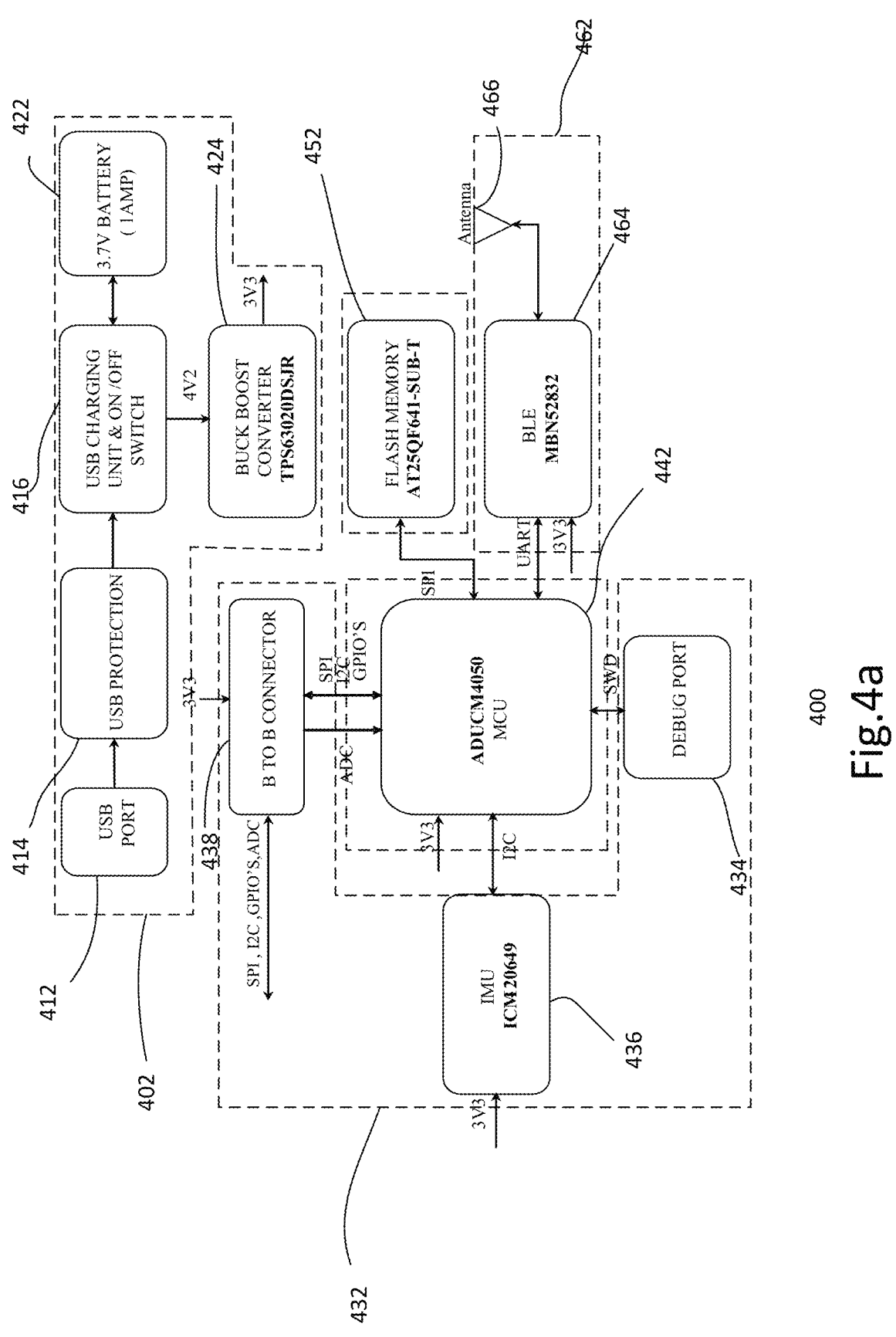
FIGS. 4a-4b show embodiments of a main PCB and a bottom PCB.
Figure 4B:
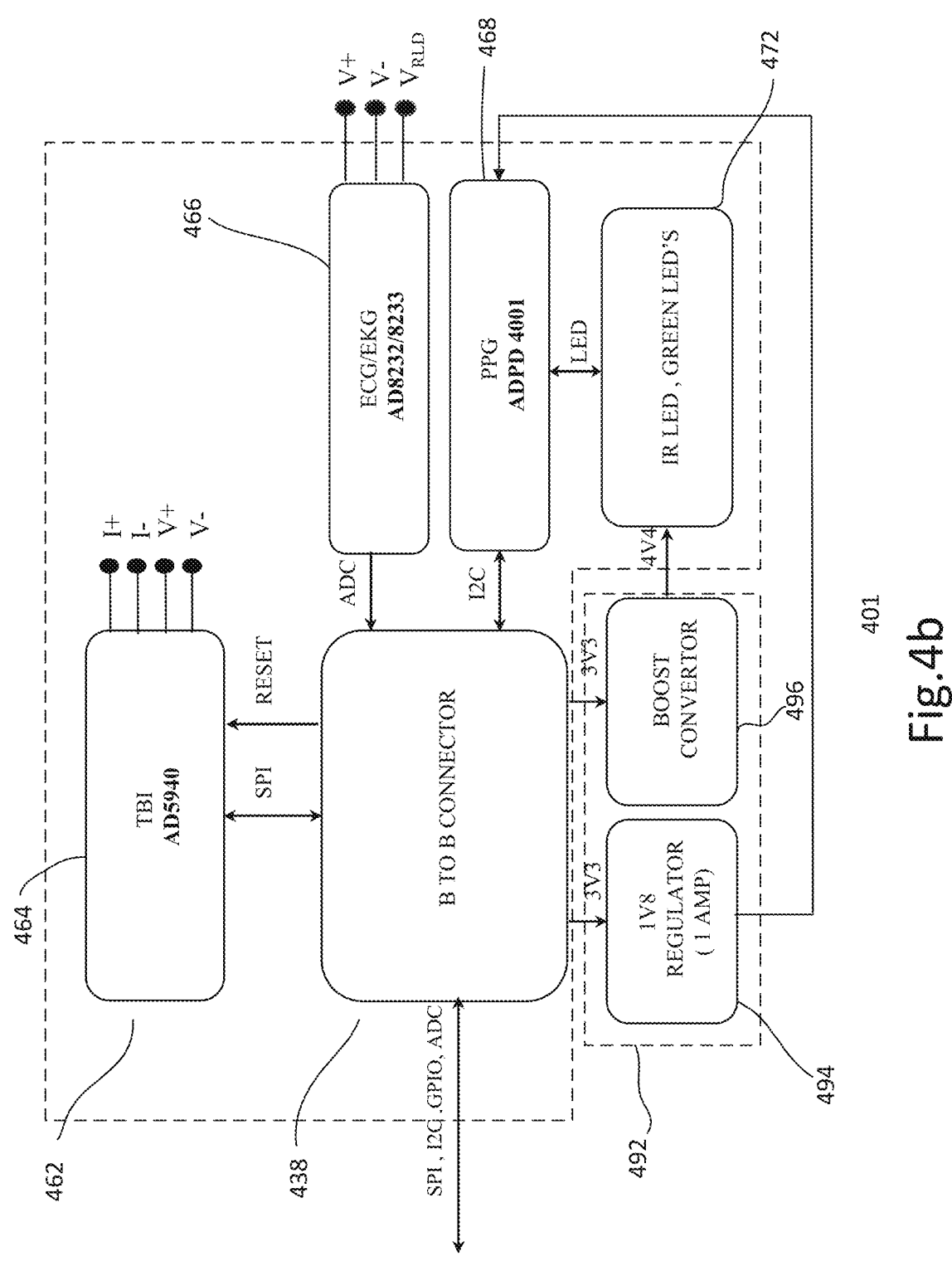

FIGS. 4a-4b show embodiments of a main PCB 400 and a bottom PCB 401. The PCBs include various digital circuits or sub-systems for performing various functions of the wearable device.

Referring to FIG. 4a, one embodiment of the main PCB includes a main power management subsystem 402, a main input subsystem 432, a processing subsystem 442, a storage subsystem 452 and a wireless transmission subsystem 462.

In one embodiment, the power management subsystem manages the power, including serving as a power supply or actuating the functioning of the entire circuit system of the device while protecting it from a surge. The power management subsystem, in one embodiment, includes a USB port 412, a USB protection module 414, a USB power module 416, a battery module 422 and a power converter module 424. The USB port provides a USB connection to the main PCB.

As for the USB protection module, it protects the main PCB from power surges from connections to the USB port. The USB power module enables charging of the battery in the battery module through the USB port. The battery, for example, may be a 3.7V battery (1 amp). Other types of batteries may also be useful. In addition, the USB power module includes a power switch for switching the system on and off. In one embodiment, the power converter module converts input voltage, from either the USB port or directly from the rechargeable battery, to voltages required to power the different subsystems of the entire circuit system. For example, the power converter regulates the power to the different components of the PCBs. The power converter module, for example, may include a buck boost converter, such as a TSP63020DSJR. Other types of power converters may also be useful.

As for the main input subsystem, it includes a board-to-board (B-to-B) connector module 438, an inertial motion unit (IMU) 436 and a debug port 434. The B-to-B connector module is configured to connect the main PCB to the bottom PCB. The B-to-B connector module connecting the PCBs enables signals, including data, command, and power, to be exchanged between the bottom PCB and the main PCB. For example, data from the electrodes is provided from the bottom PCB to the main PCB. As for data from the pressure sensors, it can be transferred directly to the main PCB through the wireless communication module. In the case that wireless communication is not available, the pressure sensor data may be transferred via SPI/I2C protocol from the neck PCB to the bottom PCB and then via the B-to-B connector to the microcontroller in the main PCB board.

Data from the bottom PCB may include the bioimpedance and the ECG/EKG waveforms measured by the voltage electrodes (V+, V−) and the PPG waveform from the PPG sensor. The various data from the bottom PCB may be provided by various types of interfaces in respective formats, such as I2C, SPI, GPIO and ADC. The type of interface may depend on, for example, from where the data is received including the choice of analog front end (AFE) chipsets.

The IMU includes, for example, a 3-axis gyroscope and a 3-axis accelerometer to enable the detection of movement of the user wearing the monitoring device. The IMU provides movement data of the user in, for example, the I2C format. As for the debug port, it provides access for debugging the system. Data to and from the debug port may be in the SWD (Sample with data) format.

In one embodiment, the ECG/EKG and bioimpedance waveforms are simultaneously obtained from V+ and V− electrodes. For example, the voltage signals used to generate the ECG and bioimpedance waveforms are from the V+ and V− electrodes. The voltage signals from the V+ and V− electrodes may be input to different analog-front-ends (AFEs) on the bottom PCB to generate the ECG/EKG and bioimpedance waveforms. For example, the V+ and V− signals serve as input signals to an AD5940 for generating the bioimpedance waveform and to an AD8233 or an AD8232 for generating the ECG/EKG waveform. Alternatively, bioimpedance, ECG/EKG and PPG waveforms can also be simultaneously obtained using a single integrated AFE such as AFE4500.

In one embodiment, output from the pressure sensor arrays may be provided wirelessly to the main PCB by the wireless transmission subsystem 462. The wireless transmission subsystem may include a low energy Bluetooth (BLE) unit 464 and an antenna unit 466. In another embodiment, the wireless transmission subsystems may include an Electro-Quasistatic human body communication (EQS-HBC) module. The BLE unit, for example, may be an MBN52832 BLE unit from Murata whereas the EQS-HBC module may be a body area network (BAN) integrated circuit (IC) from Quasistatics Inc. In one of the embodiments, the antenna unit may be an integral part of the BLE unit. Data to and from the wireless transmission subsystem may be in the UART.

The processing subsystem 442 is configured to preprocess the input data from the bottom PCB, the wireless transmission subsystem and the IMU. The processing subsystem, for example, may be a microcontroller unit (MCU), such as an ADUCM4050 from Analog Devices, USA. Other types of processing subsystems may also be useful. The preprocessed data may be forwarded to the user's mobile device for further interpretation, such as by a server by the wireless transmission subsystem. The wireless transmission subsystem enables data representation to occur on the mobile device in both graphical and dashboard forms. The user's mobile device, for example, may be an Android or IOS device. Other types of platforms for mobile devices may also be useful. The preprocessed data may also be stored on the storage subsystem, as required. The storage subsystem, for example, may be a NOR flash memory, such as an AT25QF641-SUB-T from Adesto Technologies, or a spin torque based magnetic memory device, such as an EMD3D256M from Everspin Technologies, USA. Other types of storage subsystems may also be useful.

As described, the B-to-B connector module interconnects the main PCB to the bottom PCB. This enables seamless data signal connections between both PCBs as well as the processing subsystem on the main PCB to process the data from the bottom PCB along with the data signals from the main PCB.

FIG. 4b shows an embodiment of the bottom PCB. The bottom PCB includes a bottom input subsystem 462 and a bottom power management subsystem 492. Providing the bottom PCB with other subsystems may also be useful.

The bottom input subsystem includes various analog front-end modules for receiving data from the sensors and electrodes of the wearable device. In one embodiment, the input subsystem includes a TBI analog front-end module 464, an ECG analog front-end module 466, a PPG analog front-end module 468 and an LED & Photodiode module 472. In yet another embodiment, the bottom input subsystem may include a single integrated analog front-end module for TBI, ECG, PPG, LED and PD, enabling signals to be seamlessly communicated from one PCB to the other PCB.

The bottom input subsystem is connected to the main PCB by the B-to-B connector module 438. For example, the B-to-B connector module shown in FIG. 4b is common for both the bottom and main PCBs. Other configurations for connecting the bottom and main PCBs may also be possible. For example, each PCB may include a B-to-B connector module connected to each other.

In one embodiment, the ECG analog front-end module 466 detects ECG signals of the user wearing the device and converts the analog signals into digital signals. The ECG analog front-end module with the Right-leg drive (RLD) electrode enables data acquisitions from a single lead ECG device. For example, signals from the pair of voltage electrodes (V+ and V− electrodes) of the bioimpedance electrodes and the $V_{RLD}$ from the RLD electrode are input to the ECG analog front-end module. In the case that the wearable patch does not include a separate RLD electrode, the RLD input of the ECG front end is connected to the ground. The digital signals of the ECG analog front-end module, for example, are in the ADC format. In one embodiment, the ECG analog front-end module is an AD8232/8233 IC. Other types of ECG analog frontend modules may also be useful.

As for the TBI analog front-end module 464, it detects thoracic bioimpedance Z and impedance cardiography dZ/dt of the user from the bioimpedance electrodes. For example, it reads a differential of the measured voltage between the voltage electrodes V+ and V− with respect to the magnitude of the injected current through the current electrodes I+ and I−. The readings in analog signals are converted into digital signals, using the analog-to-digital converter inbuilt in the bioimpedance analog front end. In one embodiment, the TBI module is an AD5940 IC from Analog Devices, USA. Other types of TBI modules such as AD5933 from Analog devices, USA or AFE4500 ultra-small integrated AFE from Texas Instruments, USA may also be useful.

As described, an ECG receiver with a right-leg drive (RLD) can enable the acquisition of a single-lead ECG from the V+ and V− readings shared with the bioimpedance measurement. While V+ and V− readings are outputs of the bioimpedance measurement, V+, V− and $V_{RLD}$ readings are input to the ECG/EKG analog front-end module.

The PPG sensor front-end module 468 is connected to the LED & Photodiode module 472 to control the LEDs and photodiodes. The PPG module enables the detection of saturated oxygen levels of the user. For example, the PPG sensor module utilizes an infrared light (via IR LED) to measure the volumetric variations of blood circulation. A typical PPG sensor emits light at the tissue site with one or more LEDs. The photodiode measures the intensity of the non-absorbed light reflected from the tissue. Light with longer wavelengths penetrates more deeply into the tissue. For instance, infrared light has a more effective penetration depth in the skin compared to green light, however, it is susceptible to motion artifacts. To reduce movement artifacts, an IMU sensor is employed in the main PCB to capture the direction of the motion. The PPG signal comprises AC and DC components. The AC component depicts changes in blood volume, which are caused by cardiac activity and depend on the systolic and diastolic phases. The DC component is shaped by respiration, sympathetic nervous system activity, and thermoregulation. The output signal of the PPG module may be transmitted to the microcontroller in the main PCB via SPI or I2C protocol.

In one embodiment, the PPG sensor front-end module is an ADPD 4001 IC from Analog Devices, USA with an I2C peripheral to transmit the PPG waveform to the microcontroller. The ADPD 4001 IC includes, for example, three green light-emitting diodes (LEDs), one infrared (IR), and one red LED along with a single photodiode. In another embodiment, the PPG sensor front-end module is an integrated AFE module such as AFE4500 which includes a PPG signal chain provided with both SPI and I2C peripherals for transmitting PPG waveform. The AFE4500 may also include 8 LEDs and 4 photodiodes in each phase and supports acquisition of up to 24 PPG signals. Other types of PPG modules may also be useful.

In one embodiment, the bottom power management subsystem 492 manages the power to the various modules of the bottom PCB. The power management subsystem includes a regulator unit 494 and a boost converter unit 496. The regulator and boost converter units receive power from the power supply in the main PCB through the B-to-B connector module.

As described, SPI/I2C/GPIO are the digital peripherals or communication interfaces that transmit data from the AFEs in the bottom PCB to the microcontroller in the main PCB. Any AFE which supports SPI or I2C or GPIO interfaces (i.e. digital pins in the IC for communication purposes) can transmit data through those interfaces via the B-to-B connector. For example, an AFE which supports the GPIO interface can transmit data via a B-to-B connector to the microcontroller.

Figure 4C:
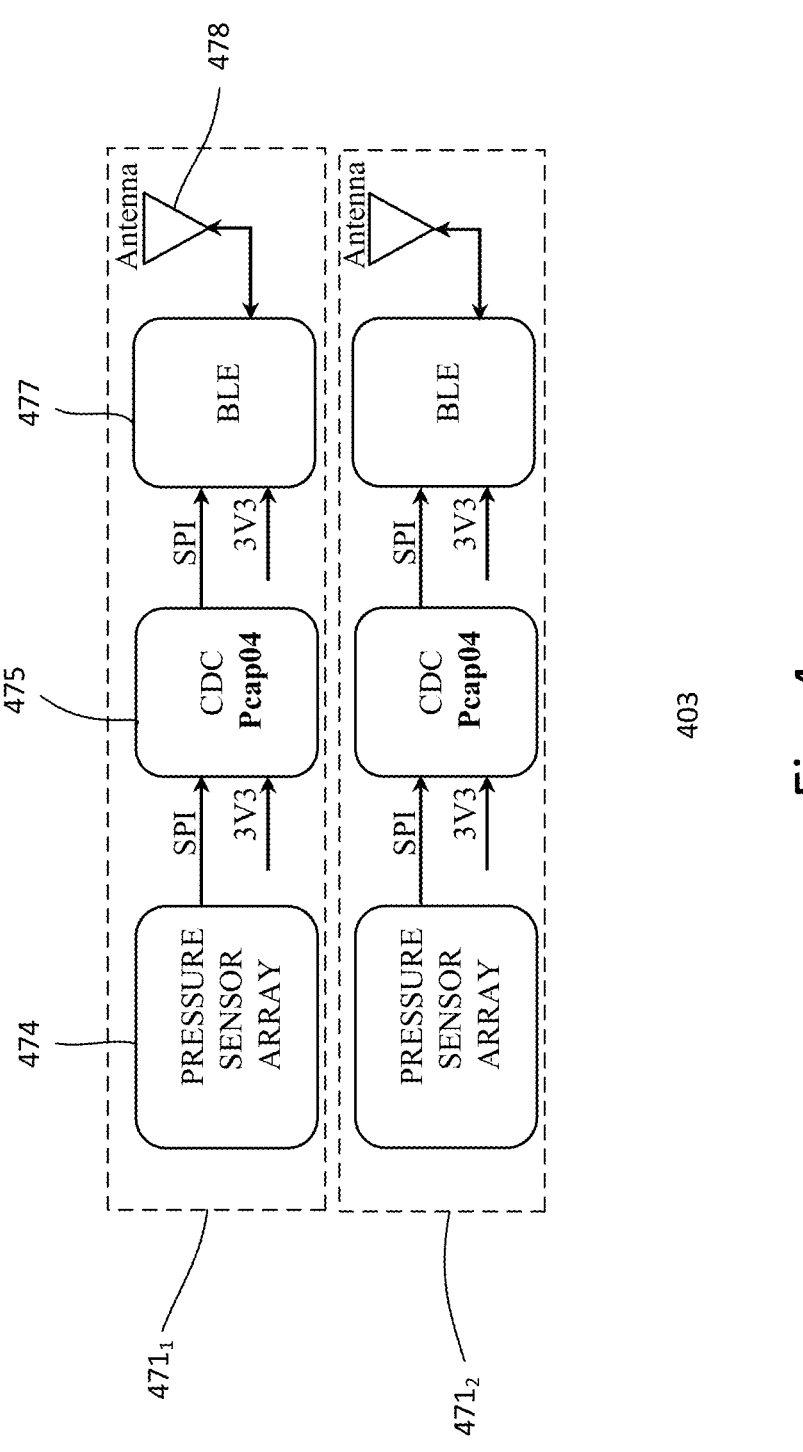
FIG. 4c shows an embodiment of sensor array electronics.

FIG. 4c shows a simplified block diagram 403 of the pressure sensor array modules 471 of the wearable device. As shown, the block diagram includes first and second sensor modules $471_{1-2}$. The block diagrams for the pressure sensor modules are preferably the same. A pressure sensor module includes a pressure sensor array 474. The pressure sensor array, for example, includes three pressure sensors, such as MEMS sensors as described in FIG. 2f Other types of pressure sensors may also be useful.

The pressure sensor array may be soldered onto a flexible PCB. The flexible PCB includes a capacitance-to-digital converter (CDC) 475. The CDC is connected to the pressure sensor array. The CDC receives the capacitive signal produced by the sensor array and converts it to a digital signal. The measurement is based on measuring the discharge time on RC-networks. Each pressure sensor capacitance is measured within its dedicated cycle. For example, the capacitor is first loaded with a full charge. The CDC then uses configurable discharge resistors to discharge the capacitor. The actual measurement occurs from the start of the discharge cycle until a threshold voltage is reached. The CDC, for example, may be a capacitive sensing front end PCap04 from ams OSRAM AG, Austria, which is controlled via an in-built ultra-low-power Cortex-M4F with FPU-Based Microcontroller with 2 MB Flash and 256 KB SRAM. Other types of CDCs may also be useful.

A simple capacitive loss model reveals that the power consumption is approximately 5 micro-watt when using a ~3.3 V power supply and a 100 kHz readout frequency. This evidences that monitoring for long periods with minimal battery size is feasible.

In one embodiment the flexible PCB also includes a wireless transmission module or unit 477. The wireless transmission unit, for example, is a Bluetooth (BLE) unit with an antenna 478. In another embodiment, the wireless transmission subsystems may include an Electro-Quasistatic human body communication (EQS-HBC) module. The wireless transmission unit receives the digital signal from the CDC and transmits it wirelessly to the main PCB. In other embodiments, the digital signal from the CDC may be connected to the trace unit for wired transmission to the main PCB. Other configurations of the pressure sensor array modules may also be useful.

In one embodiment, the pressure sensor array modules are integrated into a wearable monitoring device. When the wearable monitoring device is worn by the user, one of the pressure sensor array modules is placed on the left carotid artery while the other pressure sensor array module is placed on the right carotid artery for measuring left and right carotid artery pressure pulse waveforms respectively.

Figure 5A:
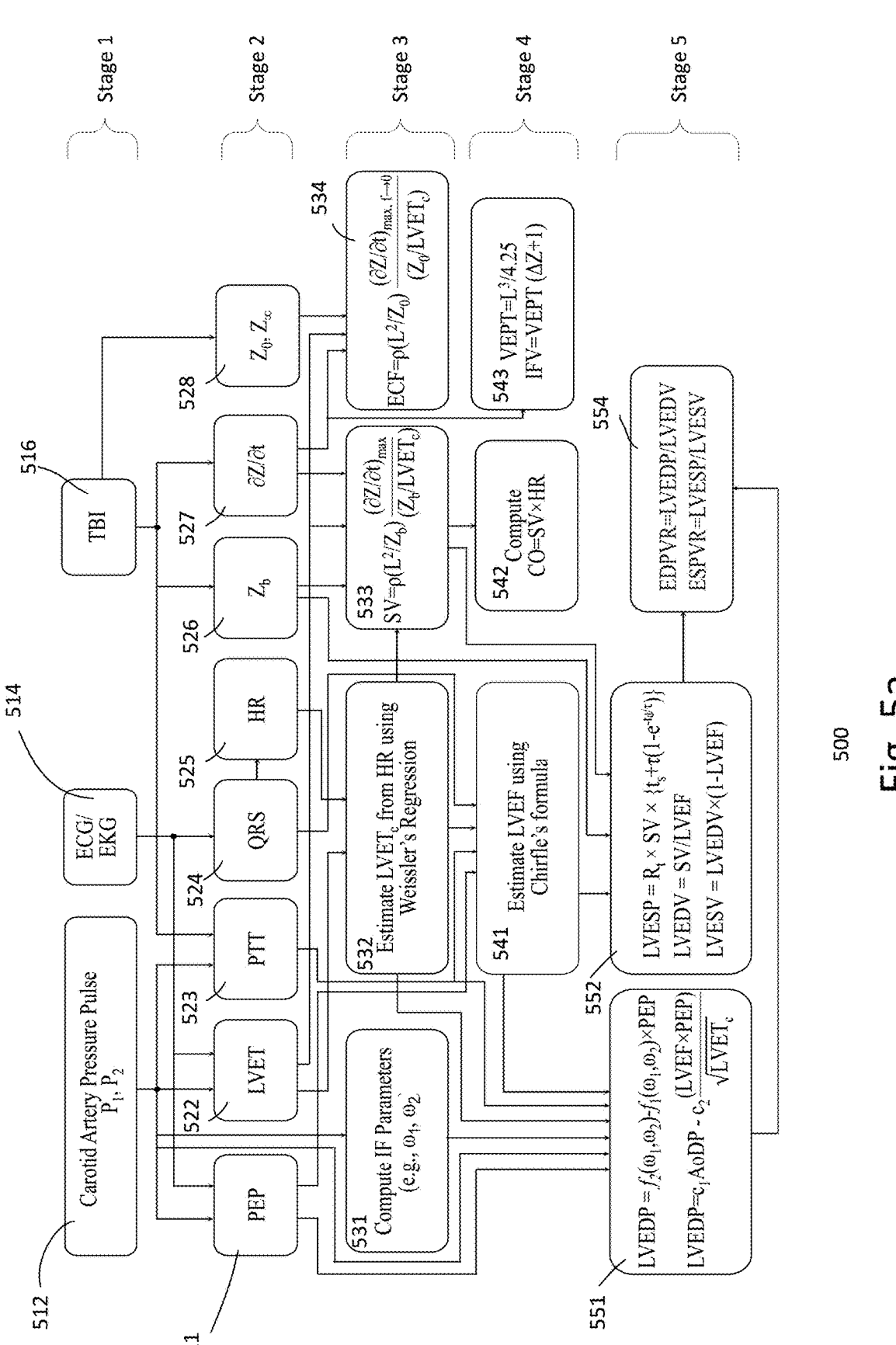
FIG. 5a shows a flow for calculating LV hemodynamic and vital parameters.

FIG. 5*a* shows a software flow 500 for extracting clinical parameters from data measured from the sensors and electrodes of the wearable device. The wearable device is similar to that described in FIGS. 2*a*-2*c* and FIGS. 3*a*-3*c*. Clinical parameter extraction, in one embodiment, is performed by a server, such as a cloud server. For example, preprocessed data from the wearable device is transmitted to the user's mobile device and then transmitted to the server. Alternatively, the preprocessed data from the wearable device may be directly transmitted to the server. For example, the main PCB may include a mobile communication module, such as a GSM module, enabling the preprocessed data to be transmitted to the cloud server via a cellular network. The flow, for example, may be performed by a software application running on the server.

The flow, for example, may include multiple stages for processing the data collected from the wearable device. As shown, the flow includes 5 stages (stage 1 to stage 5). Providing a flow with other numbers of stages may also be useful.

At stage 1, physiological data collected from the wearable device is received. For example, stage 1 may be referred to as an input stage. In one embodiment, carotid artery pressure pulse data (wave or waveform) $P_1$ and $P_2$ from the sensor arrays is received at 512, ECG/EKG data from the V+, V– and RLD electrodes is received at 514 and TBI data from the (I+, V+), and (I–, V–) electrodes is received at 516.

The flow employs the input data to automatically measure systolic time intervals (STI) using ECG/EKG, carotid artery pressure pulse and TBI waveforms and determines heart rate (HR), QRS duration, left ventricular pre-ejection period (PEP), left ventricular ejection time (LVET), and pulse transit time (PTT) and displaying the corrected systolic time intervals, and estimation of LVEF in HF patients.

At stage 2, the input data is employed to calculate left ventricular pre-ejection period (PEP) at 521, left ventricular ejection time (LVET) at 522, pulse transit time (PTT) at 523, QRS duration ($QRS_d$) at 524, heart rate (HR) at 525, thoracic base impedance ($Z_b$) at 526, impedance cardiography $\Delta Z/\Delta t$ at 527, ECF and TBW impedances $Z_0$ and $Z_\infty$ at 528. Other parameters may also be determined at stage 2. For example, even though it is not shown, input data may be employed to determine other parameters, such as respiratory rate (RR), and thoracic lung capacity (TLC).

As shown, ECG waveform is used to determine $QRS_d$, HR, HRV as well as different time intervals such as $QT_c$ (referred to as time interval between Q-peak to T-peak), ST (referred to as time interval between S-peak to T-peak) and other types of time intervals. As for the TBI or bioimpedance waveform, it is used to determine $Z_b$, $\partial Z/\partial t$, $Z_0$ and $Z_\infty$. For example, $Z_b$ can be measured around a frequency of f=100 kHz, while $Z_0$ and $Z_\infty$ are calculated using bioimpedance spectroscopy measurement by sweeping the frequency from a very low frequency f→0 to a very high frequency f→∞ and employing Cole-Cole model to estimate the bioimpedance values at f→0 and f→∞ respectively. The carotid artery pressure waveform along with ECG waveform are used to determine systolic time intervals such as PEP and LVET while the carotid artery pressure waveform along with the TBI are used to determine PTT.

Regarding PEP, it is determined from the carotid artery pressure and the ECG/EKG waveforms. The PEP indicates the time from the onset of QRS or ventricular pacing pulse to the onset of central aortic flow. In one embodiment, the PEP at 521 represents extended or delayed PEP when using the signal trace of the carotid artery pulse as compared to a signal trace obtained in the central aorta.

The extended PEP may be adjusted to corrected PEP ($PEP_c$) by subtracting the pulse transit time (PTT). PTT reflects the duration of ventricular isometric contraction and $PEP_c$ represents a true PEP without the time delay. The $PEP_c$, in one embodiment, represents extended PEP which has been fully corrected for the selected QRS type or LV pacing mode, with no intra-vascular delay (IVD). In one embodiment, $PEP_c$ is defined as:

$$PEP_c = PEP - PTT \tag{Equation 1}$$

In the case that there is a finite IVD, IVD may be equal to $0.38 \times QRS_d - 8$. As such, $PEP_c$ with a finite IVD is defined as:

$$PEP_c = PEP - PTT - IVD \tag{Equation 2}$$

At stage 3, the flow computes intrinsic frequency (IF) parameters at 531, estimates the LVET at 532, calculates the stroke volume (SV) at 533 and also calculates the thoracic fluid content (TFC) and extracellular fluid (ECF) at 534.

In one embodiment, the IF parameters at 531 include $\omega_1$, $\omega_2$, and $\Delta\omega_L$, where $\omega_1$ describes the dynamics of the systolic phase of the cardiac cycle when the left ventricle (LV) and aorta are coupled and $\omega_2$ belongs to the diastolic phase when the aorta and vascular branches are decoupled from the LV. $\Delta\omega_L$ represents the difference ($\omega_1 - \omega_2$) between $\omega_1$ and $\omega_2$. The IF parameters are, for example, calculated from either $P_1$ or $P_2$ or both. For example, $\omega_1$ & $\omega_2$ may be obtained using an IF algorithm that uses the information stored in the carotid artery pressure waveforms to create a multidimensional function. The IF algorithm, in one embodiment, models a coupled LV-aorta system. The IF algorithm is based on, for example, an L2-minimization that uses the carotid artery pressure waveforms to compute the IF parameters such as $\omega_1$ and $\omega_2$.

The LVET is estimated at 532. LVET represents the time from the onset to the end of aortic pressure. In one embodiment, a HR-corrected LVET ($LVET_c$) is estimated based on HR and LVET from stage 2. The HR-corrected LVET is defined as:

$$LVET_c = LVET + k(HR - HR_b) \qquad \text{(Equation 3a)},$$

where k is the slope of LVET/HR.

An actual value of k can be calculated as the ratio between a change in LVET resulting from a change in HR, where a base HR is calculated as $HR_b = 60{,}000\text{-}72{,}000/\text{cycle}$ length (ms). By correcting LVET for HR, comparisons are more accurate within the same user at different heart rates or when compared to other users.

Alternatively, other techniques for determining $LVET_c$ are also possible. For example, Weissler's Regression can be employed. In such cases, $LVET_c$ can be computed separately for males and females as shown:

$$LVET = -0.0017HR + 0.413(\text{males}) \qquad \text{(Equation 3b)},$$

$$LVET = -0.0016HR + 0.418(\text{females}) \qquad \text{(Equation 3c), and}$$

with standard deviation=0.010 sec.

The LVET and estimated $LVET_c$ from stages 2 and 3 may be used to calculate stroke volume (SV).

Regarding SV, it is defined as the amount of blood ejected from the left ventricle in one cardiac cycle and expressed as the difference between the end-diastolic volume (EDV) and end-systolic volume (ESV). In one embodiment, SV at 533 can be obtained by sensing the bioimpedance waveform and its derivative to calculate base impedance $Z_b$ and $(\partial Z/\partial t)_{max}$. For example, SV can be defined as:

$$SV = \rho (L^2/Z_b)(\partial Z/\partial t)_{max}/(Z_b/LVET) \qquad \text{(Equation 4a), or}$$

$$SV = \rho (L^2/Z_b)(\partial Z/\partial t)_{max}/(Z_b/LVET_c) \qquad \text{(Equation 4b)},$$

where $\rho$ is the resistivity of blood,

L is the distance between the voltage electrodes (V+ and V− electrodes).

$Z_b$ is the base impedance, $(\partial Z/\partial t)_{max}$ is the absolute value of the cyclic peak of the derivative of $Z_b$, and LVET is extended left ventricular ejection time, or $LVET_c$ is corrected left ventricular ejection time.

In another embodiment, SV can be obtained from the carotid artery pressure waveforms and their derivatives such as the IF parameters. For example, SV can be expressed as:

$$SV = \omega_2(\alpha_1 - \alpha_2(PEP_c/LVET_c)) \qquad \text{(Equation 4c)},$$

where $\omega_2$ is the intrinsic frequency of the diastolic phase when the aorta and vascular branches are decoupled from the LV, $\alpha_1$ and $\alpha_2$ are universal constants, $PEP_c$ is corrected left ventricular pre-ejection period, and $LVET_c$ is corrected left ventricular ejection time.

In one embodiment, the extracellular fluid (ECF) determined at 534 can be defined as $$ECF = \rho(L^2/Z_0)(\partial Z/\partial t)_{max,f \to 0}/(Z_0/LVET_c) \qquad \text{(Equation 5)},$$

where $\rho$ is the resistivity of blood,

L is the distance between the voltage electrodes (V+ and V− electrodes), $Z_0$ is the impedance at a very low frequency of, for example, when $f \to 0$, $(\partial Z/\partial t)_{max,f \to 0}$ is the absolute value of the cyclic peak of the derivative of $Z_0$, and $LVET_c$ is corrected left ventricular ejection time.

In one embodiment, thoracic fluid content (TFC) is also determined at 534. For example, the TFC can be defined as:

$$TFC = 1000/Z_b \qquad \text{(Equation 6)}.$$

In some embodiments, minute ventilation (MV) may also be determined at stage 3. For example, MV can be determined from respiratory rate (RR) and thoracic lung capacity (TLC) calculated at stage 2.

At stage 4, left ventricular ejection fraction (LVEF) is estimated at 541. The LVEF is estimated using, in one embodiment, Chirfle's formula. For example, LVEF can be estimated as follows:

$$LVEF = (k_1 \, \text{Log}_e(LVET_c/PEP_c) + k_2) \times 100 \qquad \text{(Equation 7)},$$

where $k_1$ and $k_2$ are constants, $LVET_c$ is corrected left ventricular ejection time, and $PEP_c$ is corrected left ventricular pre-ejection period.

Alternatively, LVEF is estimated using Weissler's Regression. For example, LVEF can be estimated as follows:

$$LVEF = k_3 - k_4 \, PEP_c/LVET_c \qquad \text{(Equation 8)},$$

where $k_3$ and $k_4$ are constants, $LVET_c$ is corrected left ventricular ejection time, and $PEP_c$ is corrected left ventricular pre-ejection period.

The constants $k_1$, $k_2$, $k_3$ and $k_4$ used in Equations 6 and 7 can be obtained by comparing $PEP_c/LVET_c$ (Weissler's ratio) with LVEF measured by echocardiography (ECG) or, MRI or any other Gold-Standard devices.

As shown, stage 4 also includes computing cardiac output (CO) at 542. In one embodiment, CO is defined as:

$$CO = SV \times HR \qquad \text{(Equation 9)}.$$

At 543, the volume of electrically participating tissues for thoracic bioimpedance measurement (VEPT) and interstitial fluid volume (IFV) or extravascular fluid volume are also computed. For example, VEPT and IFV can be defined as:

$$VEPT = L^3/4.25 \qquad \text{(Equation 10), and}$$

$$IFV = VEPT(\Delta Z + 1) \qquad \text{(Equation 11)},$$

where

L is the distance between the voltage electrodes (V+ and V−), and $\Delta Z$ is the change in thoracic bioimpedance.

At stage 5, left ventricular end-diastolic pressure (LVEDP) is calculated at 551 and left ventricular end-systolic pressure (LVESP) is calculated at 552.

In one embodiment, LVEDP is calculated using a "cardiac triangle" technique. For example, a triangular relationship of the relevant parameters can be formed using arterial diastolic pressure (AoDP), pre-ejection period (PEP) and contractility (Ctr), and left ventricular end-diastolic pressure (LVEDP). This is represented in the form of the slope of a contractility function which can be defined as:

$$LVEDP = AoDP - Ctr \times PEP \qquad \text{(Equation 12a)}.$$

Equation 12a can be generalized as:

$$LVEDP = \beta_1 + \beta_2 AoDP + \beta_3 (Ctr \times PEP) \qquad \text{(Equation 12b)},$$

where $\beta_1$, $\beta_2$, and $\beta_3$ can be a universal physiological constant or a user specific constant.

To determine Ctr and the two intrinsic frequencies (IFs) $\omega_1$ and $\omega_2$, information is extracted from the common carotid artery pressure pulse waveform. As discussed, the IF parameters are obtained from an IF algorithm which assumes there are two dominant dynamical frequencies $\omega_1$ and $\omega_2$ before and after the closure of the aortic valve. The IF algorithm uses the hemodynamic information stored in the carotid artery waveform to create a 5-dimensional IF space, with $\omega_1$, $\omega_2$, $T_0$ (=LVET), T (=length of a Cardiac cycle) and the relative height of decoupling at the dicrotic notch. For example, based on a Sparse Time-Frequency Representation (STFR) technique, a non-linear and non-stationary signal s(t) of the waveform is decomposed into a finite sum of Intrinsic Mode Functions (IMF). The IMF can be defined as: R(t) cos θ (t)):s(t)=$\Sigma R_i$(t) cos $\theta_i$ (t), i=1(1)M, where $R_i$(t) is the envelope, $\theta_i$(t) is the phase, and $\theta_i$ is the time derivative of an instantaneous frequency (d$\theta_i$/dt).

Each IMF models the dynamical system as an object rotating around an origin with a time-dependent radius (envelope) and a time-dependent angular velocity (instantaneous frequency). The intrinsic frequency (IF) algorithm assumes that the envelope and the instantaneous frequency are piecewise constants in time with the step at the decoupling time (or the time of the dicrotic notch i.e. t=$T_0$=LVET). In this case, the IF algorithm for the LV-arterial system only considers the first IMF, which carries the maximum signal energy.

As an example, the IF representation of a single arterial pressure waveform for the firstIMF is defined as:

$$P(a_i, b_i, \omega_i, c; t) = \chi_{(0,LVET)}[(a_1 \cos(\omega_1 t) + b_1 \sin(\omega_1 t)] +$$

$$\chi_{(LVET,T)}[(a_2 \cos(\omega_2 t) + b_2 \sin(\omega_2 t)] + c,$$

where $$\chi_{(\alpha,\beta)}(t) = \begin{pmatrix} 1, \alpha \leq t < \beta \\ 0, \text{ otherwise} \end{pmatrix}.$$

The parameters $a_1$, $a_2$, $b_1$, $b_2$ are the envelopes of the IF model fit; $\omega_1$ and $\omega_2$ are the first and second intrinsic frequencies, and c is a translation constant for the whole period [0,T]. In order to find the IF parameters, an $L^2$ minimization problem is solved ensuring continuity at dicrotic notch time t=LVET and periodicity at t=T. However, $L^2$ optimization formulation is computationally expensive. Therefore, a sequentially reduced fast-forward neural network (FNN) is employed to extract the dicrotic notch time along with the waveforms to IF parameters (i.e., $\omega_1$ and $\omega_2$).

In one embodiment, an FNN structure comprises one input layer, L hidden layers, and one output layer. The target FNN should map the high-dimensional input vector x into an output vector y of a significantly lower dimension (size). This results in a network of a sequentially-reduced structure, with uniformly decaying numbers of neurons where the number of neurons is reduced by half in each hidden layer. The inputs of the FNN are the normalized carotid artery waveform as well as the normalized dicrotic notch time. The outputs of the model are the scaled IF parameters $\hat{\omega}_1$, $\hat{\omega}_2$, $\hat{R}_S$, $\hat{\varphi}_1$ and $\hat{c}$, where $R_S$ and $\varphi_1$ are the envelope of the IF construction and intrinsic phase with $\omega_1$ respectively. Other scaled IF parameters such as $\hat{R}_D$, $\hat{\varphi}_2$ can be analytically computed from these five outputs as:

$$\hat{\varphi}_2 = \tan^{-1}\left( \frac{\text{Sin}(\hat{\varphi}1)\ \text{Sin}(\hat{\omega}_2 \hat{T}_0) - \text{Sin}\ (\hat{\omega}_1 \hat{T}_0 + \hat{\varphi}1)\ \text{Sin}(\hat{\omega}_2)}{\text{Sin}\ (\hat{\omega}_1 \hat{T}_0 + \hat{\varphi}1)\ \text{Cos}(\hat{\omega}_2) - \text{Sin}\ (\hat{\varphi}1)\ \text{Cos}\ (\hat{\omega}_2 \hat{T}_0)} \right)$$

(Equation 13a)

$$\hat{R}_D = \frac{\hat{R}_S\ \text{Sin}\ (\hat{\varphi}1)}{\text{Sin}\ (\hat{\omega}_2 + \hat{\varphi}2)}$$

(Equation 13b)

where $R_D$ and $\varphi_2$ are the envelope of the IF construction and intrinsic phase with $\omega_2$ respectively and $T_0$=LVET.

Since the output variables have different scales (ranges), feature scaling is performed in order to train a network to have uniform accuracy across all output variables. The model is designed (i.e., trained, validated and tested) with a heterogeneous database that includes existing clinical pressure waveforms as well as the carotid pressure waveforms measured using the pressure sensor array embedded in the wearable patch. The existing clinical dataset is generated from the carotid pressure waveforms measured using traditional tonometry devices (e.g., piezoelectric or millimeter-wave, such as radar-based systems).

Once $\omega_1$ and $\omega_2$ are calculated, LVEDP is computed at 551 using:

$$\text{LVEDP}=f_2(\omega_1,\omega_2)-f_1(\omega_1,\omega_2)\times\text{PEP}$$ (Equation 15).

As such, LVEDP can be computed from the intrinsic frequencies $\omega_1$ and $\omega_2$ and the STI parameters, all of which can be measured non-invasively using the wearable patch.

As an alternative, LVEDP can be defined as:

$$\text{LVEDP}=\text{AL}-\text{Ctr}\times\text{PEP}$$ (Equation 16a).

For example, functions of $\omega_1$ and $\omega_2$ can be represented by LV contractility (Ctr) and afterload (AL) instead. For example, contractility is indicated as ctr≈$f_1(\omega_1,\omega_2)$ and afterload is indicated as AL≈$f_2(\omega_1,\omega_2)$. Afterload refers to the amount of pressure that the left ventricle needs to exert to eject the blood during ventricular contraction.

In addition, recent results also showed that $\omega_1$ is highly correlated with various indexes of LV contractility (MM-based Measures of Left Ventricle Contractility and Intrinsic Frequency. In Proceedings of the IEEE-Engineering in Medicine and Biology Society (EMBC), Honolulu, HI, USA, 17-21 Jul. 2018). For example, $\omega_1$ corrected with the LV ejection time ($\omega_1\sqrt{\text{LVET}_c}$) is strongly correlated with LVEF. As a result, $f_1(\omega_1,\omega_2)$ can be replaced with LVEF/$\sqrt{\text{LVET}_c}$. As for afterload (AL), it can be replaced by Aortic diastolic pressure (AoDP) measured using the pressure sensor array at the common carotid artery. Therefore, Equation 14a can be further simplified as:

$$\text{LVEDP}=c_1\text{AoDP}-c_2(\text{LVEF}\times\text{PEP}_c)/\sqrt{\text{LVET}_c}$$ (Equation 16b), where $c_1$ is a unitless constant, $c_2$ is a constant with a unit of mmHg/$\sqrt{}$Second, and $c_1$ and $c_2$ can be obtained, for example, using linear multiple regression.

In yet another embodiment, LVEDP can be calculated using:

$$\text{LVEDP}=[c_3(\text{MAP})\times(1-\text{LVEF})]-c_4$$ (Equation 17), where MAP is the mean arterial pressure measured using the pressure sensor array at the common carotid artery, $c_3$ is a unitless constant, and $c_4$ is a constant with a unit of mmHg.

This appears to be the most accurate, reliable, and easily applied technique for estimating LVEDP noninvasively in patients with preserved ejection fraction and an LVEDP<20 mm Hg.

Stage 5 also includes computing left ventricular end-systolic pressure (LVESP), left ventricular end-diastolic volume (LVEDV), and left ventricular end-systolic volume (LVESV) at 552. As shown, the LVEDP calculated at 551 is used along with the LVESP, LVEDV and LVESV computed at 552. The slopes of the end-systolic pressure-volume relationship (ESPVR), also known as the end-systolic elastance ($E_{es}$) and the end-diastolic pressure-volume relationship (EDPVR), are then determined at 554.

In one embodiment, the framework for deriving ESPVR and EDPVR is based on the time-varying elastance model of the left ventricle. The E(t) defines the heart as a dynamic chamber that varies its stiffness during the cardiac cycle and is represented as:

$$E(t)=P(t)/[V(t)-V_0] \qquad \text{(Equation 18)},$$

where

P(t) is instantaneous ventricular pressure,

V(t) is the instantaneous ventricular volume, $V_0$ is the slack volume that is determined iteratively.

This model describes the ventricle as an elastic chamber that actively increases its stiffness during systole (with a maximum at the end of the systole) and decreases it with the onset of diastole. E(t) is theoretically insensitive to loading conditions but altered by changes in contractility. The elegance of this model lies in the fact that, if the ventricular PV analysis describes most of the features of the mechanical properties of the ventricle, the ESPVR and EDPVR define their boundaries. For example, ESPVR and EDPVR represent the load-independent measures of ventricular contractility and diastolic compliance by measuring the slopes in the left ventricular pressure-volume diagram. In a patient with well-compensated HF with reduced ejection fraction (HFrEF), contractility is depressed. This leads to a shallower ESPVR. However, the LV can still supply a near-normal SV at rest and, in some cases, even maintain acceptable LV end-diastolic pressure (LVEDP) because of an increase in LV volumes. EF is depressed due to LVEDV being increased, not because the SV is decreased.

In one embodiment, LVESP at 552 is determined from effective arterial afterload $E_a$. For example, using the above model, $E_a$ can be expressed as $E_a$=LVESP/(LVEDV−LVESV)=LVESP/SV. Therefore, LVESP=$E_a$×SV. As such, $E_a$ is a lumped parameter of aortic input impedance, which captures relevant information about both pulsatile and resistive components of afterload. $E_a$ can be derived from the known 3-element Windkessel model:

$$E_a=R_t\times\{t_S+\tau(1-\exp(-t_d/\tau))\} \qquad \text{(Equation 19a)},$$

where $t_S$ is the systolic period, $t_d$ is the diastolic period, $R_t$ is the total mean vascular resistance (peripheral resistance plus characteristic impedance), and $\tau$ is the diastolic time constant.

Changing ventricular afterload will cause $E_a$ to change proportionally. If ventricular afterload increases, the LVEDP will rise while decreasing SV. This causes the ventricle to generate more pressure before opening the aortic valve. As such, $E_a$ can also be approximated as the slope of the end-systolic pressure (LVESP)-stroke volume (SV) relationship of the PV loop. Since LVESP=$E_a$×SV, LVESP can be rewritten as follows:

$$LVESP=R_t\times SV\times\{t_S+\tau(1-\exp(-t_d/\tau))\} \qquad \text{(Equation 19b)}.$$

Therefore, LVESP can be uniquely determined by arterial properties, time intervals, and SV. LVESP can be determined without the need to take into account the preload and inotropic state. For example, in the case that $\tau$>>$t_d$ and the denominator of the LVESP→T (=$t_S$+$t_d$), LVESP can be computed as:

$$LVESP=R_t\times SV\times T \qquad \text{(Equation 19c)}.$$

Once LVESP is calculated, LVEDV and LVESV are calculated using:

$$LVEDV=SV/LVEF \qquad \text{(Equation 20), and}$$

$$LVESV=LVEDV\times(1-LVEF) \qquad \text{(Equation 21)}.$$

LVEDP, LVESP, LVEDV and LVESV are used to measure the slopes of EDPVR and ESPVR at 554.

In one embodiment, the slopes of EDPVR and ESPVR can be measured using:

$$EDPVR=LVEDP/(SV/LVEF) \qquad \text{(Equation 22), and}$$

$$ESPVR=LVESP/(SV/LVEF-SV) \qquad \text{(Equation 23)}.$$

As described, the above system employs a workflow that can simultaneously collect various physiological data including pressure pulse waveforms and bioimpedance and ECG/EKG waveforms for early detection of HF events. For example, hemodynamic and bioimpedance parameters as well as vital signs can be extracted from the various waveforms detected.

With respect to pulse waveform which, in this case, is governed by LV hemodynamics, the systemic arteries and their interactions, it contains information about these separate systems and their optimum coupling during healthy and pathological states. For example, for the heart and arterial system; optimum coupling occurs when minimum energy is wasted to convert LV systolic ejection to forward flow and PW in the systemic circulation for perfusion.

A recent study has shown that IF parameters such as $\omega_1$, $\omega_2$, and $\Delta\omega_L$ which are derived from the carotid artery pulse waveform are closely correlated to the risk of incident CVD outcomes and HF events. For example, higher $\omega_1$ (the IF of the coupled heart and arterial system during systole) and higher $\Delta\omega_L$ (total frequency variation) are associated with a higher risk for incident HF with systolic dysfunction. In the case of healthy patients with ventricular-arterial coupling, it was observed that $\Delta\omega_L$ (=$\omega_1$−$\omega_2$) was about zero. However, $\Delta\omega_L$ was significantly higher among older individuals and those with prevalent HF.

During systole, the LV-arterial coupled system has a dominant frequency $\omega_1$ about which the instantaneous frequency oscillates. This frequency is primarily dominated by cardiac function. HF with reduced ejection fraction (HFrEF) and HF with preserved ejection fraction (HFpEF) are progressive pathological states of aberrant cardiac function and sub-optimum UV-arterial coupling associated with poor outcomes, including death. For example, in HFrEF, arterial elastance is elevated but LV systolic elastance is reduced, leading to worse LV-arterial coupling. However, unlike HFrEF, which is characterized by LV dilation and LV systolic dysfunction, HFpEF is associated with LV diastolic dysfunction. In HFpEF, both atrial and ventricular elastances are elevated, which may help to preserve LV-arterial coupling. As such, left ventricular end-systolic volume (LVESV) is a reliable predictor of new-onset HFpEF. Enlargement of LVESVI has significant prognostic power for adverse events even in patients with LVEF $\geq$50%. For example, an enlargement of LVESVI exceeding 24.1 ml/m$^2$ is associated with the future occurrence of adverse events in such patients. Furthermore, it has been found that elevation of $\omega_1$ and $\Delta\omega$ precedes HF clinical presentation and may represent preclinical markers for HF, indicating nascent impaired coupling of the LV-arterial system.

After the aortic valve closes, the heart and aorta are decoupled. The dominant frequency, in this case, is dictated only by the dynamics of the arterial system. The frequency $\omega_2$ represents the IF of the decoupled vasculature during diastole. In the IF model, lower $\omega_2$ was associated with a higher risk for incident HF. Since the aorta is the largest artery and is coupled directly to the LV, it dominates the wave dynamics (and pulsatile load) that the heart experiences. A lower $\omega_2$ is observed with increasing age among healthy individuals, and $\omega_2$ was significantly lower among those with hypertension and peripheral artery disease (compared with healthy individuals). As such, lower $\omega_2$ may indicate early vascular remodeling associated with age, such as aortic stiffness and hypertension, which can elevate the exposure of the heart to pressure pulsatility. Although pulsatile load contributes modestly to the total energy of the heart, the abnormal pulsatile load can contribute to the development of ventricular remodeling and progression to HF. For example, HF may be determined or modeled from the relationship between Ifs and excessive pressure pulsatility resulting from abnormal blood pressure elevation and arterial stiffness.

Figure 5B:
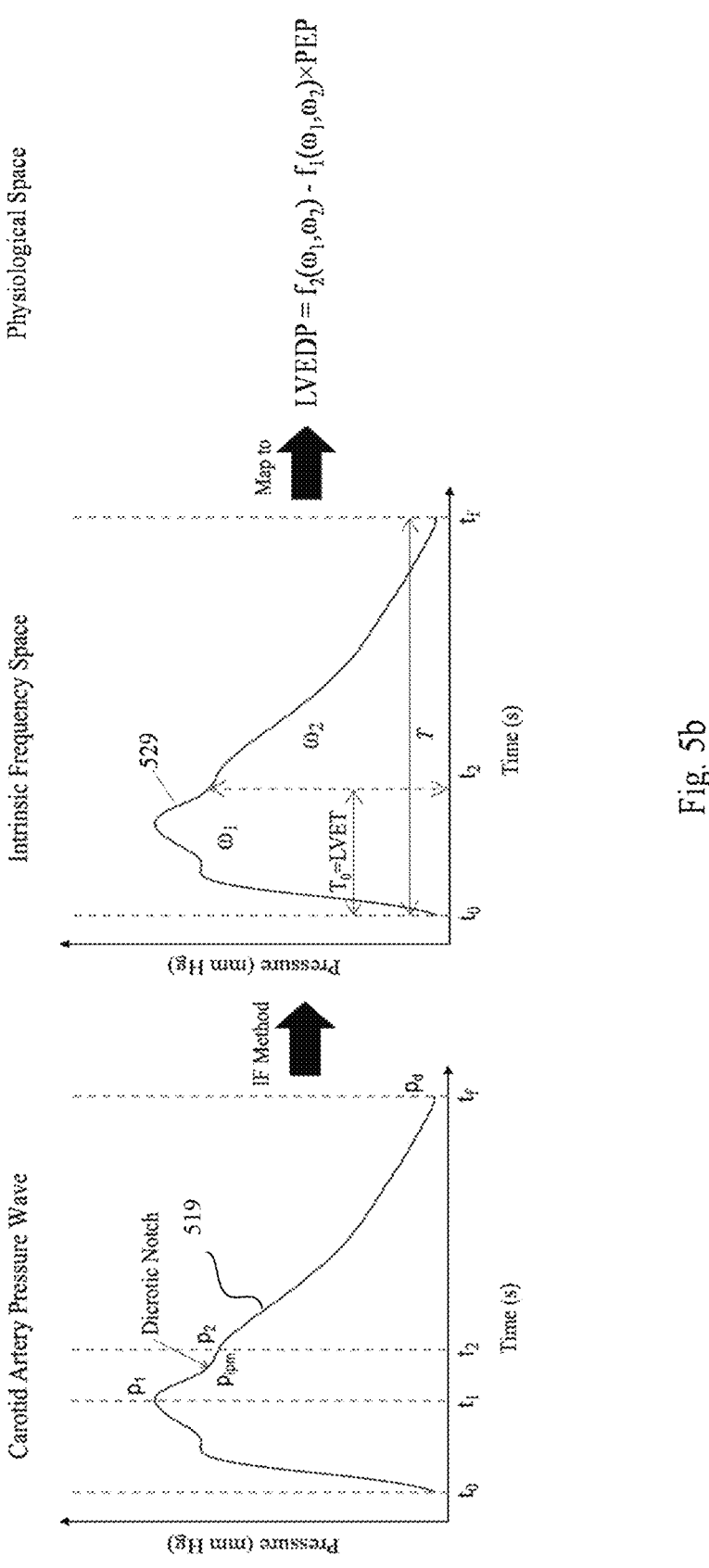
FIG. 5b illustrates obtaining IF parameters from the arterial waveform and mapping them to the physiological space.

FIG. 5$b$ illustrates determining intrinsic frequency (IF) space parameters from a carotid artery pressure waveform 519 of one cardiac cycle. The carotid artery pressure waveform plots the arterial pressure (v-axis) over time (x-axis) of one cardiac cycle. As shown, the cardiac cycle of the carotid artery pressure waveform includes systolic peak $p_1$ and diastolic peak $p_2$. The systolic peak has a higher pressure than the diastolic peak. For example, the pressure rises at time $t_0$ (beginning of the cardiac cycle) to $p_1$ at $t_1$, the first peak over time, falls to inter-peak minimum pressure $p_{ipm}$, rises to $p_2$ at $t_2$, and then falls to a minimum pressure at $t_f$ (end of the cardiac cycle).

The carotid artery pressure waveform is converted to an IF waveform 529. The systolic peak pressure of the IF waveform is equal to the IF parameter $\omega_1$ and the diastolic peak is equal to the IF parameter $\omega_2$. The time it takes from $t_0$ to reach the minimum pressure (dicrotic notch) between $\omega_1$ and $\omega_2$ is equal to $T_0$, which is equal to LVET while the end of the cardiac cycle is equal to T. The IF parameters can be mapped to the physiological space in which LVEDP=$f_2$ $(\omega_1,\omega_2)-f_1(\omega_1,\omega_2)\times$PEP.

Figure 6:
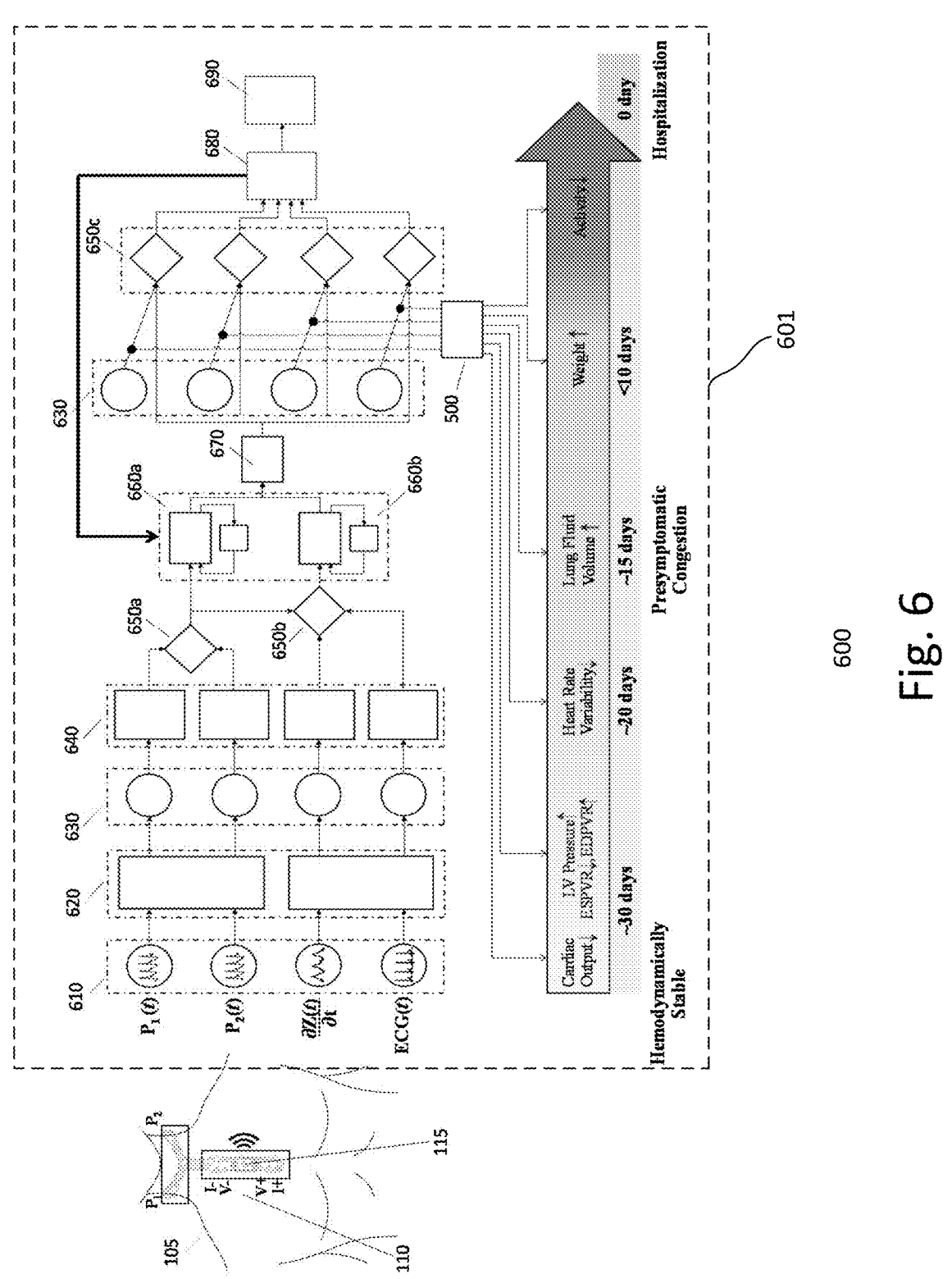
FIG. 6 shows an embodiment of a system for predicting heart failure events (HFE) using an exemplary wearable monitoring device.

FIG. 6 shows an embodiment of a system 600 for predicting worsening of HF leading to hospitalization. The system 600, in one embodiment, includes a wearable device 110. The wearable device 110 is the wearable device described in FIGS. 3$a$-3$c$, which is also similar to the wearable device described in FIGS. 2$a$-2$c$. Common elements may not be described or described in detail.

As shown, the wearable device includes a flexible patch body 110 that is worn on an upper part of the chest of a patient (user) 105. The flexible patch body forms, for example, a T-shaped upper portion of the patch body at the first end of the central body member. For example, the flexible patch body includes first extension portions extending bilaterally from about the first end of the central body member. In some embodiments, the wearable device may include winged extensions (not shown) that extend bilaterally from the second end of the central body member to form a T-shaped lower portion of the patch body. Other shaped forms of the patch body may also be useful.

In one embodiment, the flexible patch body is configured to collect physiological data 610 from the user. For example, the patch body includes dry conductive electrodes, such as bioimpedance electrodes for measuring both ECG/EKG and thoracic bioimpedance (Z)/impedance cardiograph ($\partial Z/\partial t$) waveforms. In addition, the patch body also includes pressure sensor arrays which detect the arterial pressure waveforms $P_1$ and $P_2$ from the left and right common carotid arteries of the user. The sensors and electrodes are disposed on the back surface of the patch body, contacting the user's skin. The wearable device may also include an optical sensor system along with a plurality of photodiodes and LED(s) for measuring photoplethysmography waveform from the midsternal region of the user's chest.

The wearable device may include a processing unit 115 located on the patch body. The processing unit receives acquired data from the wearable device, which includes carotid artery pressure waveforms $P_1$ and $P_2$ along with thoracic bioimpedance signals, ECG/EKG and PPG waves. The processing unit transmits the data (pre-processed data) to a server of the system via WiFi or cellular systems for analysis. The server, for example, is a backend server residing on the cloud. The backend server includes a predictor system 601. The predictor system, for example, includes a deep learning model configured to predict parameters of the user for several or multiple days in the future from the pre-processed data. For example, the predicted parameters predicted by the system include behavior of $P_1$, $P_2$, thoracic bioimpedance and ECG waveforms. These predicted parameters may indicate whether the patient is likely to suffer a heart failure event (HFE) or not.

In one embodiment, the deep learning model for predicting the heart failure events (HFE) satisfies the following requirements:
  a) ability to account for the time-series characteristics of the physiological waveforms,
  b) ability to express diversity of patients' physical conditions,
  c) ability to simultaneously evaluate multiple types of physiological waveforms, and
  d) ability to determine gradual abnormalities in the predicted waveforms in the time period between euvolemia and presymptomatic congestion.

In one embodiment, the deep learning (prediction) model includes various modules. The modules may be hardware, software or a combination thereof. In one embodiment, the model includes a waveform predictor module 620, a computational module 640, comparator engines 650$a$, 650$b$ and 650$c$, recurrent neural network (RNN) based learning modules 660$a$ and 660$b$, an anomaly detector 680, and an alert module 690. Providing other types or numbers for the modules may also be possible. The modules are configured to process the input waveforms generated from the wearable device. Based on the results, the system evaluates or predicts the heart failure events (HFE) of the user.

As shown, the waveforms 610 obtained from the wearable device is first processed by the waveform predictor module 620. The pressure pulse wave obtained from the right carotid artery is referred to as $P_1$, $P_2$ is the pressure pulse wave obtained from the left carotid artery and $\partial Z/\partial t$ refers to the first derivative of the TBI waveform. The input waveforms 610 include, for example, continuous real-time waveforms for the last several days obtained from the wearable patch worn by the heart failure patient.

The waveform predictor module 620 is a predictive machine learning (ML) model that takes the waveforms obtained over the past several days as input and uses it to predict the waveforms 630 the patient is likely to develop over the next few days. In one embodiment, the ML model performs re-processing of the pre-processed data to generate predicted waveforms. Reprocessing includes noise removal, feature extraction, missing value interpolation as well as other re-processing processes. Depending on the diversity of the waveforms' characteristics, some of the waveform predictors may have a cascaded or an ensemble architecture. In one embodiment, the waveform predictor module may be a convolutional neural network (CNN) based period classification algorithm (PCA) to detect periodic datasets. For waveforms with periodic features obtained from wearable sensors embedded in the patch, the PCA utilizes input waveforms 610 as training material and classifies predicted waveforms 630 accordingly based on their periods. It is observed that the PCA can achieve high accuracy, for example, up to 100% accuracy, in the case of low noise periodic time-series data. Other types of module may also be useful.

Subsequently, the computational module 640 takes the predicted waveforms 630 as inputs and uses the characteristic points of all the four types of waveforms to calculate the relevant parameters of the respective waveforms. Output of the computational module 640 are fed to the comparator engines 650a and 650b. While 650a represents a stochastic comparison between any characteristic point such as systolic peak/inflexion point/dicrotic notch/diastolic peak on the predicted left carotid pressure waveform and the corresponding point on the predicted right carotid pressure waveform at each consecutive cardiac cycle, 650b represents a stochastic comparison between any characteristic point such as P, Q, R, S, T waves on the predicted EGC waveform and the corresponding point on the predicted ∂Z/∂t waveforms at each consecutive cardiac cycle. Next, the stochastic inter-dependent relationship between the characteristic points of the two pressure waveforms and the one between ECG and ∂Z/∂t are fed to two recurrent neural network (RNN) based learning modules 660a and 660b, respectively. The stochastic relation between the characteristic points obtained from the predicted waveforms at successive cardiac cycles will be used as the base for learning by the machine learning model. With each consecutive cycle, the model is updated with new data and with constant learning and validation. At the time of validation, the learning modules take input from the succeeding stages (n+1$^{th}$ period, say) to predict the data at the n$^{th}$ period (where n∈I, I being any integer) to ensure proper learning and internal correction as and when required (a back-and-forth learning and validation process). Subsequently, the output (i.e., the baseline parameters) from the two RNN based learning modules are combined to find out the interdependent relationship among them at each consecutive cycle and thus the baseline model 670 of a patient is generated.

The baseline model 670 includes the parametric variations that are naturally occurring. For example, variations may occur due to the changing physiological conditions in response to metabolic needs, activity, environment, diurnal cycles, as well as other factors. The variations may also be due to worsening of heart failure or even due to other healthcare system factors, such as suboptimal care at the skilled nursing facilities. Upon the formation of the baseline model for each patient, the characteristic points obtained from the predicted waveforms 630 for each patient are then compared against their respective baseline model parameters 670 to determine the changes in their cardiovascular or circulatory conditions.

In one embodiment, comparator engines 650c compares the characteristics points obtained from the predicted waveforms 630 with the baseline model parameters 670. For example, four comparator engines are provided, each one comparing the characteristic points obtained from the respective predicted waveform with the baseline model parameters. Because the changes in the predicted hemodynamic and impedance waveforms will cause a change in each patient's baseline characteristics, it is essential to understand the reason behind such variations, i.e., whether it is being caused due to worsening heart failure conditions, due to suboptimal care post-discharge, or due to any environmental factor. To understand the reason behind such variations, the predictor system 601 uses an anomaly detector 680 to determine the abnormalities in the patient's predicted parameters compared to their baseline parameters and subsequently generates an alert 690 if an anomaly is detected. For example, detected abnormalities in the parameters obtained from the predicted waveforms trigger an alert rather than passing it on as just a concept drift where a gradual change in baseline occurs due to some environmental events. Determining whether the patient is at risk of a possible hospitalization or not, depends entirely on the performance of anomaly detector module 680.

To validate the estimated baseline parameters, a feedback loop is created from the anomaly detector module 680 to the RNN based learning modules 660a and 660b. This means that the predicted parameters that are being compared to the baseline parameters are once more going through the stages of validation to provide feedback and ensure correct baseline prediction. The loop is closed and a back and forth one. If abnormalities are detected, then an alert 690 is triggered. Accordingly, the patient is instructed to visit the physician. This forms the workflow of using the system 600 for early detection of HF events, which aims at reducing the hospitalizations of HF patients by preventing the patients from reaching a critical stage.

In one embodiment, the predicted waveforms 630 are processed through the software flow 500 to calculate the clinical parameters for next few days. These include left ventricular (LV) hemodynamic parameters along with ECG/EKG and TBI parameters for the next few days. For example, the software flow computes left ventricular (LV) physiological parameters such as LVET and PEP at every cycle which are further utilized to derive LVEF. In addition, the software flow may also compute LV IF parameters (i.e., $\omega_1$ and $\omega_2$) which are used to calculate LV end-diastolic pressure and volume along with ESPVR and EDPVR at every period. As for the TBI parameters, they may include base impedance $Z_b$, $\Delta Z/\Delta t$, respiratory rate (RR), extracellular fluid (ECF) and intravascular fluid (IVF) at every cycle which along with the other parameters are used to predict SV and CO respectively.

Any changes in the predicted parameters over time is used to evaluate if the patient is hemodynamically stable (euvolemia) or if there is any presymptomatic congestion followed by clinical congestion that leads to acute decompensation. This is characterized by an increase in cardiac output and LV pressure along with reduction in ESPVR or an increase in EDPVR (hemodynamic congestion) followed by increase in sympathetic nervous activity that signifies a reduction in heart rate variability. This is followed by an increase in the lung fluid volume (presymptomatic congestion) and finally to an increase in weight and a decrease in activities (clinical congestion). Therefore, decongestive therapy should be started as soon as possible and titrated according to clinical response. Notably, decongestive therapy should be continued beyond the improvement of symptoms and clinical evidence of organ congestion and is maintained until euvolemia is achieved. Note that there is a large individual variability in the time course of decompensation, even for the same patient. Thus, several patterns may precede a decompensation.

Figure 7A:
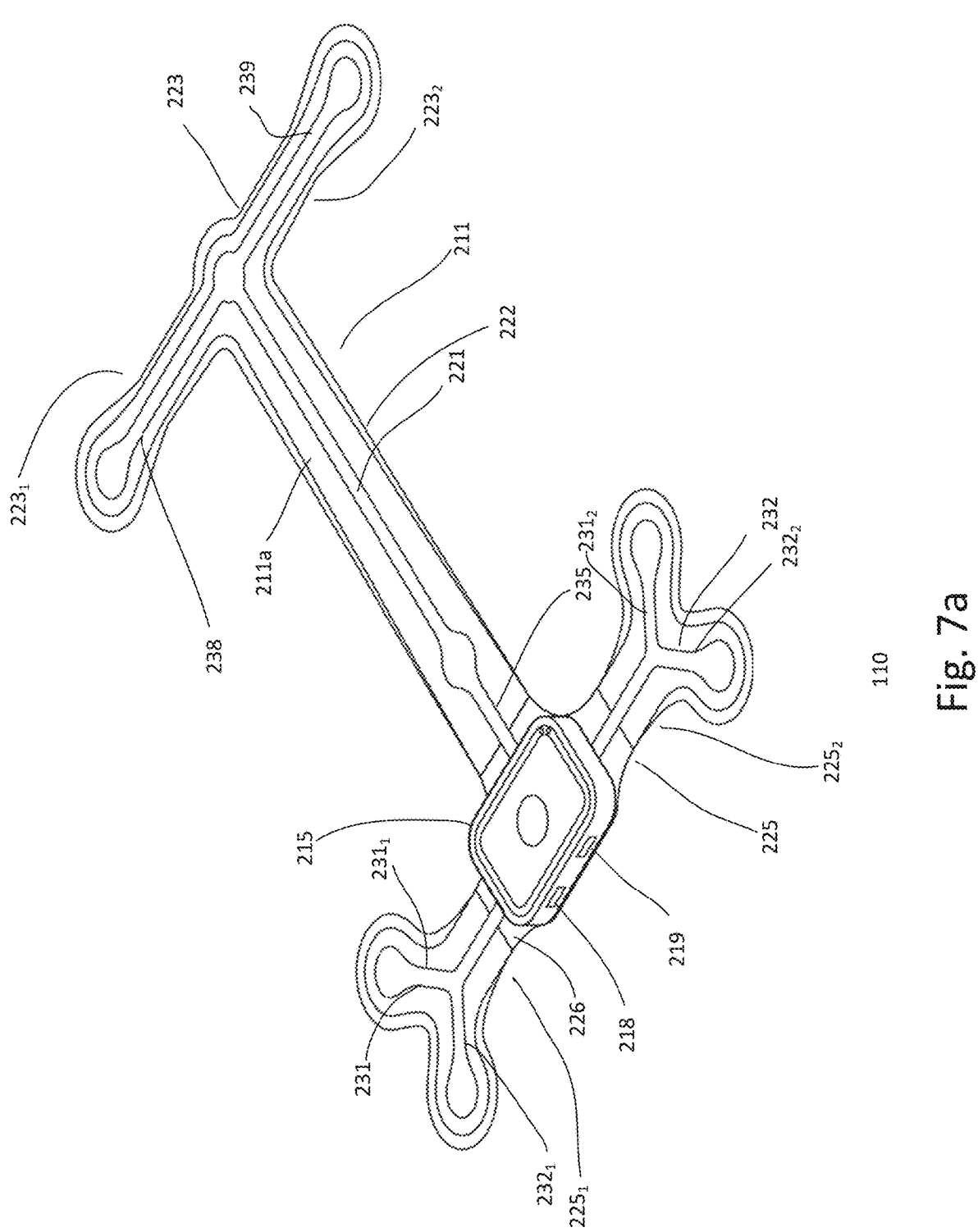
FIGS. 7a-7b show different views of another embodiment of a wearable monitoring device.
Figure 7B:
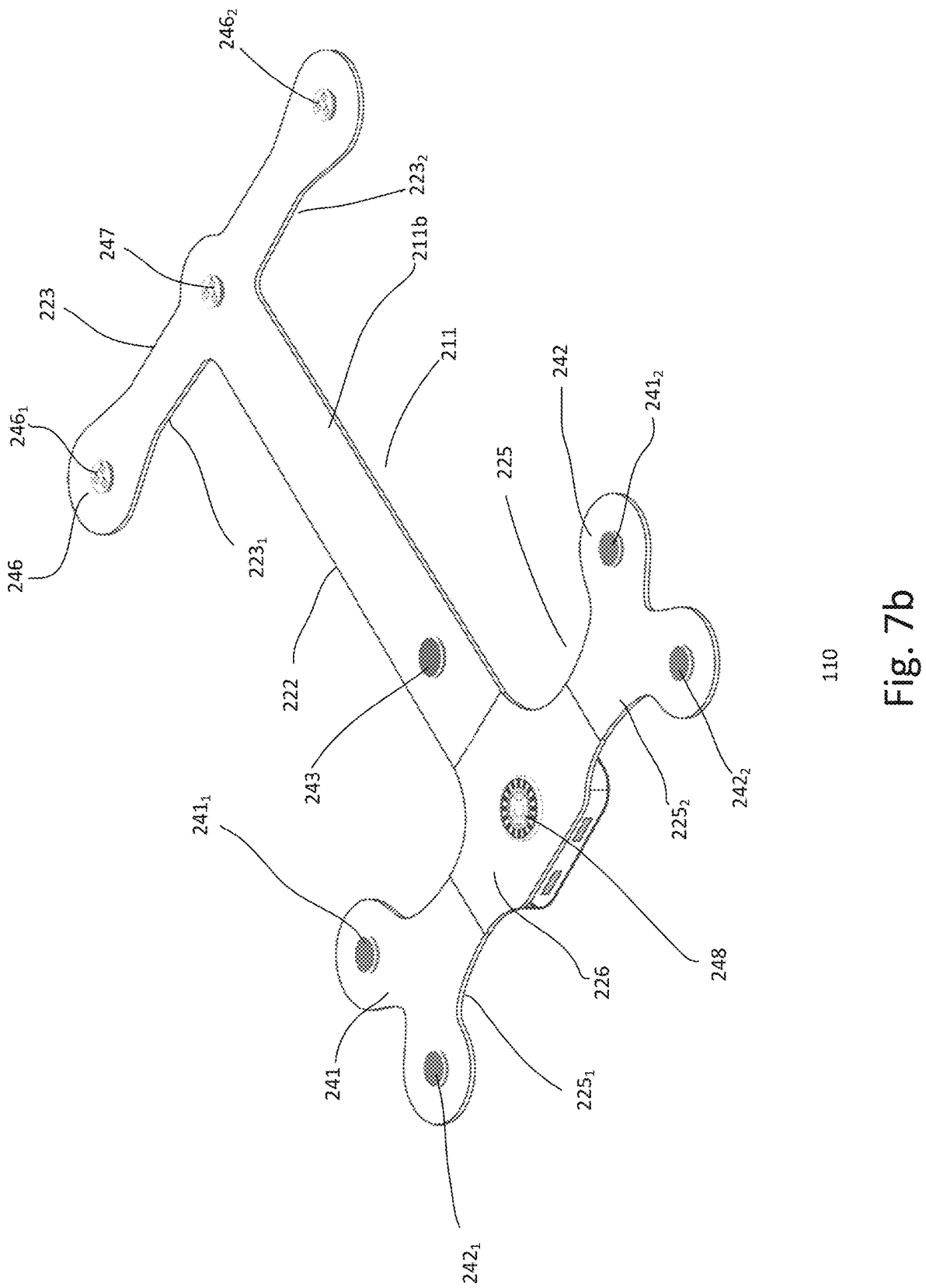

FIGS. 7a-7b show various views of another embodiment of a wearable device 110. In particular, FIG. 7a shows a 3D front perspective view and FIG. 7b shows a 3D back perspective view skin side. As shown, the wearable device is a patch which includes various components for monitoring HF of a user. The wearable device 110 is similar to that described in FIGS. 2a-2c. Common elements may not be described or described in detail.

In one embodiment, the wearable device includes a flexible patch body 211. The flexible patch body conforms to the body contour of the user when worn. The flexible patch body includes front and back patch body surfaces 211a and 211b. The back patch body surface contacts the skin of the user. The back body surface includes an adhesive layer for attaching to the user's skin.

In one embodiment, the patch body is formed from multiple layers. In one embodiment, the patch body includes upper and lower substrate layers sandwiching the signal trace unit. For example, the signal trace unit is embedded between the top and bottom substrate layers. The top substrate layer may serve as the front patch surface and the bottom substrate layer may serve as the back patch surface.

In one embodiment, the patch body includes an elongated central body member 222 having first and second central member ends. The flexible patch body includes first extensions 223 extending laterally from about the first end of the central body member. For example, the first extensions include a first extension portion $223_1$ extending from the central body member in a first lateral direction and a second extension portion $223_2$ extending from the central body member in a second lateral direction, which is opposite the first lateral direction. This forms, for example, a T-shaped upper portion of the patch body at the first end of the central body member.

The flexible patch body, in one embodiment, includes wing extensions 225 extending laterally from about the second end of the central body member. The wing extensions include a first wing extension portion $225_1$ extending from the central body member in the first lateral direction and a second wing extension portion $225_2$ extending from the central body member in the second lateral direction. The wing extensions extending from the second end of the central body member form a lower portion of the patch body. The wing extensions similarly form a T-shaped lower portion in which the ends are winged tipped. Other shaped wing extensions may also be useful.

The patch body includes a trace unit 221 which includes electronic traces or conductive wires. The trace unit, for example, is a flexible trace unit. The flexible trace unit, for example, is disposed between the top and bottom substrate layers of the patch body. The trace unit includes pressure sensor interfaces 258 for connecting to the pressure sensor arrays or pressure sensors and electrode interfaces 259 for connecting to the electrodes. The term pressure sensor may refer to a pressure sensor or a pressure sensor array.

In one embodiment, the pressure sensor arrays or pressure sensors include first and second pressure sensor arrays or pressure sensors $246_{1-2}$ positioned at the first and second extension portions and a third pressure sensor array or pressure sensors 247 positioned therebetween. The first and second pressure sensor arrays or pressure sensors $246_{1-2}$, for example, are configured to measure pressure pulse waveforms from the common carotid arteries of the user. As for the third pressure sensor array or pressure sensors 247, it is configured to monitor pressure pulse waveform from the anterior jugular vein of the user. For example, the third pressure sensor array or pressure sensors 247 determines jugular venous pulse (JVP) waveform. Providing other types of sensors such as PPG sensors for monitoring the anterior jugular vein of the user may also be useful. Employing a PPG sensor can be more advantageous as it is user friendly and is able to record continuously for long periods of time. Through the monitoring of both the carotid arteries and the anterior jugular vein of the user, the wearable device is able to capture both left ventricular (LV) and right ventricular (RV) hemodynamics simultaneously along with bioimpedance parameters. As a result, both right heart and left heart failure symptoms can be detected early for treatment, avoiding unnecessary adverse medical complications and lowers the risk of hospitalization.

The electrodes, on the other hand, are positioned at the first and second wing extension portions. For example, the first wing extension portion accommodates a first set of bioimpedance electrodes $241_1$ and $242_1$ and the second wing extension portion accommodates a second set of bioimpedance electrodes $241_2$ and $242_2$. Apart from bioimpedance electrodes, the electrodes may also include a RLD electrode 243 disposed on the central body member and proximate to the wing extensions.

In one embodiment, each set or pair of electrodes includes a first or input electrode 241 ($241_1$ for the first electrode pair and electrode $241_2$ for the second electrode pair) and a second or output electrode 242 ($242_1$ for the first electrode pair and electrode $242_2$ for the second electrode pair). For example, a positive current (I+) is injected at the input electrode $241_1$ of the first set of bioimpedance electrodes and a positive voltage (V+) is measured by the output electrode $242_1$ of the first set of bioimpedance electrodes; a negative current (I−) is injected at the input electrode $241_2$ of the second set of bioimpedance electrodes and a negative voltage (V−) is measured by the output electrode $242_2$ of the second set of bioimpedance electrodes. The output or voltage electrodes of the first and second sets of bioimpedance electrodes are configured to measure both ECG/EKG waveforms and bioimpedance waveforms simultaneously. As shown, the current electrodes are disposed above the voltage electrodes when the patch is worn. As for the RLD electrode, it is for measuring RLD voltage ($V_{RLD}$). Other arrangements or configurations for the electrodes may also be possible.

The pressure sensors and electrodes are disposed on the back surface of the patch to enable contact with the user's skin. The electrodes may be dry electrodes and the pressure sensors may be MEMS pressure sensors or fabric pressure sensors, as previously described. Other types of electrodes or pressure sensors may also be useful.

The trace unit includes a bottom PCB and main PCB connectors. Signal traces are provided to connect respective electrodes and pressure sensors or pressure sensor arrays to the bottom PCB. For example, bioimpedance electrode signal traces 231 and 232 are connected to the first and second set of bioimpedance electrodes (electrode signal traces $231_1$ and $232_1$ for the first set of bioimpedance electrodes and electrode signal traces $231_2$ and $232_2$ for the second set of bioimpedance electrodes) while a RLD electrode signal trace 235 is connected to the RLD electrode 243. Pressure signal traces 238 and 239 are provided to connect the first, second and third pressure sensors $246_{1-2}$ and 247 to the bottom PCB.

As discussed, the signal traces may have different numbers of signal lines (including power signals, such as voltage or voltages and ground). The number of signal lines for the signal traces, for example, may depend on the types and configurations of the electrodes and sensors. For example, in the case of the pressure signal trace, it may include three signal lines, two voltage signal lines and a ground line to power a capacitance-to-digital converter (CDC) and a wireless transmission module. The pressure pulse signal is transmitted wirelessly to the main PCB by the wireless transmission module. As such, pressure signal lines are not needed. In other embodiments, the pressure pulse signal may be transmitted to the main PCB via SPI/I2C/GPIO/UART interfaces through the B-to-B connector or connectors. In such cases, the pressure signal trace includes an additional signal line. Other configurations of the signal traces of the trace unit may also be useful.

A rigid electronic housing 215 which houses a main PCB circuit board is disposed on the front patch body surface of the shoulder portion of the central body member between the first and second sets of bioimpedance sensors. In one embodiment, the electronic housing includes top and housing parts (not shown) encasing the main PCB circuit board. In one embodiment, the PCB connector or connectors connect the main PCB to the bottom PCB together. This enables signals from the electrodes and sensors from the bottom PCB to be pre-processed by the main PCB and transmitted to, for example, the user's mobile device for further transmission of the pre-processed data to the server for processing. As for data from the pressure sensors, it can be transferred directly to the main PCB through the wireless communication module. In the case that wireless communication is not available, the pressure sensor data may be transferred to the main PCB via SPI/I2C/GPIO/UART interfaces through the B-to-B connector or connectors.

The electronic housing also includes an on-off switch 218 for switching on the wearable device to collect and transmit data as well as a charge port 219. The charge port, for example, may be a USB port. The charge port is used to charge a battery disposed in the electronic housing for operating the patch.

In one embodiment, a PPG sensor 248 is disposed on the back patch body surface in the shoulder portion 226 of the central body member. The PPG sensor, for example, is coupled to the bottom PCB. The PPG sensor, for example, is an optical sensor system along with a plurality of photodiodes and one or more light-emitting diodes (LEDs) for detecting the PPG signal. Similar to the pressure sensor data, data from the PPG sensor is transferred directly to the main PCB through the wireless communication module. Alternatively, it can be sent first to the bottom PCB by digital peripherals before it is transmitted via the B-to-B connector to the microcontroller in the main PCB.

Although the above describes the wearable device as having a single patch body, it is understood that the wearable device may include a patch body which has multiple distinct body portions. In some embodiments, the multi-portion patch body of the wearable device may include two patch body portions. For example, the central body member, extensions and wing extensions are arranged to form two patch body portions. In one embodiment, a first end portion of the central body member with the extensions forms a single neck patch body portion and a second end portion of the central body member with the wing extensions forms a distinct chest patch body portion. In one embodiment, the main PCB is part of the chest patch body portion and a separate battery module is provided in the neck patch body portion for powering the sensors of the neck patch body portion. Data from the sensors of the neck patch body portion are communicated to the main PCB wirelessly. Providing distinct patch body portions advantageously enables the patch body portions to be worn separately by a patient. For example, the neck patch body portion which accommodates the pressure sensor arrays may be worn by the patient a few times a day to measure pressure pulse waveforms. As for the chest patch body portion with the electrodes, it may be worn continuously by the patient on the midsternal line to measure ECG and thoracic bioimpedance waveforms. Having other numbers of the patch body portions or configurations of the wearable device may also be useful.

In yet another embodiment, the central body member, extensions and wing extensions are arranged to form four patch body portions. For example, a first end portion of the central body member with the extensions forms distinct left, right and middle neck patch body portions. The left neck patch body portion includes the left pressure sensor array configured to be disposed on the left common carotid artery while the right neck patch body portion includes the right pressure sensor array configured to be disposed on the right common carotid artery. As for the middle neck patch body portion, it includes the middle pressure sensor array configured to be disposed on the anterior jugular vein. The other end portion (or second end portion) of the central body member with the wing extensions forms a distinct chest patch body portion. The main PCB is included on the chest patch body portion. Separate battery modules are included in the left, right and middle neck patch body portions for operating the sensors. The left, right and middle neck patch body portions, in one embodiment, are configured to transmit the pressure sensor data to the main PCB via wireless communication i.e. via BLE or EQS-HBC modules. The neck and chest patch body portions can be worn separately by a patient. For example, the neck patch body portions which accommodate the pressure sensor arrays may be worn by the patient a few times a day to measure pressure pulse waveforms. As for the chest patch body portion with the electrodes, it may be worn continuously by the patient on the midsternal line for continuous measurement of ECG and thoracic bioimpedance waveforms. Other configurations of wearing the patch body portions may also be useful.

Figure 8A:
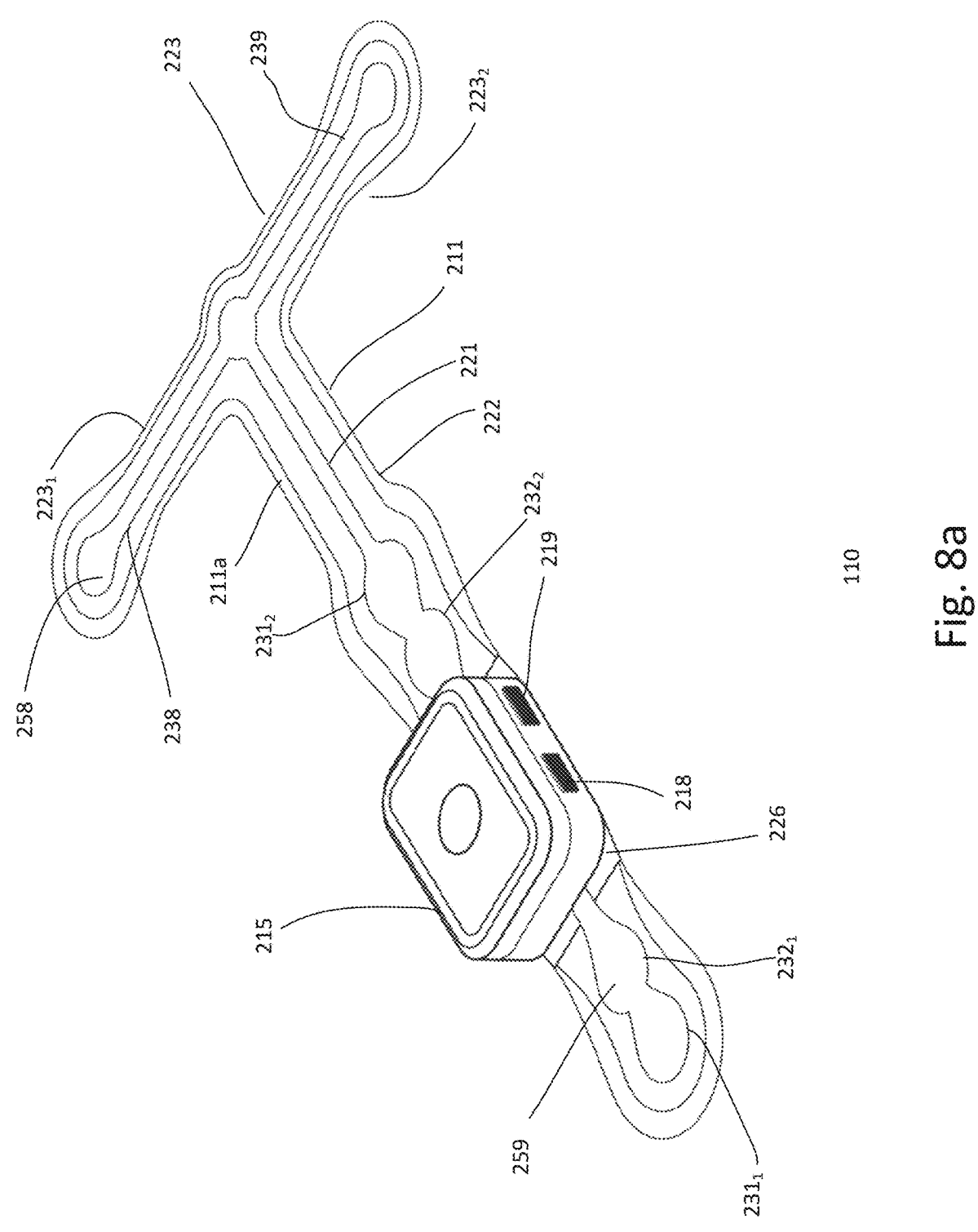
FIGS. 8a-8b show different views of another embodiment of a wearable monitoring device.
Figure 8B:
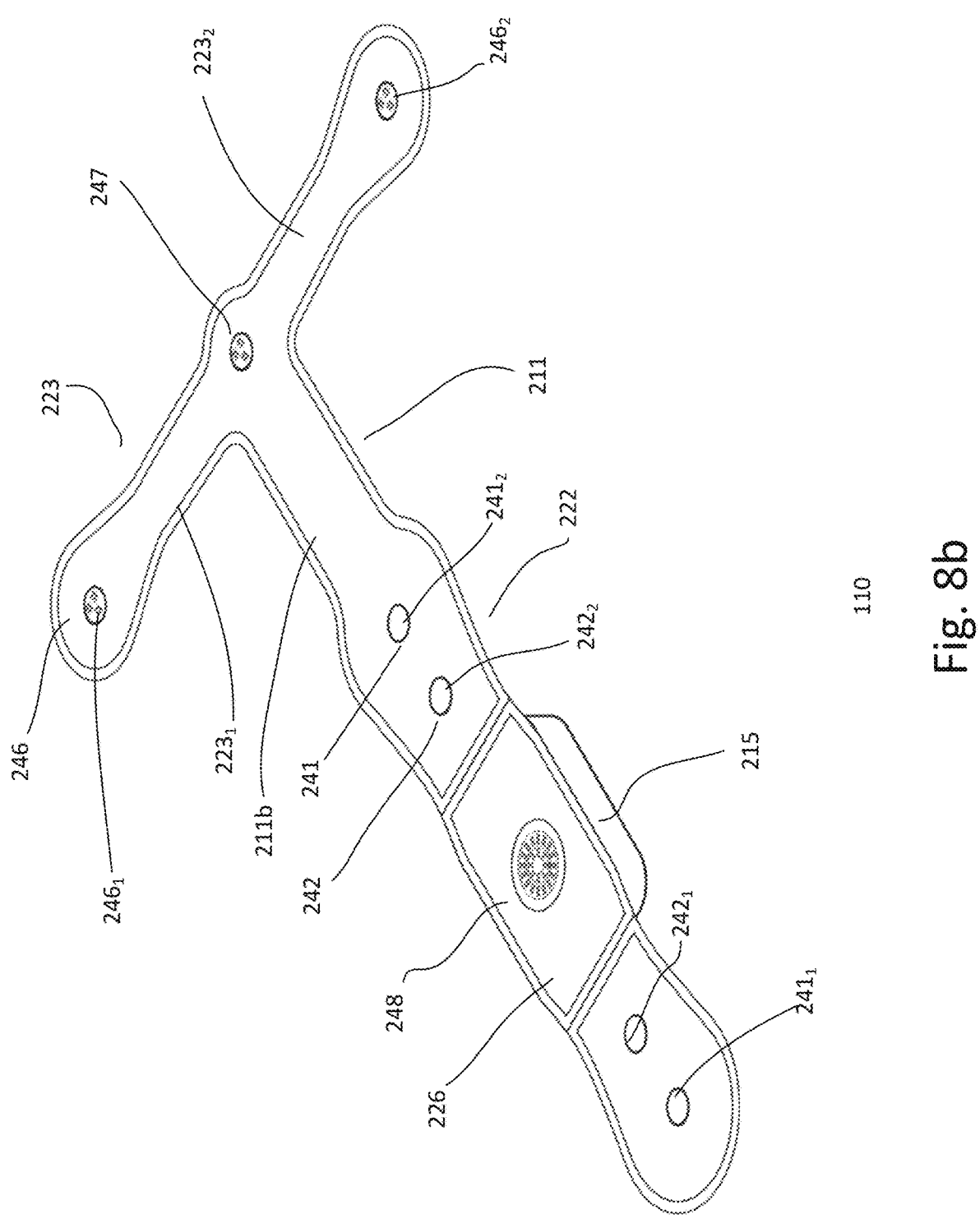

FIGS. 8a-8b shows various views of another embodiment of a wearable device 110. In particular, FIG. 8a shows a 3D front perspective view and FIG. 8b shows a 3D back perspective view skin side. As shown, the wearable device is a patch which includes various components for monitoring HF of a user. The wearable device 110 is similar to that described in FIGS. 7a-7b. Common elements may not be described or described in detail.

In one embodiment, the wearable device includes a flexible patch body 211. The flexible patch body conforms to the body contour of the user when worn. The flexible patch body includes front and back patch body surfaces 211a and 211b. The back patch body surface contacts the skin of the user. The back body surface includes an adhesive layer for attaching to the user's skin.

In one embodiment, the patch body is formed from multiple layers. In one embodiment, the patch body includes upper and lower substrate layers sandwiching the signal trace unit. For example, the signal trace unit is embedded between the top and bottom substrate layers. The top substrate layer may serve as the front patch surface and the bottom substrate layer may serve as the back patch surface.

In one embodiment, the patch body includes an elongated central body member 222 having first and second central member ends. The flexible patch body includes first extensions 223 extending laterally from about the first end of the central body member. For example, the first extensions include a first extension portion 223₁ extending from the central body member in a first lateral direction and a second extension portion 223₂ extending from the central body member in a second lateral direction, which is opposite the first lateral direction. This forms, for example, a T-shaped upper portion of the patch body at the first end of the central body member. Unlike the patch body of FIGS. 7a-7b, no wing extensions are provided at the second end of the central body member.

The patch body includes a trace unit 221 which includes electronic traces or conductive wires. The trace unit, for example, is a flexible trace unit. The flexible trace unit, for example, is disposed between the top and bottom substrate layers of the patch body. The trace unit includes pressure sensor interfaces 258 for connecting to the pressure sensor arrays or pressure sensors and electrode interfaces 259 for connecting to the electrodes. The term pressure sensor may refer to a pressure sensor or a pressure sensor array.

As shown, the pressure sensor arrays or pressure sensors include first and second pressure sensor arrays or pressure sensors 246₁₋₂ configured to monitor activities of the carotid artery of the user and a third pressure sensor array or pressure sensor 247 for monitoring the activities of the anterior jugular vein of the user. Providing other types of sensors such as photoplethysmography (PPG) sensors for monitoring the anterior jugular vein of the user may also be useful. The pressure sensors and electrodes are disposed on the back surface of the patch to enable contact to the user's skin. Unlike the patch body of FIGS. 7a-7b, there is no RLD electrode. Instead, the RLD input terminal of the ECG analog frontend, such as the AD8233/AD8232 is connected to the ground. As such, no separate RLD electrode is needed. The electrodes may be dry electrodes and the pressure sensors may be MEMS pressure sensors or fabric pressure sensors, as previously described. Other types of electrodes or pressure sensors may also be useful.

The trace unit includes a bottom PCB and main PCB connectors. Electrode signal traces 231₁₋₂ and 232₁₋₂ connect electrodes to the bottom PCB and pressure signal traces 238 and 239 for the neck PCBs mounting first and second pressure sensors or pressure sensor arrays 246 to the bottom PCB. For example, a first set of electrode signal traces 231₁ and 232₁ connects a first set of bioimpedance electrodes 241₁ and 242₁ to the bottom PCB and a second set of electrode signal traces 231₂ and 232₂ connects a second set of bioimpedance electrodes 241₂ and 242₂ to the bottom PCB. Pressure signal traces 238 and 239 are provided to connect the neck PCBs mounting the first, second and third pressure sensors 246₁₋₂ and 247 to the bottom PCB.

In one embodiment, a positive current (I+) is injected to the user through the first electrode 241₁ of the first set of bioimpedance electrodes and a positive voltage (V+) is measured at the second electrode 242₁ of the first set of bioimpedance electrodes; a negative current (I−) is injected through the first electrode 241₂ of the second set of bioimpedance electrodes and a negative voltage (V−) is measured at the second electrode 242₂ of the second set of bioimpedance electrodes. For example, the current electrodes (I+ and I− electrodes) 241₁₋₂ serve as input electrodes and the voltage electrodes (V+ and V− electrodes) 242₁₋₂ serve as output electrodes. The voltage electrodes of the first and second sets of bioimpedance electrodes are configured to measure both ECG/EKG waveforms and bioimpedance waveforms simultaneously. As shown, the I+ electrode (or 241₁) is disposed below the V+ electrode (or 242₁) and the I− electrode (or 241₂) is disposed above the V− electrode (or 242₂). Other configurations of the electrodes may also be useful.

A rigid electronic housing 215 which houses a main PCB circuit board is disposed on the front patch body surface of the shoulder portion of the central body member between the first and second sets of bioimpedance sensors. In one embodiment, the electronic housing includes top and housing parts (not shown) encasing the main PCB circuit board. In one embodiment, the PCB connectors connect the main PCB to the bottom PCB together. This enables signals from the electrodes and sensors from the bottom PCB to be pre-processed by the main PCB and transmitted to, for example, the user's mobile device for further transmission of the pre-processed data to the server for processing. As for data from the pressure sensors, it can be transferred directly to the main PCB through the wireless communication module. In the case that wireless communication is not available, the pressure sensor data may be transferred by, for example, digital peripherals such as SPI/I2C/GPIO/UART interfaces from the flexible neck PCB to the bottom PCB and then via the B-to-B connector to the microcontroller in the main PCB.

The electronic housing also includes an on-off switch 218 for switching on the wearable device to collect and transmit data as well as a charge port 219. The charge port, for example, may be a USB port. The charge port is used to charge a battery disposed in the electronic housing for operating the patch.

In one embodiment, a PPG sensor 248 is disposed on the back patch body surface in the shoulder portion 226 of the central body member. The PPG sensor, for example, is coupled to the bottom PCB. The PPG sensor, for example, is an optical sensor system along with a plurality of photodiodes and one or more light-emitting diodes (LEDs) for detecting the PPG signal. Similar to the pressure sensor data, data from the PPG sensor is transferred directly to the main PCB through the wireless communication module. Alternatively, it can be sent first to the bottom PCB by digital peripherals before it is transmitted via the B-to-B connector to the microcontroller in the main PCB.

Although the above describes the wearable device having a single patch body, it is understood that the wearable device may include a patch body which has multiple distinct body portions. In some embodiments, the multi-portion patch body of the wearable device may include two patch body portions. For example, the central body member with extensions is arranged to form two patch body portions. In one embodiment, a first end portion of the central body member with the extensions forms a single neck patch body portion. The elongated portion of the central body member forms a distinct chest patch body portion. In one embodiment, the main PCB is part of the chest patch body portion and a separate battery module is provided in the neck patch body portion for powering the sensors of the neck patch body portion. Data from the sensors of the neck patch body portion are communicated to the main PCB wirelessly. Providing distinct patch body portions advantageously enables the patch body portions to be worn separately by a patient. For example, the neck patch body portion which accommodates the pressure sensor arrays may be worn by the patient a few times in a day to measure pressure pulse waveforms. As for the chest patch body portion with the electrodes, it may be worn continuously by the patient on the midsternal line to measure ECG and thoracic bioimpedance waveforms. Having other numbers of the patch body or configurations of the wearable device may also be useful.

In yet another embodiment, the central body member with extensions are arranged to form four patch body portions. For example, a first end portion of the central body member with the extensions forms distinct left, right and middle neck patch body portions. The left neck patch body portion includes the left pressure sensor array configured to be disposed on the left common carotid artery while the right neck patch body portion includes the right pressure sensor array configured to be disposed on the right common carotid artery. As for the middle neck patch body portion, it includes the middle pressure sensor array configured to be disposed on the anterior jugular vein. An elongated portion of the central body member forms a distinct chest patch body portion. The main PCB is included on the chest patch body portion. Separate battery modules are included in the left, right and middle neck patch body portions for operating the sensors. The left, right and middle neck patch body portions, in one embodiment, are configured to transmit the pressure sensor data to the main PCB via wireless communication, e.g., via BLE or EQS-HBC modules. The neck and chest patch body portions can be worn separately by a patient. For example, the neck patch body portions which accommodate the pressure sensor arrays may be worn by the patient a few times in a day to measure pressure pulse waveforms. As for the chest patch body portion with the electrodes, it may be worn continuously by the patient on the midsternal line for continuous measurement of ECG and thoracic bioimpedance waveforms. Other configurations of wearing the patch body portions may also be useful.

Figure 9:
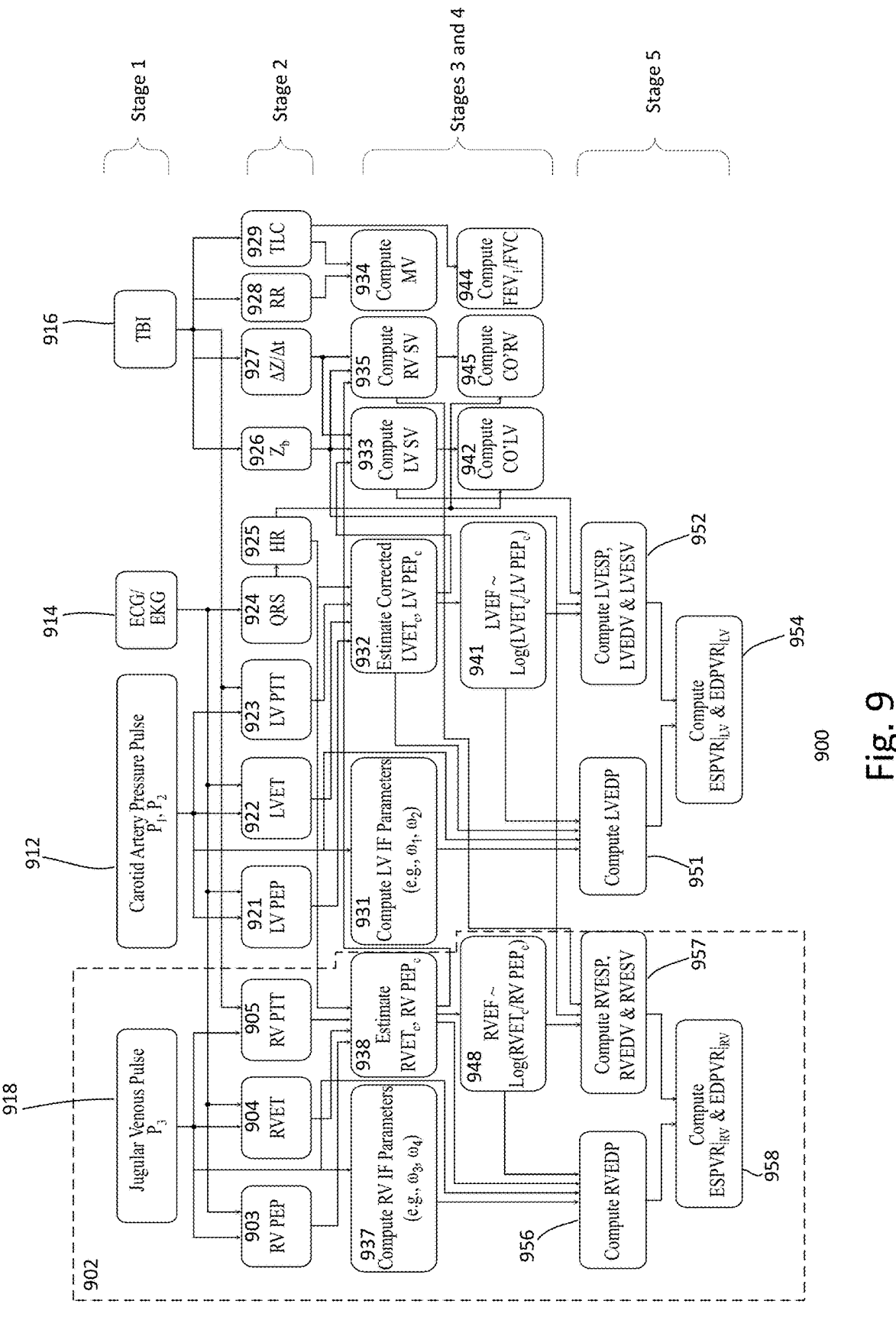
FIG. 9 shows a flow for calculating LV and RV hemodynamic and vital parameters.

FIG. 9 shows a software flow 900 for extracting clinical parameters from data measured from the sensors and electrodes of the wearable device. The wearable device is similar to that described in FIGS. 7a-7b and FIGS. 8a-8b. In particular, the wearable device further includes a pressure sensor array or a plurality of PPG sensors for measuring the anterior jugular venous pulse. Clinical parameter extraction, in one embodiment, is performed by a server, such as a cloud server. For example, preprocessed data from the wearable device is transmitted to the user's mobile device and then transmitted to the server. Alternatively, the preprocessed data from the wearable device may be directly transmitted to the server. For example, the main PCB may include a mobile communication module, such as a GSM module, enabling the preprocessed data to be transmitted to the cloud server via a cellular network. The flow, for example, may be performed by a software application running on the server.

The flow is similar to that of FIG. 5a except that it additionally includes processing to extract clinical parameters related to the right side of the heart from data measured from the sensors and electrodes of the wearable device. For example, a majority of the processing is included within block 902 (dotted lines) of the flow. Common steps or processes may not be described or described in detail.

The flow, for example, may include multiple stages for processing the data collected from the wearable device. As shown, the flow includes 5 stages (stage 1 to stage 5). Providing a flow with other numbers of stages may also be useful.

At stage 1 or the input stage, physiological or input data collected from the wearable device is received. In one embodiment, carotid artery pressure pulse data (wave or waveform) $P_1$ and $P_2$ from the pressure sensor arrays is received at 912, jugular venous pulse data $P_3$ from the jugular pressure sensor array or, PPG sensor(s) at 918, ECG/EKG data from the V+, V− and RLD electrodes is received at 914 and TBI data from the I+, V+, I−, V− electrodes is received at 916.

The flow employs the input data to automatically measure systolic time intervals (STI) using ECG/EKG, carotid artery pressure pulse and TBI waveforms and determines, among other things, heart rate (HR), HRV, QRS duration, left and right ventricular pre-ejection period (LV PEP and RV PEP), left and right ventricular ejection time (LVET and RVET), and left and right ventricular pulse transit time (LV PTT and RV PTT) and displaying the corrected systolic time intervals, estimation of LVEF and RVEF in HF patients and constructing the LV and RV pressure-volume slopes.

At stage 2, the input data is employed to calculate right ventricular pre-ejection period (RV PEP) at 903, right ventricular ejection time (RVET) at 904, right ventricular pulse transit time (RV PTT) at 905, left ventricular pre-ejection period (LV PEP) at 921, left ventricular ejection time (LVET) at 922, left ventricular pulse transit time (LV PTT) at 923, along with QRS duration ($QRS_d$) at 924, heart rate (HR) at 925, thoracic base impedance ($Z_b$) at 926, impedance cardiography $\Delta Z/\Delta t$ at 927, respiratory rate (RR) at 928, and thoracic lung capacity (TLC) at 929.

The flow continues to stages 3 and 4. In one embodiment, the flow computes left ventricular intrinsic frequency (LF IF) or, left contractility parameters (for example, $\omega_1$, $\omega_2$, and $\Delta\omega_L$) at 931, estimates corrected $LVET_c$ and left ventricular (LV) $PEP_c$ at 932, calculates LV SV at 933, calculates RV SV at 935 and computes minute ventilation (MV) at 934.

In addition, right ventricular IF (RV IF) or right contractility parameters (for example, $\omega_3$, $\omega_4$, and $\Delta\omega_R$) are computed at 937 and $RVET_c$ and RV $PEP_c$ are estimated at 938.

The RV IF parameters, in one embodiment, include $\omega_3$, $\omega_4$, and $\Delta\omega_R$, where $\omega_3$ describes the dynamics of the systolic phase of the cardiac cycle when the right ventricle (RV) and pulmonary artery (PA) are coupled and $\omega_4$ belongs to the diastolic phase when RV and PA are decoupled. $\Delta\omega_R$ represents the difference ($=(-\omega_3)-(-\omega_4)$), between $\omega_3$ and $\omega_4$. The RV IF parameters are, for example, calculated from $P_3$. For example, $\omega_3$ and $\omega_4$ may be obtained using an IF algorithm that uses the information stored in the jugular pressure waveform to create a multidimensional function. The IF algorithm, in one embodiment, models a coupled RV-PA system. The IF algorithm is based on, for example, an L2-minimization that uses the jugular venous pulse waveform to compute the RV IF parameters such as $\omega_3$ and $\omega_4$.

As shown, LVEF is calculated at 941 from, for example, the corrected LVET i.e., $LVET_c$ and corrected LV PEP i.e., LV $PEP_c$. Likewise, RVEF is calculated at 948 from $RVET_c$ and RV $PEP_c$. At 942, LV cardiac output (CO'LV) is computed at 942 from LV SV and HR while CO'RV is computed at 945 from RV SV and HR.

At 945, $FEV_1/FVC$ ratio is computed from TLC. FEV (Forced expiratory volume) measures the amount of air that can be forced from the lungs in one second and FVC (Forced Vital Capacity) is the largest amount of air that can be forcefully exhaled after breathing in as deeply as possible. Lower $FEV_1$ indicates more significant obstruction while a lower than normal FVC reading indicates restricted breathing. While congestive heart failure contributes to significant $FEV_1$ reduction, the computation of $FEV_1/FVC$ ratio is a standard parameter used for the diagnosis of respiratory diseases such as chronic obstructive pulmonary disease (COPD), is an index independent of concomitant heart function impairment and may be regarded as a measure of comorbidity of heart failure.

At stage 5, LVEDP is calculated at 951 and LVESP, LVEDV and LVESV are calculated at 952. The information from 951 and 952 are employed to compute ESPVR and EDPVR for the left ventricle of the heart. Similarly, the RVEDP is calculated at 956 and RVESP, RVEDV and RVESV are calculated at 957. The information from 956 and 957 are used to compute the ESPVR and EDPVR for the right ventricle of the heart.

As described, unlike FIG. 5*a*, the system of FIG. 9 not only collects pulse waveform data governed by LV hemodynamics, but also those governed by the RV hemodynamics. For example, the system detects carotid artery waveforms governed by LV hemodynamics and jugular venous pulse waveform governed by RV hemodynamics. As a result, the system enables early detection of both LHF and RHF events.

For example, the LV IF parameters ($\omega_1$, $\omega_2$, and $\Delta\omega_L$) derived from the carotid artery pulse waveforms are found to be closely correlated to the risk of possible HF events (HFE), in particular, higher LHF risks. Higher $\omega_1$ and $\Delta\omega_L$ are associated with a higher risk of LHF. For example, in the case of healthy or young patients with ideal LV-arterial coupling, it was observed that $\Delta\omega_L$ was about zero. However, $\Delta\omega_L$ was significantly higher among older individuals and those with existing LHF conditions. As such, an elevation of $\omega_1$ and $\Delta\omega_L$ may precede LHF clinical presentation to represent preclinical markers for LHF, indicating nascent impaired coupling of the LV-arterial system. Aside from higher $\omega 1$ and $\Delta\omega_L$, a lower $\omega_2$ may be associated with a higher risk for patients with possible HF events (HFE). For example, $\omega_2$ was significantly lower among those with hypertension and peripheral artery disease compared to healthy individuals. Lower $\omega_2$ implies early vascular remodeling, based on aortic stiffness and hypertension, which can lead to an elevated exposure of the heart to pressure pulsatility, thus causing a higher risk of LHF.

As for RV IF parameters ($\omega_3$, $\omega_4$, and $\Delta\omega_R$) derived from the jugular venous pulse waveform having signal traces being opposite to those of the carotid artery pressure waveforms, are postulated to be closely associated to risks of RHF. For example, higher negatives of $\omega_3$ or lower $\omega_3$ and $\Delta\omega_R$ are associated with higher risks of RHF. For example, in the case of healthy or young patients with ideal RV-RA coupling, it is predicted that $\Delta\omega_R$ ($=\omega_4-\omega_3$) is about zero. It is postulated that if the system computes a reduction in $\omega_3$ and $\Delta\omega_R$, it may precede RHF clinical presentation to represent preclinical markers for RHF, indicating a nascent impaired coupling of the RV-PA system. In addition, lower negatives of $\omega_4$ or higher $\omega_4$ may also be associated with higher risks of RHF. For example, $\omega_4$ is predicted to be significantly higher among those with pulmonary artery disease and pulmonary hypertension compared to healthy individuals.

To summarize, computed values having higher $\omega_1$ and lower $\omega_2$ may relate to a higher risk of LHF while lower $\omega_3$ and higher $\omega_4$ may relate to a higher risk of RHF and pulmonary hypertension. This, therefore, facilitates the determination of RHF and LHF events using the same device.

Figure 10:
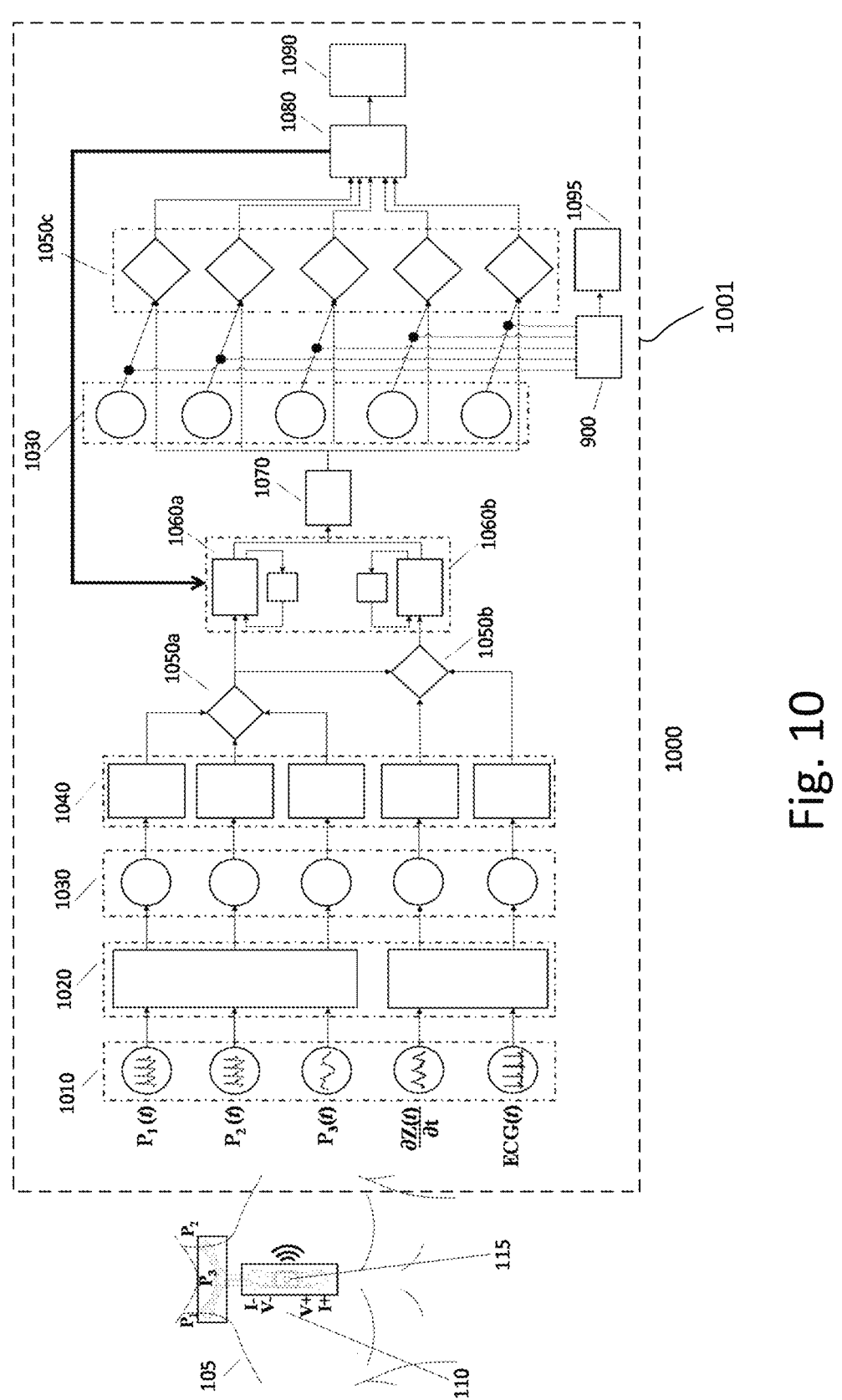
FIG. 10 shows another embodiment of a system for predicting heart failure events (HFE) using an exemplary wearable monitoring device.

FIG. 10 shows another embodiment of a system 1000 with a wearable device 110 for predicting HF. The system is similar to that described in FIG. 6. For example, the system includes the wearable device and a backend server which processes the data collected from the wearable device and outputs analyzed results. Common elements may not be described or described in detail.

As shown, the wearable device includes a flexible patch body 110 that is worn on an upper part of the chest of a patient (user) 105. The flexible patch body forms, for example, a T-shaped upper portion at the first end of the central body member and a T-shaped lower portion at the second end of the central body member. For example, the flexible patch body is similar to that described in FIGS. 7*a*-7*b*. In some embodiments, the flexible patch body may not include a T-shaped lower portion, such as that described in FIGS. 8*a*-8*b*. Other shaped forms of the patch body may also be useful.

In one embodiment, the flexible patch body is configured with electrodes and sensors for collecting physiological data from the user. For example, the patch body includes dry conductive electrodes such as bioimpedance electrodes for measuring both ECG/EKG and bioimpedance waveforms. In addition, the patch body also includes pressure sensor arrays for detecting the arterial pressure waveform $P_1$ and $P_2$ of the user from the common carotid arteries and also the jugular venous pressure waveform $P_3$ of the user from the anterior jugular vein. Utilizing other types of electrodes and sensors may also be possible. For example, a PPG sensor may be employed instead for measuring the jugular venous pressure waveform. The sensors and electrodes are disposed on the back surface of the patch body, contacting the user's skin. The wearable device may also include an optical sensor system along with a plurality of photodiodes and LED(s) for measuring photoplethysmography waveform from the midsternal region of the user's chest.

The wearable device may include a processing unit 115 located on the patch body. The processing unit receives acquired data from the wearable device, which includes carotid artery pressure waveforms $P_1$ and $P_2$, jugular veneous pressure waveform $P_3$, along with thoracic bioimpedance signals, ECG/EKG and PPG waves. The processing unit transmits the data (pre-processed data) to a server of the system via WiFi or cellular systems for analysis. The backend server, for example, resides on the cloud. The backend server includes a predictor system 1001. The predictor system is configured to predict parameters of the user for several or multiple days in the future from the pre-processed data. For example, the predicted parameters predicted by the system include the behaviour of $P_1$, $P_2$, $P_3$, thoracic bioimpedance and ECG waveforms. These predicted parameters may indicate whether the patient is likely to suffer a heart failure event (HFE) or not.

The predictor system, in one embodiment, includes a deep learning model for predicting the heart failure events (HFE). In one embodiment, the deep learning model includes various modules, such as a waveform predictor module 1020, a computational module 1040, comparator engines 1050*a*, 1050*b* and 1050*c*, recurrent neural network (RNN) based learning modules 1060*a* and 1060*b*, an anomaly detector 1080, and an alert module 1090. Providing other types or numbers for the modules may also be possible. Data from the wearable device may be sent via WiFi or cellular systems to the backend server for processing by the modules. Based on the results, the system evaluates or predicts possible heart failure events (HFE) of the user.

As shown, waveforms 1010 obtained from the wearable device is first processed by the waveform predictor module 1020. The pressure pulse waveforms obtained from the right carotid artery (P1), the left carotid artery (P2), the anterior jugular vein (P3) and the first derivative of the TBI ($\partial Z/\partial t$) are provided as input waveforms 1010. The input waveforms 1010 include, for example, continuous real-time waveforms for last several days obtained from the wearable patch worn by the heart failure patient. The waveform predictor module 1020 is a predictive machine learning (ML) model that takes the waveforms from the past several days as input and processes them to predict the waveforms 1030 that the patient is likely to develop over the next few days.

In one embodiment, the ML model performs re-processing of the pre-processed data to generate predicted waveforms. Re-processing includes noise removal, feature extraction, missing value interpolation as well as other re-processing processes. Depending on the diversity of the waveforms' characteristics, some of the waveform predictors may have a cascaded or an ensemble architecture. In one embodiment, the waveform predictor module may be a convolutional neural network (CNN) based period classification algorithm (PCA) to detect periodic datasets. For waveforms with periodic features obtained from wearable sensors embedded in the patch, the PCA utilizes input waveforms 1010 as training material and classifies predicted waveforms 1030 accordingly based on their periods. Other types of module may also be useful.

Subsequently, the computational module 1040 takes the predicted waveforms 1030 as inputs and uses the characteristic points of all the five types of waveforms, such as, $P_1$, $P_2$, $P_3$, $\partial Z/\partial t$ and ECG, to calculate the relevant parameters of the respective waveforms. Output of the computational module 1040 are fed to the comparator engines 1050a and 1050b. While 1050a represents a stochastic comparison between any characteristic point such as systolic peak/inflexion point/dicrotic notch/diastolic peak on the predicted left carotid pressure wave and the corresponding points on the predicted right carotid pressure wave and the predicted jugular venous wave at each consecutive cardiac cycle, 1050b represents a stochastic comparison between any characteristic point such as P, Q, R, S, T waves on the predicted EGC wave and the corresponding point on the predicted EZ/at wave at consecutive cardiac cycle. Next, the stochastic interdependent relationships among the characteristic points of the three pressure waveforms and the one between ECG and TBI are fed to two recurrent neural networks (RNN) based learning modules 1060a and 1060b, respectively. The stochastic relationship between the characteristic points obtained from the predicted waveforms at successive cardiac cycles will be used as the base for learning by the machine learning model. With each consecutive cycle, the model gets updated with new data and with constant learning and validation. At the time of validation, the learning modules take input from the succeeding stages (n+1$^{th}$ period, say) to predict the data at the n$^{th}$ period (where n∈I, I being any integer) to ensure proper learning and internal correction as and when required (a back-and-forth learning and validation process). Subsequently, the output (i.e., the baseline parameters) from the two RNN based learning modules are combined to find out the interdependent relationship among them at different cycles and thus the baseline model 1070 of a patient is generated.

The baseline model 1070 includes the parametric variations that are naturally occurring. For example, variations may occur due to the changes in physiological conditions in response to metabolic needs, activity, environment, diurnal cycles, as well as other factors. The variations may also be due to worsening of heart failure or other healthcare system factors, such as suboptimal care in the skilled nursing facilities. Upon the formation of the baseline model for each patient, the characteristic points obtained from the predicted waveforms 1030 for each patient are then compared against their respective baseline model parameters 1070 to determine the changes in their cardiovascular or circulatory conditions.

In one embodiment, comparator engines 1050c compares the predicted waveforms 1030 with the baseline model parameters 1070. For example, four comparator engines are provided, each one comparing the characteristic points obtained from its respective predicted waveform with the baseline model parameter. Because the changes in the predicted hemodynamic and impedance waveforms will cause a change in each patient's baseline characteristics, it is essential to understand the reason behind such variations, i.e., whether it is being caused due to worsening heart failure conditions or, due to suboptimal care post-discharge, or if it is due to some non-harmful environmental factors. To understand the reason behind such variations, the model 1000 uses an anomaly detector 1080 to determine the abnormalities in the patient's predicted parameters compared to their baseline parameters and subsequently generates an alert 1090 if an anomaly is detected. For example, detected abnormalities in the parameters obtained from the predicted waveforms trigger an alert rather than passing it on as just a concept drift where a gradual change in baseline occurs due to some environmental events. Determining whether the patient is at risk of a possible hospitalization or, not, depends entirely on the performance of anomaly detector module 1080.

To validate the estimated baseline parameters, a feedback loop is created from the anomaly detector module 1080 to the RNN-based learning modules 1060a and 1060b. This means that the predicted parameters that are being compared to the baseline parameters are once more going through the stages of validation to provide feedback and ensure correct baseline prediction. The loop is closed and a back and forth one. If abnormalities are detected, then an alert 1090 is triggered. Accordingly, the patient is instructed to visit the physician. This forms the workflow of using the system 1000 for early detection of HF events, which aims at reducing the hospitalizations of HF patients by preventing the patients from reaching an acute stage.

In one embodiment, the predicted waveforms 1030 is processed through the software flow 900 to calculate the clinical parameters 1095 for the next few days. The parameters include left ventricular (LV) and right ventricular (RV) hemodynamic parameters along with ECG/EKG and TBI parameters for the next few days. For example, the software flow computes left ventricular (LV) physiological parameters such as LVET and LV PEP at each cardiac cycle which are further utilized to derive LVEF, and right ventricular (RV) physiological parameters such as RVET, RV PEP at each cycle which are further utilized to derive RVEF. In addition, the software flow 900 may also compute LV IF parameters ($\omega_1$ and $\omega_2$) and RV IF parameters ($\omega_3$ and $\omega_4$) which are employed to determine ESPVR and EDPVR for both left and right ventricles at each cardiac cycle. As for the TBI parameters, they may include base impedance $Z_b$, $\Delta Z/\Delta t$, respiratory rate (RR), and total lung capacity (TLC) at every cycle which along with other parameters are used to predict minute ventilation (MV), $FEV_1/FVC$ ratio along with SV and CO for both left and right ventricles. Any change in the predicted parameters over time is evaluated to determine if the patient is hemodynamically stable (euvolemia) or or unstable, such as if there is any presymptomatic congestion followed by clinical congestion that leads to acute decompensation.

Among the patients who are at risk of heart failure (HF), they may also suffer from other complications, for example, respiratory infections such as COVID-19 or influenza like illness (ILI) or even other chronic respiratory diseases like chronic obstructive pulmonary disease (COPD) or Asthma. Furthermore, as SARS-COV-2 may cause HF with preserved ejection fraction or HFpEF, unmask subclinical HFpEF or exacerbate existing HFpEF in COVID-19 infected patients, these patients may display similar cardio-metabolic risk profiles as those with HFpEF.

In anticipation of this issue, the present system is configured to not just monitor HF patients, but also those who are suffering from respiratory infections or diseases. For example, the system simultaneously determines all the factors impacting RV and LV dysfunction along with Respiratory Rate (RR), Thoracic Lung Capacity (TLC), Minute Ventilation (MV), and $FEV_1/FVC$ ratio. Therefore, when the HF patients are infected by any virus affecting human cardiac and respiratory systems, the system will be able to effectively monitor or diagnose the infections.

Figure 11:
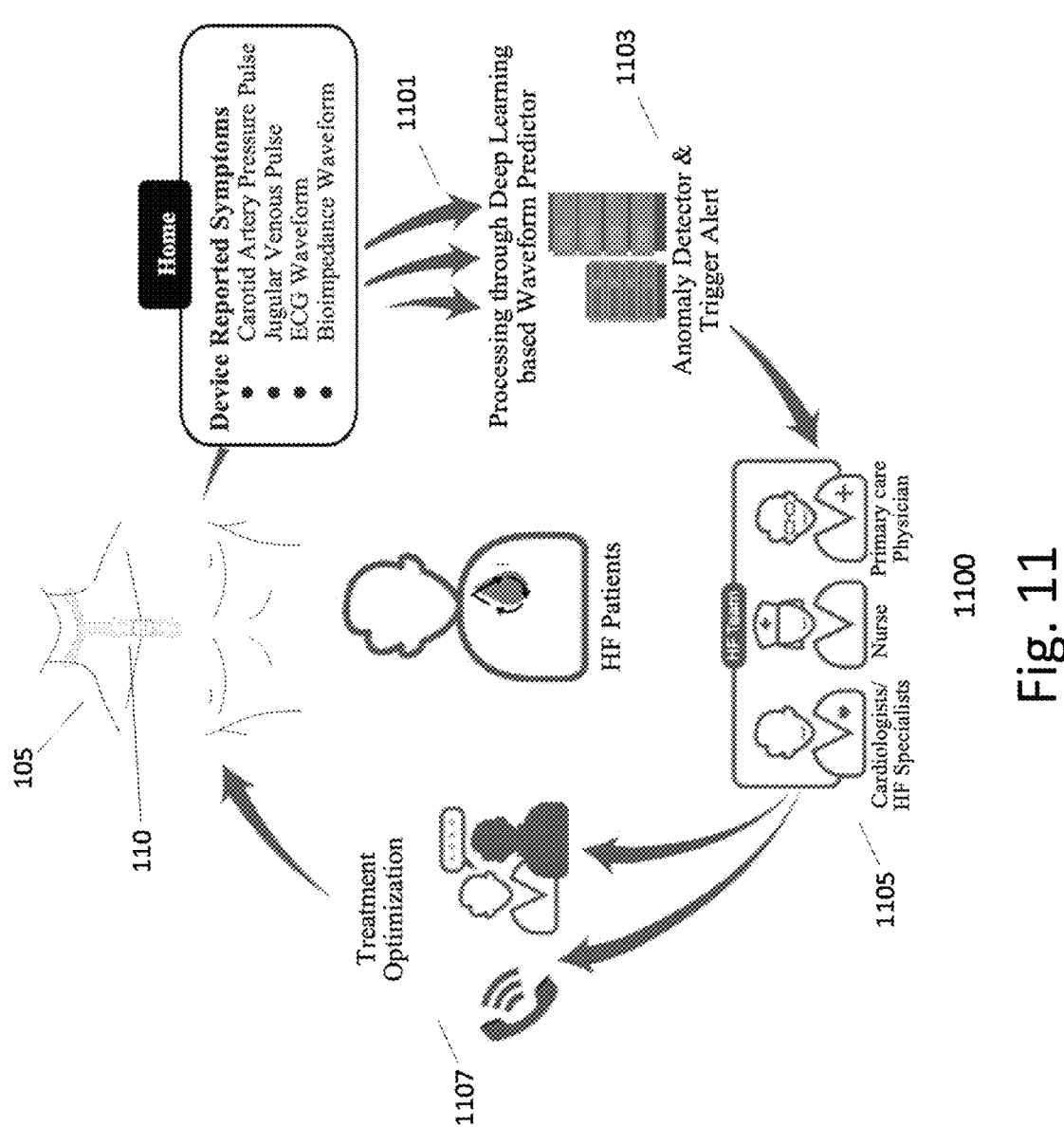
FIG. 11 illustrates an embodiment of a framework for monitoring HF.

FIG. 11 illustrates a framework for monitoring heart failure events (HFE) using an embodiment of a wearable monitoring device. The framework displays how remote patient monitoring can be performed on post-discharged patients to facilitate early detection of disease progression such as HF events.

As shown, the wearable device includes a flexible patch body 110 that is worn on the upper part of the chest of a patient (user) 105. The patch body may be configured with electrodes and sensors for collecting the physiological data of the user. For example, the electrodes and sensors serve to acquire ECG/EKG, bioimpedance waveforms as well as pressure pulse waveforms from the common carotid arteries and/or the anterior jugular vein of the user.

At 1101, the physiological data acquired from the patch worn by the user is sent to a server for processing and analysis. The server includes the deep learning model for predicting heart failure events (HFE) that works via generating a customized baseline model. The customized baseline model is based on predicting the behaviour of the waveforms obtained from the wearable patch multiple days ahead of actual hospitalization as well as calculating the future clinical parameters from the predicted waveforms. The baseline model is used for comparison with the parameters obtained from the predicted waveforms gathered by the patch to detect for changes in cardiovascular or circulatory conditions. The results are then reported to both the user and the physician of the user. For example, parameters such as LV pressure and volume, ejection fraction (EF), IF (contractility) parameters, fluid volume, SV, CO, and vital signs are displayed in the form of a dashboard.

Additionally, the user may be alerted at 1103 when abnormalities or heart deteriorations are detected. For example, the patient might show an anomaly in the predicted waveform. However, the anomaly in the predicted waveform is due to a gradual change in the baseline characteristics because of worsening of heart failure or due to healthcare system factors, such as suboptimal care in the skilled nursing facilities but not due to any non-harmful environmental factor. The alert may cause the user to be instructed or may instruct the user to visit the physician.

Upon being alerted, the user visits the physician at 1105. As a result, treatment can be timely administered at 1107 to prevent the user from reaching an acute stage. This in turn would vastly contribute to reduced hospitalizations, a significant reduction in healthcare expenditure and a controlled mortality rate of HF patients across the world. As such, a framework forming the basis for early detection of HF events is achieved.

The inventive concept of the present disclosure may be embodied in other specific forms without departing from the spirit or essential characteristics thereof. The foregoing embodiments, therefore, are to be considered in all respects illustrative rather than limiting the invention described herein.

The invention claimed is:

1. A wearable patch for monitoring heart failure comprising:
   a patch body for attaching to a body of a user to be monitored, the patch body includes a body patch side which contacts the body and an opposing non-body patch side;
   first and second carotid arterial pressure sensors on the body patch side, wherein the first and second carotid arterial pressure sensors are configured on the patch body side to measure arterial pressure from common carotid arteries of the user;
   first and second sets of bioimpedance electrodes on the patch body side, the first and second sets of bioimpedance electrodes are configured for current injection into the upper thoracic region of the user and voltage detection from the upper thoracic region of the user; and
   a controller disposed on the non-body patch side of the patch body, wherein the controller comprises,
      a data collection module, the data collection module is configured to receive data (received data) from the first and second carotid arterial pressure sensors and the first and second sets of bioimpedance electrodes,
      a processing module, the processing module is configured to preprocess the received data (preprocessed data),
      a communication module, the communication module is configured to wirelessly transmit the preprocessed data from the processing module to a backend analysis system for analyzing the preprocessed data from the communication module, and
      a power module, the power module is configured to provide power source to the data collection module, the processing module, and the communication module.

2. The wearable patch of claim 1, wherein the patch body comprises:
   an elongated central body member having first and second central member ends, wherein,
      the first central member end is configured to be located at a neck region of the user,
      the second central member end is configured to be located at a sternum region of the user, and
      the central body member is configured to accommodate the controller; and
   first and second extension portions extending from the first central body member end in first and second lateral directions, wherein the first and second extension portions are configured to accommodate the first and second carotid arterial pressure sensors.

3. The wearable patch of claim 2, wherein the second central member end comprises:
   a first wing extension extending in the first lateral direction from the second central body member end, the first wing extension is configured to accommodate the first set of bioimpedance electrodes; and
   a second wing extension extending in the second lateral direction from the second central body member end, the second wing extension is configured to accommodate the second set of bioimpedance electrodes.

4. The wearable patch of claim 3, wherein:

bioimpedance sensors of the first set of bioimpedance electrodes are configured longitudinally along a longitudinal axis of the central body member on the first wing extension; and bioimpedance sensors of the second set of bioimpedance electrodes are configured longitudinally along the longitudinal axis of the central body member on the second wing extension.

5. The wearable patch of claim 2, wherein:

the central body member is configured to accommodate the first and second sets of bioimpedance electrodes;

the first set of bioimpedance electrodes is disposed of on the central body member on a first side of the controller in a longitudinal axis of the central body member; and the second set of bioimpedance electrodes is disposed of on the central body member on an opposing second side of the controller in the longitudinal axis of the central body member.

6. The wearable patch of claim 1, wherein the transmission of the preprocessed data to the backend analysis system by the communication module is indirect (indirect communication), wherein the indirect communication comprises:

the preprocessed data is transmitted to a mobile device of the user;

forwarding the preprocessed data by the mobile device to the backend analysis system.

7. The wearable patch of claim 1, further comprises a trace unit, wherein the trace unit couples the controller to the first and second carotid arterial pressure sensors and the first and second sets of bioimpedance electrodes for supplying power thereto and receiving data therefrom.

8. The wearable patch of claim 1, wherein the body patch side comprises an adhesive for adhering to the user.

9. The wearable patch of claim 1, wherein the first and second carotid arterial pressure sensors comprise first and second sensor transmission modules for wirelessly transmitting arterial pressure data to the data collection module.

10. The wearable patch of claim 1, wherein the patch body comprises:

a flexible patch body;

a trace unit disposed on the body patch side of the flexible patch body, wherein the trace unit couples the controller which is disposed on the non-body patch side of the flexible patch body to the first and second carotid arterial pressure sensors and the first and second sets of bioimpedance electrodes for supplying power thereto and receiving data therefrom; and an adhesive body disposed on the body patch side of the flexible patch body and the trace unit.

11. The wearable patch of claim 1, further comprises:

an anterior jugular pressure sensor configured on the body patch side to measure jugular venous pulse (JVP) from an anterior jugular vein of the user; and wherein data from the anterior jugular pressure sensor is preprocessed by the processing module and forms part of the preprocessed data communicated to the backend analysis system by the communication module.

12. The wearable patch of claim 1, wherein the first and second carotid arterial pressure sensors comprise:

a first and a second capacitive pressure sensor arrays, wherein capacitive sensor elements are formed of a microelectromechanical sensor (MEEMS) elements; or a first and a second piezoresistive pressure sensors (or sensor arrays), wherein piezoresistive sensor elements are formed of a double-layered nanofiber woven fabric, such as poly (3,4-ethylenedioxythiophene) (PEDOT) conductive polymer and polyvinylidene difluoride (PVDF) piezoelectric polymer thin films; or a first and a second inorganic ferroelectric/piezoelectric pressure sensors (or sensor arrays), wherein ferroelectric/piezoelectric sensor elements are formed of a mechanical energy harvesting material such as lead zirconate titanate (Pb [ZrxTi1-x] O3, $0 \leq x \leq 1$ or, PZT) or, similar materials on a flexible and stretchable elastomer substrate connected to SiNM n-channel MOSFET; or a first and a second frequency modulated millimeter wave (FMCW) radar sensors, enabling cutaneous pressure pulse wave measurement from the common carotid artery.

13. The wearable patch of claim 2 wherein the second central member end is configured to be located at a mid-sternum of the user.

14. A backend analysis system configured to receive data from a wearable patch for predicting heart failure events (HFE) comprising:

a waveform predictor module, wherein the waveform predictor module is configured to take physiological waveforms from the wearable patch worn by a patient over past several days (cycles) as input and uses it to predict the waveforms the patient is likely to develop over the next few days (cycles);

a computational module, wherein the computational module is configured to calculate relevant parameters from characteristic points of all of the predicted waveforms;

a set of comparator engines, wherein one of the comparator engines is configured for a stochastic comparison of the parameters obtained at different time cycles from the predicted waveforms; and the other engine is configured for a stochastic comparison of the parameters obtained at different time cycles from predicted ECG/EKG and thoracic bioimpedance waveforms;

a set of recurrent neural network (RNN) based learning modules, wherein the learning modules are configured to estimate a baseline model where baseline parameters are generated, based on a stochastic interdependent relationship between the predicted waveforms and the one between ECG/EKG and thoracic bioimpedance waveforms;

a baseline module, which is configured to compare the parameters obtained from the predicted waveforms against their respective baseline characteristics to determine the changes in cardiovascular or circulatory conditions;

an anomaly detector module, wherein the anomaly detector module is configured to detect abnormalities in the parameters obtained from the predicted waveforms; and an alert module for prompting an alert to the patient if the abnormalities detected by the anomaly detector module exceed a threshold value.

15. The wearable patch of claim 1, wherein the patch body comprises:

an elongated central body member having first and second central member ends, wherein, the first central member end is configured to be located at common carotid arteries at a neck region of the user, the second central member end is configured to be located at a sternum region of the user, and the central body member is configured to accommodate the controller; and first and second extension portions extending from the first central body member end in first and second lateral directions, wherein the first and second extension portions are configured to accommodate the first and second carotid arterial pressure sensors.

16. The wearable patch of claim 15 wherein the second central member end is configured to be located at a mid-sternum of the user.

* * * * *